(12) United States Patent
Yao et al.

(10) Patent No.: US 8,257,921 B1
(45) Date of Patent: Sep. 4, 2012

(54) NRIP1 REGULATION OF APOLIPOPROTEIN A1

(75) Inventors: Xiaorui Yao, Piscataway, NJ (US); Scott W. Altmann, Asbury Park, NJ (US); Liji Zhu, Oakland Gardens, NY (US)

(73) Assignee: Schering Corporation, Kenilworth, NJ (US)

( * ) Notice: Subject to any disclaimer, the term of this patent is extended or adjusted under 35 U.S.C. 154(b) by 336 days.

(21) Appl. No.: 12/644,674

(22) Filed: Dec. 22, 2009

Related U.S. Application Data

(60) Provisional application No. 61/139,842, filed on Dec. 22, 2008.

(51) Int. Cl.
*C12Q 1/68* (2006.01)

(52) U.S. Cl. ........................................... 435/6.1

(58) Field of Classification Search .................... 435/6.1
See application file for complete search history.

(56) References Cited

PUBLICATIONS

Harnish et al. (JBC 273:9270-9278, 1998).*

White R, Morganstein D, Christian M, Seth A, Herzog B, Parker MG. Role of RIP140 in metabolic tissues: connections to disease. FEBS Lett. Jan. 9, 2008;582(1):39-45. Epub Nov. 20, 2007.

Augereau P, Badia E, Balaguer P, Carascossa S, Castet A, Jalaguier S, Cavaillès V. Negative regulation of hormone signaling by RIP140. J Steroid Biochem Mol Biol. Dec. 2006;102(1-5):51-9. Epub Oct. 23, 2006.

Cavaillès V, Dauvois S, L'Horset F, Lopez G, Hoare S, Kushner PJ, Parker MG Nuclear factor RIP140 modulates transcriptional activation by the estrogen receptor. EMBO J. Aug. 1, 1995;14(15):3741-51.

Heery DM, Kalkhoven E, Hoare S, Parker MG. A signature motif in transcriptional co-activators mediates binding to nuclear receptors. Nature. Jun. 12, 1997;387(6634):733-6.

Lee CH, Chinpaisal C, Wei LN. Cloning and characterization of mouse RIP140, a corepressor for nuclear orphan receptor TR2. Mol Cell Biol. Nov. 1998;18(11):6745-55.

* cited by examiner

*Primary Examiner* — Brian Whiteman

(57) ABSTRACT

The present invention provides, in part, methods for identifying inhibitors of NRIP1 and methods of using such inhibitors. Methods of treating NRIP1-mediated disorders using NRIP1 inhibitor are also provided.

11 Claims, 9 Drawing Sheets

SEQUENCE LISTING

<160> NUMBER OF SEQ ID NOS: 25

<210> SEQ ID NO 1
<211> LENGTH: 5
<212> TYPE: PRT
<213> ORGANISM: Artificial Sequence
<220> FEATURE:
<223> OTHER INFORMATION: Nuclear receptor binding motif
<220> FEATURE:
<221> NAME/KEY: misc_feature
<222> LOCATION: (2)..(3)
<223> OTHER INFORMATION: Xaa can be any naturally occurring amino acid

<400> SEQUENCE: 1

```
Leu Xaa Xaa Leu Leu
1               5
```

<210> SEQ ID NO 2
<211> LENGTH: 5
<212> TYPE: PRT
<213> ORGANISM: Artificial Sequence
<220> FEATURE:
<223> OTHER INFORMATION: histone deacetylases and with C-terminal
      binding protein (CTBP) binding motif
<220> FEATURE:
<221> NAME/KEY: misc_feature
<222> LOCATION: (2)..(2)
<223> OTHER INFORMATION: Xaa can be any naturally occurring amino acid

<400> SEQUENCE: 2

```
Pro Xaa Asp Leu Ser
1               5
```

<210> SEQ ID NO 3
<211> LENGTH: 3477
<212> TYPE: DNA
<213> ORGANISM: Homo sapiens
<220> FEATURE:
<221> NAME/KEY: CDS
<222> LOCATION: (1)..(3477)

<400> SEQUENCE: 3

```
atg act cat gga gaa gag ctt ggc tct gat gtg cac cag gat tct att        48
Met Thr His Gly Glu Glu Leu Gly Ser Asp Val His Gln Asp Ser Ile
1               5                   10                  15 gtt tta act tac cta gaa gga tta cta atg cat cag gca gca ggg gga        96
Val Leu Thr Tyr Leu Glu Gly Leu Leu Met His Gln Ala Ala Gly Gly
                20                  25                  30 tca ggt act gcc gtt gac aaa aag tct gct ggg cat aat gaa gag gat       144
Ser Gly Thr Ala Val Asp Lys Lys Ser Ala Gly His Asn Glu Glu Asp
            35                  40                  45 cag aac ttt aac att tct ggc agt gca ttt ccc acc tgt caa agt aat       192
Gln Asn Phe Asn Ile Ser Gly Ser Ala Phe Pro Thr Cys Gln Ser Asn
        50                  55                  60 ggt cca gtt ctc aat aca cat aca tat cag ggg tct ggc atg ctg cac       240
Gly Pro Val Leu Asn Thr His Thr Tyr Gln Gly Ser Gly Met Leu His
65                  70                  75                  80 ctc aaa aaa gcc aga ctg ttg cag tct tct gag gac tgg aat gca gca       288
Leu Lys Lys Ala Arg Leu Leu Gln Ser Ser Glu Asp Trp Asn Ala Ala
                85                  90                  95 aag cgg aag agg ctg tct gat tct atc atg aat tta aac gta aag aag       336
Lys Arg Lys Arg Leu Ser Asp Ser Ile Met Asn Leu Asn Val Lys Lys
                100                 105                 110 gaa gct ttg cta gct ggc atg gtt gac agt gtg cct aaa ggc aaa cag       384
Glu Ala Leu Leu Ala Gly Met Val Asp Ser Val Pro Lys Gly Lys Gln
```

```
                    115                    120                    125
gat agc aca tta ctg gcc tct ttg ctt cag tca ttc agc tct agg ctg        432
Asp Ser Thr Leu Leu Ala Ser Leu Leu Gln Ser Phe Ser Ser Arg Leu
130                 135                 140 cag act gtt gct ctg tca caa caa atc agg cag agc ctc aag gag caa        480
Gln Thr Val Ala Leu Ser Gln Gln Ile Arg Gln Ser Leu Lys Glu Gln
145                 150                 155                 160 gga tat gcc ctc agt cat gat tct tta aaa gtg gag aag gat tta agg        528
Gly Tyr Ala Leu Ser His Asp Ser Leu Lys Val Glu Lys Asp Leu Arg
                165                 170                 175 tgc tat ggt gtt gca tca agt cac tta aaa act ttg ttg aag aaa agt        576
Cys Tyr Gly Val Ala Ser Ser His Leu Lys Thr Leu Leu Lys Lys Ser
            180                 185                 190 aaa gtt aaa gat caa aag cct gat acg aat ctt cct gat gtg act aaa        624
Lys Val Lys Asp Gln Lys Pro Asp Thr Asn Leu Pro Asp Val Thr Lys
        195                 200                 205 aac ctc atc aga gat agg ttt gca gag tct cct cat cat gtt gga caa        672
Asn Leu Ile Arg Asp Arg Phe Ala Glu Ser Pro His His Val Gly Gln
210                 215                 220 agt gga aca aag gtc atg agt gaa ccg ttg tca tgt gct gca aga tta        720
Ser Gly Thr Lys Val Met Ser Glu Pro Leu Ser Cys Ala Ala Arg Leu
225                 230                 235                 240 cag gct gtt gca agc atg gtg gaa aaa agg gct agt cct gcc acc tca        768
Gln Ala Val Ala Ser Met Val Glu Lys Arg Ala Ser Pro Ala Thr Ser
                245                 250                 255 cct aaa cct agt gtt gct tgt agc cag tta gca tta ctt ctg tca agc        816
Pro Lys Pro Ser Val Ala Cys Ser Gln Leu Ala Leu Leu Leu Ser Ser
            260                 265                 270 gaa gcc cat ttg cag cag tat tct cga gaa cac gct tta aaa acg caa        864
Glu Ala His Leu Gln Gln Tyr Ser Arg Glu His Ala Leu Lys Thr Gln
        275                 280                 285 aat gca aat caa gca gca agt gaa aga ctt gct gct atg gcc aga ttg        912
Asn Ala Asn Gln Ala Ala Ser Glu Arg Leu Ala Ala Met Ala Arg Leu
290                 295                 300 caa gaa aat ggc cag aag gat gtt ggc agt tac cag ctc cca aaa gga        960
Gln Glu Asn Gly Gln Lys Asp Val Gly Ser Tyr Gln Leu Pro Lys Gly
305                 310                 315                 320 atg tca agc cat ctt aat ggt cag gca aga aca tca tca agc aaa ctg       1008
Met Ser Ser His Leu Asn Gly Gln Ala Arg Thr Ser Ser Ser Lys Leu
                325                 330                 335 atg gct agc aaa agt agt gct aca gtg ttt caa aat cca atg ggt atc       1056
Met Ala Ser Lys Ser Ser Ala Thr Val Phe Gln Asn Pro Met Gly Ile
            340                 345                 350 att cct tct tcc cct aaa aat gca ggt tat aag aac tca ctg gaa aga       1104
Ile Pro Ser Ser Pro Lys Asn Ala Gly Tyr Lys Asn Ser Leu Glu Arg
        355                 360                 365 aac aat ata aaa caa gct gct aac aat agt ttg ctt tta cat ctt ctt       1152
Asn Asn Ile Lys Gln Ala Ala Asn Asn Ser Leu Leu Leu His Leu Leu
370                 375                 380 aaa agc cag act ata cct aag cca atg aat gga cac agt cac agt gag       1200
Lys Ser Gln Thr Ile Pro Lys Pro Met Asn Gly His Ser His Ser Glu
385                 390                 395                 400 aga gga agc att ttt gag gaa agt agt aca cct aca act att gat gaa       1248
Arg Gly Ser Ile Phe Glu Glu Ser Ser Thr Pro Thr Thr Ile Asp Glu
                405                 410                 415 tat tca gat aac aat cct agt ttt aca gat gac agc agt ggt gat gaa       1296
Tyr Ser Asp Asn Asn Pro Ser Phe Thr Asp Asp Ser Ser Gly Asp Glu
            420                 425                 430 agt tct tat tcc aac tgt gtt ccc ata gac ttg tct tgc aaa cac cga       1344
Ser Ser Tyr Ser Asn Cys Val Pro Ile Asp Leu Ser Cys Lys His Arg
```

```
                    435                 440                 445
act gaa aaa tca gaa tct gac caa cct gtt tcc ctg gat aac ttc act     1392
Thr Glu Lys Ser Glu Ser Asp Gln Pro Val Ser Leu Asp Asn Phe Thr
450                 455                 460 caa tcc ttg cta aac act tgg gat cca aaa gtc cca gat gta gat atc     1440
Gln Ser Leu Leu Asn Thr Trp Asp Pro Lys Val Pro Asp Val Asp Ile
465                 470                 475                 480 aaa gaa gat caa gat acc tca aag aat tct aag cta aac tca cac cag     1488
Lys Glu Asp Gln Asp Thr Ser Lys Asn Ser Lys Leu Asn Ser His Gln
                485                 490                 495 aaa gta aca ctt ctt caa ttg cta ctt ggc cat aag aat gaa gaa aat     1536
Lys Val Thr Leu Leu Gln Leu Leu Leu Gly His Lys Asn Glu Glu Asn
            500                 505                 510 gta gaa aaa aac acc agc cct cag gga gta cac aat gat gtg agc aag     1584
Val Glu Lys Asn Thr Ser Pro Gln Gly Val His Asn Asp Val Ser Lys
        515                 520                 525 ttc aat aca caa aat tat gca agg act tct gtg ata gaa agc ccc agt     1632
Phe Asn Thr Gln Asn Tyr Ala Arg Thr Ser Val Ile Glu Ser Pro Ser
530                 535                 540 aca aat cgg act act cca gtg agc act cca cct tta ctt aca tca agc     1680
Thr Asn Arg Thr Thr Pro Val Ser Thr Pro Pro Leu Leu Thr Ser Ser
545                 550                 555                 560 aaa gca ggg tct ccc atc aat ctc tct caa cac tct ctg gtc atc aaa     1728
Lys Ala Gly Ser Pro Ile Asn Leu Ser Gln His Ser Leu Val Ile Lys
                565                 570                 575 tgg aat tcc cca cca tat gtc tgc agt act cag tct gaa aag cta aca     1776
Trp Asn Ser Pro Pro Tyr Val Cys Ser Thr Gln Ser Glu Lys Leu Thr
            580                 585                 590 aat act gca tct aac cac tca atg gac ctt aca aaa agc aaa gac cca     1824
Asn Thr Ala Ser Asn His Ser Met Asp Leu Thr Lys Ser Lys Asp Pro
        595                 600                 605 cca gga gag aaa cca gcc caa aat gaa ggt gca cag aac tct gca acg     1872
Pro Gly Glu Lys Pro Ala Gln Asn Glu Gly Ala Gln Asn Ser Ala Thr
610                 615                 620 ttt agt gcc agt aag ctg tta caa aat tta gca caa tgt gga atg cag     1920
Phe Ser Ala Ser Lys Leu Leu Gln Asn Leu Ala Gln Cys Gly Met Gln
625                 630                 635                 640 tca tcc atg tca gtg gaa gag cag aga ccc agc aaa cag ctg tta act     1968
Ser Ser Met Ser Val Glu Glu Gln Arg Pro Ser Lys Gln Leu Leu Thr
                645                 650                 655 gga aac aca gat aaa ccg ata ggt atg att gat aga tta aat agc cct     2016
Gly Asn Thr Asp Lys Pro Ile Gly Met Ile Asp Arg Leu Asn Ser Pro
            660                 665                 670 ttg ctc tca aat aaa aca aat gca gtt gaa gaa aat aaa gca ttt agt     2064
Leu Leu Ser Asn Lys Thr Asn Ala Val Glu Glu Asn Lys Ala Phe Ser
        675                 680                 685 agt caa cca aca ggt cct gaa cca ggg ctt tct ggt tct gaa ata gaa     2112
Ser Gln Pro Thr Gly Pro Glu Pro Gly Leu Ser Gly Ser Glu Ile Glu
690                 695                 700 aat ctg ctt gaa aga cgt act gtc ctc cag ttg ctc ctg ggg aac ccc     2160
Asn Leu Leu Glu Arg Arg Thr Val Leu Gln Leu Leu Leu Gly Asn Pro
705                 710                 715                 720 aac aaa ggg aag agt gaa aaa aaa gag aaa act ccc tta aga gat gaa     2208
Asn Lys Gly Lys Ser Glu Lys Lys Glu Lys Thr Pro Leu Arg Asp Glu
                725                 730                 735 agt act cag gaa cac tca gag aga gct tta agt gaa caa ata ctg atg     2256
Ser Thr Gln Glu His Ser Glu Arg Ala Leu Ser Glu Gln Ile Leu Met
            740                 745                 750 gtg aaa ata aaa tct gag cct tgt gat gac tta caa att cct aac aca     2304
Val Lys Ile Lys Ser Glu Pro Cys Asp Asp Leu Gln Ile Pro Asn Thr
```

```
                755                 760                 765
aat gtg cac ttg agc cat gat gct aag agt gcc cca ttc ttg ggt atg        2352
Asn Val His Leu Ser His Asp Ala Lys Ser Ala Pro Phe Leu Gly Met
770                 775                 780 gct cct gct gtg cag aga agc gca cct gcc tta cca gtg tcc gaa gac        2400
Ala Pro Ala Val Gln Arg Ser Ala Pro Ala Leu Pro Val Ser Glu Asp
785                 790                 795                 800 ttt aaa tcg gag cct gtt tca cct cag gat ttt tct ttc tcc aag aat        2448
Phe Lys Ser Glu Pro Val Ser Pro Gln Asp Phe Ser Phe Ser Lys Asn
                805                 810                 815 ggt ctg cta agt cga ttg cta aga caa aat caa gat agt tac ctg gca        2496
Gly Leu Leu Ser Arg Leu Leu Arg Gln Asn Gln Asp Ser Tyr Leu Ala
            820                 825                 830 gat gat tca gac agg agt cac aga aat aat gaa atg gca ctt cta gaa        2544
Asp Asp Ser Asp Arg Ser His Arg Asn Asn Glu Met Ala Leu Leu Glu
        835                 840                 845 tca aag aat ctt tgc atg gtc cct aag aaa agg aag ctt tat act gag        2592
Ser Lys Asn Leu Cys Met Val Pro Lys Lys Arg Lys Leu Tyr Thr Glu
850                 855                 860 cca tta gaa aat cca ttt aaa aag atg aaa aac aac att gtt gat gct        2640
Pro Leu Glu Asn Pro Phe Lys Lys Met Lys Asn Asn Ile Val Asp Ala
865                 870                 875                 880 gca aac aat cac agt gcc cca gaa gta ctg tat ggg tcc ttg ctt aac        2688
Ala Asn Asn His Ser Ala Pro Glu Val Leu Tyr Gly Ser Leu Leu Asn
                885                 890                 895 cag gaa gag ctg aaa ttt agc aga aat gat ctt gaa ttt aaa tat cct        2736
Gln Glu Glu Leu Lys Phe Ser Arg Asn Asp Leu Glu Phe Lys Tyr Pro
            900                 905                 910 gct ggt cat ggc tca gcc agc gaa agt gaa cac agg agt tgg gcc aga        2784
Ala Gly His Gly Ser Ala Ser Glu Ser Glu His Arg Ser Trp Ala Arg
        915                 920                 925 gag agc aaa agc ttt aat gtt ctg aaa cag ctg ctt ctc tca gaa aac        2832
Glu Ser Lys Ser Phe Asn Val Leu Lys Gln Leu Leu Leu Ser Glu Asn
930                 935                 940 tgt gtg cga gat ttg tcc ccg cac aga agt aac tct gtg gct gac agt        2880
Cys Val Arg Asp Leu Ser Pro His Arg Ser Asn Ser Val Ala Asp Ser
945                 950                 955                 960 aaa aag aaa gga cac aaa aat aat gtg acc aac agc aaa cct gaa ttt        2928
Lys Lys Lys Gly His Lys Asn Asn Val Thr Asn Ser Lys Pro Glu Phe
                965                 970                 975 agc att tct tct tta aat gga ctg atg tac agt tcc act cag ccc agc        2976
Ser Ile Ser Ser Leu Asn Gly Leu Met Tyr Ser Ser Thr Gln Pro Ser
            980                 985                 990 agt tgc atg gat aac agg aca ttt tca tac cca ggt gta gta aaa act        3024
Ser Cys Met Asp Asn Arg Thr Phe Ser Tyr Pro Gly Val Val Lys Thr
        995                1000                1005 cct gtg agt cct act ttc cct gag cac ttg ggc tgt gca ggg tct        3069
Pro Val Ser Pro Thr Phe Pro Glu His Leu Gly Cys Ala Gly Ser
    1010                1015                1020 aga cca gaa tct ggg ctt ttg aat ggg tgt tcc atg ccc agt gag        3114
Arg Pro Glu Ser Gly Leu Leu Asn Gly Cys Ser Met Pro Ser Glu
1025                1030                1035 aaa gga ccc att aag tgg gtt atc act gat gcg gag aag aat gag        3159
Lys Gly Pro Ile Lys Trp Val Ile Thr Asp Ala Glu Lys Asn Glu
    1040                1045                1050 tat gaa aaa gac tct cca aga ttg acc aaa acc aac cca ata cta        3204
Tyr Glu Lys Asp Ser Pro Arg Leu Thr Lys Thr Asn Pro Ile Leu
1055                1060                1065 tat tac atg ctt caa aaa gga ggc aat tct gtt acc agt cga gaa        3249
Tyr Tyr Met Leu Gln Lys Gly Gly Asn Ser Val Thr Ser Arg Glu
```

```
            1070                1075                1080
aca caa gac aag gac att tgg agg gag gct tca tct gct gaa agt          3294
Thr Gln Asp Lys Asp Ile Trp Arg Glu Ala Ser Ser Ala Glu Ser
        1085                1090                1095 gtc tca cag gtc aca gcc aaa gaa gag tta ctt cct act gca gaa          3339
Val Ser Gln Val Thr Ala Lys Glu Glu Leu Leu Pro Thr Ala Glu
    1100                1105                1110 acg aaa gct tct ttc ttt aat tta aga agc cct tac aat agc cat          3384
Thr Lys Ala Ser Phe Phe Asn Leu Arg Ser Pro Tyr Asn Ser His
    1115                1120                1125 atg gga aat aat gct tct cgc cca cac agc gca aat gga gaa gtt          3429
Met Gly Asn Asn Ala Ser Arg Pro His Ser Ala Asn Gly Glu Val
    1130                1135                1140 tat gga ctt ctg gga agc gtg cta acg ata aag aaa gaa tca gaa          3474
Tyr Gly Leu Leu Gly Ser Val Leu Thr Ile Lys Lys Glu Ser Glu
    1145                1150                1155 taa                                                                   3477

<210> SEQ ID NO 4
<211> LENGTH: 1158
<212> TYPE: PRT
<213> ORGANISM: Homo sapiens

<400> SEQUENCE: 4

Met Thr His Gly Glu Glu Leu Gly Ser Asp Val His Gln Asp Ser Ile
1               5                   10                  15

Val Leu Thr Tyr Leu Glu Gly Leu Leu Met His Gln Ala Ala Gly Gly
            20                  25                  30

Ser Gly Thr Ala Val Asp Lys Lys Ser Ala Gly His Asn Glu Glu Asp
        35                  40                  45

Gln Asn Phe Asn Ile Ser Gly Ser Ala Phe Pro Thr Cys Gln Ser Asn
    50                  55                  60

Gly Pro Val Leu Asn Thr His Thr Tyr Gln Gly Ser Gly Met Leu His
65                  70                  75                  80

Leu Lys Lys Ala Arg Leu Leu Gln Ser Ser Glu Asp Trp Asn Ala Ala
                85                  90                  95

Lys Arg Lys Arg Leu Ser Asp Ser Ile Met Asn Leu Asn Val Lys Lys
            100                 105                 110

Glu Ala Leu Leu Ala Gly Met Val Asp Ser Val Pro Lys Gly Lys Gln
        115                 120                 125

Asp Ser Thr Leu Leu Ala Ser Leu Leu Gln Ser Phe Ser Ser Arg Leu
    130                 135                 140

Gln Thr Val Ala Leu Ser Gln Gln Ile Arg Gln Ser Leu Lys Glu Gln
145                 150                 155                 160

Gly Tyr Ala Leu Ser His Asp Ser Leu Lys Val Glu Lys Asp Leu Arg
                165                 170                 175

Cys Tyr Gly Val Ala Ser Ser His Leu Lys Thr Leu Leu Lys Lys Ser
            180                 185                 190

Lys Val Lys Asp Gln Lys Pro Asp Thr Asn Leu Pro Asp Val Thr Lys
        195                 200                 205

Asn Leu Ile Arg Asp Arg Phe Ala Glu Ser Pro His His Val Gly Gln
    210                 215                 220

Ser Gly Thr Lys Val Met Ser Glu Pro Leu Ser Cys Ala Ala Arg Leu
225                 230                 235                 240

Gln Ala Val Ala Ser Met Val Glu Lys Arg Ala Ser Pro Ala Thr Ser
                245                 250                 255
```

```
Pro Lys Pro Ser Val Ala Cys Ser Gln Leu Ala Leu Leu Leu Ser Ser
            260                 265                 270

Glu Ala His Leu Gln Gln Tyr Ser Arg Glu His Ala Leu Lys Thr Gln
        275                 280                 285

Asn Ala Asn Gln Ala Ala Ser Glu Arg Leu Ala Ala Met Ala Arg Leu
    290                 295                 300

Gln Glu Asn Gly Gln Lys Asp Val Gly Ser Tyr Gln Leu Pro Lys Gly
305                 310                 315                 320

Met Ser Ser His Leu Asn Gly Gln Ala Arg Thr Ser Ser Ser Lys Leu
                325                 330                 335

Met Ala Ser Lys Ser Ser Ala Thr Val Phe Gln Asn Pro Met Gly Ile
            340                 345                 350

Ile Pro Ser Ser Pro Lys Asn Ala Gly Tyr Lys Asn Ser Leu Glu Arg
        355                 360                 365

Asn Asn Ile Lys Gln Ala Ala Asn Asn Ser Leu Leu Leu His Leu Leu
    370                 375                 380

Lys Ser Gln Thr Ile Pro Lys Pro Met Asn Gly His Ser His Ser Glu
385                 390                 395                 400

Arg Gly Ser Ile Phe Glu Glu Ser Ser Thr Pro Thr Thr Ile Asp Glu
                405                 410                 415

Tyr Ser Asp Asn Asn Pro Ser Phe Thr Asp Ser Ser Gly Asp Glu
            420                 425                 430

Ser Ser Tyr Ser Asn Cys Val Pro Ile Asp Leu Ser Cys Lys His Arg
        435                 440                 445

Thr Glu Lys Ser Glu Ser Asp Gln Pro Val Ser Leu Asp Asn Phe Thr
    450                 455                 460

Gln Ser Leu Leu Asn Thr Trp Asp Pro Lys Val Pro Asp Val Asp Ile
465                 470                 475                 480

Lys Glu Asp Gln Asp Thr Ser Lys Asn Ser Lys Leu Asn Ser His Gln
                485                 490                 495

Lys Val Thr Leu Leu Gln Leu Leu Gly His Lys Asn Glu Glu Asn
            500                 505                 510

Val Glu Lys Asn Thr Ser Pro Gln Gly Val His Asn Asp Val Ser Lys
        515                 520                 525

Phe Asn Thr Gln Asn Tyr Ala Arg Thr Ser Val Ile Glu Ser Pro Ser
    530                 535                 540

Thr Asn Arg Thr Thr Pro Val Ser Thr Pro Pro Leu Leu Thr Ser Ser
545                 550                 555                 560

Lys Ala Gly Ser Pro Ile Asn Leu Ser Gln His Ser Leu Val Ile Lys
                565                 570                 575

Trp Asn Ser Pro Pro Tyr Val Cys Ser Thr Gln Ser Glu Lys Leu Thr
            580                 585                 590

Asn Thr Ala Ser Asn His Ser Met Asp Leu Thr Lys Ser Lys Asp Pro
        595                 600                 605

Pro Gly Glu Lys Pro Ala Gln Asn Glu Gly Ala Gln Asn Ser Ala Thr
    610                 615                 620

Phe Ser Ala Ser Lys Leu Leu Gln Asn Leu Ala Gln Cys Gly Met Gln
625                 630                 635                 640

Ser Ser Met Ser Val Glu Glu Gln Arg Pro Ser Lys Gln Leu Leu Thr
                645                 650                 655

Gly Asn Thr Asp Lys Pro Ile Gly Met Ile Asp Arg Leu Asn Ser Pro
            660                 665                 670

Leu Leu Ser Asn Lys Thr Asn Ala Val Glu Glu Asn Lys Ala Phe Ser
        675                 680                 685
```

```
Ser Gln Pro Thr Gly Pro Glu Pro Gly Leu Ser Gly Ser Glu Ile Glu
    690             695                 700
Asn Leu Leu Glu Arg Arg Thr Val Leu Gln Leu Leu Leu Gly Asn Pro
705             710                 715                 720
Asn Lys Gly Lys Ser Glu Lys Lys Glu Lys Thr Pro Leu Arg Asp Glu
                725                 730                 735
Ser Thr Gln Glu His Ser Glu Arg Ala Leu Ser Glu Gln Ile Leu Met
            740                 745                 750
Val Lys Ile Lys Ser Glu Pro Cys Asp Asp Leu Gln Ile Pro Asn Thr
        755                 760                 765
Asn Val His Leu Ser His Asp Ala Lys Ser Ala Pro Phe Leu Gly Met
    770                 775                 780
Ala Pro Ala Val Gln Arg Ser Pro Ala Leu Pro Val Ser Glu Asp
785             790                 795                 800
Phe Lys Ser Glu Pro Val Ser Pro Gln Asp Phe Ser Phe Ser Lys Asn
                805                 810                 815
Gly Leu Leu Ser Arg Leu Leu Arg Gln Asn Gln Asp Ser Tyr Leu Ala
            820                 825                 830
Asp Asp Ser Asp Arg Ser His Arg Asn Asn Glu Met Ala Leu Leu Glu
        835                 840                 845
Ser Lys Asn Leu Cys Met Val Pro Lys Lys Arg Lys Leu Tyr Thr Glu
    850                 855                 860
Pro Leu Glu Asn Pro Phe Lys Lys Met Lys Asn Asn Ile Val Asp Ala
865             870                 875                 880
Ala Asn His Ser Ala Pro Glu Val Leu Tyr Gly Ser Leu Leu Asn
                885                 890                 895
Gln Glu Glu Leu Lys Phe Ser Arg Asn Asp Leu Glu Phe Lys Tyr Pro
            900                 905                 910
Ala Gly His Gly Ser Ala Ser Glu Ser Glu His Arg Ser Trp Ala Arg
        915                 920                 925
Glu Ser Lys Ser Phe Asn Val Leu Lys Gln Leu Leu Leu Ser Glu Asn
    930                 935                 940
Cys Val Arg Asp Leu Ser Pro His Arg Ser Asn Ser Val Ala Asp Ser
945             950                 955                 960
Lys Lys Lys Gly His Lys Asn Asn Val Thr Asn Ser Lys Pro Glu Phe
                965                 970                 975
Ser Ile Ser Ser Leu Asn Gly Leu Met Tyr Ser Ser Thr Gln Pro Ser
            980                 985                 990
Ser Cys Met Asp Asn Arg Thr Phe Ser Tyr Pro Gly Val Val Lys Thr
        995                 1000                1005
Pro Val Ser Pro Thr Phe Pro Glu His Leu Gly Cys Ala Gly Ser
    1010                1015                1020
Arg Pro Glu Ser Gly Leu Leu Asn Gly Cys Ser Met Pro Ser Glu
    1025                1030                1035
Lys Gly Pro Ile Lys Trp Val Ile Thr Asp Ala Glu Lys Asn Glu
    1040                1045                1050
Tyr Glu Lys Asp Ser Pro Arg Leu Thr Lys Thr Asn Pro Ile Leu
    1055                1060                1065
Tyr Tyr Met Leu Gln Lys Gly Gly Asn Ser Val Thr Ser Arg Glu
    1070                1075                1080
Thr Gln Asp Lys Asp Ile Trp Arg Glu Ala Ser Ser Ala Glu Ser
    1085                1090                1095
Val Ser Gln Val Thr Ala Lys Glu Glu Leu Leu Pro Thr Ala Glu
```

-continued

```
                   1100                1105                1110

Thr Lys Ala Ser Phe Phe Asn  Leu Arg Ser Pro Tyr  Asn Ser His
    1115                1120                1125

Met Gly Asn Asn Ala Ser Arg  Pro His Ser Ala Asn  Gly Glu Val
    1130                1135                1140

Tyr Gly Leu Leu Gly Ser Val  Leu Thr Ile Lys Lys  Glu Ser Glu
    1145                1150                1155

<210> SEQ ID NO 5
<211> LENGTH: 3486
<212> TYPE: DNA
<213> ORGANISM: Mus
<220> FEATURE:
<221> NAME/KEY: CDS
<222> LOCATION: (1)..(3486)

<400> SEQUENCE: 5 atg act cat gga gaa gag ctt ggc tct gat gtg cat cag gat tct att      48
Met Thr His Gly Glu Glu Leu Gly Ser Asp Val His Gln Asp Ser Ile
 1               5                  10                  15 gtc tta act tac ctc gaa ggg tta cta atg cat cag gca gca ggg gga      96
Val Leu Thr Tyr Leu Glu Gly Leu Leu Met His Gln Ala Ala Gly Gly
             20                  25                  30 tca ggc act gcc att aac aaa aag tct gct ggc cac aaa gag gaa gac     144
Ser Gly Thr Ala Ile Asn Lys Lys Ser Ala Gly His Lys Glu Glu Asp
         35                  40                  45 cag aac ttt aac ctc tcg ggc agt gcg ttt ccc tcc tgt caa agc aat     192
Gln Asn Phe Asn Leu Ser Gly Ser Ala Phe Pro Ser Cys Gln Ser Asn
     50                  55                  60 ggt ccc act gtc agt acc cag acg tac cag gga tct ggc atg ctg cac     240
Gly Pro Thr Val Ser Thr Gln Thr Tyr Gln Gly Ser Gly Met Leu His
 65                  70                  75                  80 ctc aaa aaa gcc aga ctg ctg cag tct tcc gag gac tgg aac gcg gca     288
Leu Lys Lys Ala Arg Leu Leu Gln Ser Ser Glu Asp Trp Asn Ala Ala
                 85                  90                  95 aag cgg aag agg ctg tct gat tcc atc gtg aat tta aac gta aag aag     336
Lys Arg Lys Arg Leu Ser Asp Ser Ile Val Asn Leu Asn Val Lys Lys
            100                 105                 110 gaa gcg ttg ctg gct ggc atg gtt gac agt gtg cct aaa ggc aaa cag     384
Glu Ala Leu Leu Ala Gly Met Val Asp Ser Val Pro Lys Gly Lys Gln
        115                 120                 125 gat agc aca ttg ctg gcc tct ttg ctt cag tca ttc agc tct agg ctg     432
Asp Ser Thr Leu Leu Ala Ser Leu Leu Gln Ser Phe Ser Ser Arg Leu
    130                 135                 140 cag act gtt gct ctg tca cag cag att aga cag agc ctc aag gag cag     480
Gln Thr Val Ala Leu Ser Gln Gln Ile Arg Gln Ser Leu Lys Glu Gln
145                 150                 155                 160 gga tat gcc ctc agt cac gag tct tta aaa gtg gag aag gat tta agg     528
Gly Tyr Ala Leu Ser His Glu Ser Leu Lys Val Glu Lys Asp Leu Arg
                165                 170                 175 tgc tat ggc gtg gcc tca agt cac tta aaa act ctg ttg aag aaa agt     576
Cys Tyr Gly Val Ala Ser Ser His Leu Lys Thr Leu Leu Lys Lys Ser
            180                 185                 190 aaa acc aag gat caa aag tca ggt ccc acc ctc cct gac gtg act cca     624
Lys Thr Lys Asp Gln Lys Ser Gly Pro Thr Leu Pro Asp Val Thr Pro
        195                 200                 205 aac ctt atc aga gat agc ttt gtt gag tca tcc cat ccc gca gtg gga     672
Asn Leu Ile Arg Asp Ser Phe Val Glu Ser Ser His Pro Ala Val Gly
    210                 215                 220 caa agt ggg aca aag gtc atg agt gag ccc ttg tca tgt gct gca aga     720
Gln Ser Gly Thr Lys Val Met Ser Glu Pro Leu Ser Cys Ala Ala Arg
```

```
                       225                 230                 235                 240 tta cag gct gtt gcc agc atg gtg gag aaa agg gcg agt ccc gct gcc        768
Leu Gln Ala Val Ala Ser Met Val Glu Lys Arg Ala Ser Pro Ala Ala
                       245                 250                 255 tcc cca aag cct agt gtt gcc tgc agc cag ttg gcg ctg ctc ctg tcc        816
Ser Pro Lys Pro Ser Val Ala Cys Ser Gln Leu Ala Leu Leu Leu Ser
            260                 265                 270 agc gag gcc cac ctg cag cag tac tct cgg gaa cat gct cta aaa acg        864
Ser Glu Ala His Leu Gln Gln Tyr Ser Arg Glu His Ala Leu Lys Thr
                275                 280                 285 cag aac gca cat cag gtg gca agc gaa aga ctt gca gcc atg gcc aga        912
Gln Asn Ala His Gln Val Ala Ser Glu Arg Leu Ala Ala Met Ala Arg
            290                 295                 300 ttg caa gag aat ggg cag aag gac gtg ggc agt tcg cag ctc tcc aaa        960
Leu Gln Glu Asn Gly Gln Lys Asp Val Gly Ser Ser Gln Leu Ser Lys
305                 310                 315                 320 ggg gtg tct ggc cat ctc aac ggg cag gcc aga gca ctg ccg gca agc       1008
Gly Val Ser Gly His Leu Asn Gly Gln Ala Arg Ala Leu Pro Ala Ser
                            325                 330                 335 aaa ctg gtg gcc aac aag aat aac gct gcc acc ttt cag agt cca atg       1056
Lys Leu Val Ala Asn Lys Asn Asn Ala Ala Thr Phe Gln Ser Pro Met
                340                 345                 350 ggt gtt gtc cct tcc tcc ccc aaa aac acg agc tat aag aac tca ctg       1104
Gly Val Val Pro Ser Ser Pro Lys Asn Thr Ser Tyr Lys Asn Ser Leu
            355                 360                 365 gaa aga aac aac cta aag cag gct gct aat aac agt ctg ctt ttg cat       1152
Glu Arg Asn Asn Leu Lys Gln Ala Ala Asn Asn Ser Leu Leu Leu His
                370                 375                 380 ctc ctc aaa agc cag acc ata ccc acg ccg atg aac ggg cac agc cag       1200
Leu Leu Lys Ser Gln Thr Ile Pro Thr Pro Met Asn Gly His Ser Gln
385                 390                 395                 400 aac gag aga gcg agc agt ttt gag agt agc acg ccc acc acg att gat       1248
Asn Glu Arg Ala Ser Ser Phe Glu Ser Ser Thr Pro Thr Thr Ile Asp
                            405                 410                 415 gag tac tcc gat aac aac ccg agc ttt aca gat gac agc agt gga gac       1296
Glu Tyr Ser Asp Asn Asn Pro Ser Phe Thr Asp Asp Ser Ser Gly Asp
                420                 425                 430 gaa agc tcg tac tcc aat tgc gtt ccc ata gac ctg tct tgc aaa cac       1344
Glu Ser Ser Tyr Ser Asn Cys Val Pro Ile Asp Leu Ser Cys Lys His
            435                 440                 445 cgg atc gaa aag ccg gaa gct gag cgg ccc gtt tcg ctg gag aac cta       1392
Arg Ile Glu Lys Pro Glu Ala Glu Arg Pro Val Ser Leu Glu Asn Leu
                450                 455                 460 acc cag tcc ttg tta aac acg tgg gat ccc aag atc ccc ggc gtt gac       1440
Thr Gln Ser Leu Leu Asn Thr Trp Asp Pro Lys Ile Pro Gly Val Asp
465                 470                 475                 480 atc aaa gaa gat caa gat acc tca aca aat tcc aag ctg aat tca cac       1488
Ile Lys Glu Asp Gln Asp Thr Ser Thr Asn Ser Lys Leu Asn Ser His
                            485                 490                 495 cag aaa gtc act ctt ctt cag ttg ctg ctc ggc cat aaa agt gaa gaa       1536
Gln Lys Val Thr Leu Leu Gln Leu Leu Leu Gly His Lys Ser Glu Glu
                500                 505                 510 act gtt gaa agg aac gcc agc cct cag gac atc cat agt gat ggg act       1584
Thr Val Glu Arg Asn Ala Ser Pro Gln Asp Ile His Ser Asp Gly Thr
            515                 520                 525 aag ttc agt cct cag aat tac aca agg act tct gtc atc gaa agc ccc       1632
Lys Phe Ser Pro Gln Asn Tyr Thr Arg Thr Ser Val Ile Glu Ser Pro
                530                 535                 540 agt acc aac agg act acc cca gtg agc act cca cca ctg tat aca gcc       1680
Ser Thr Asn Arg Thr Thr Pro Val Ser Thr Pro Pro Leu Tyr Thr Ala
```

```
                          -continued
545              550              555              560 agc caa gca gag tct ccc atc aat ctt tcc cag cac tct ctg gtc atc      1728
Ser Gln Ala Glu Ser Pro Ile Asn Leu Ser Gln His Ser Leu Val Ile
                565              570              575 aag tgg aat tcc ccg ccg tat gcc tgc agt act ccc gct tcc aag ctc      1776
Lys Trp Asn Ser Pro Pro Tyr Ala Cys Ser Thr Pro Ala Ser Lys Leu
                580              585              590 acg aac acc gcg cct agc cac ctg atg gac ctc acg aaa ggc aaa gag      1824
Thr Asn Thr Ala Pro Ser His Leu Met Asp Leu Thr Lys Gly Lys Glu
        595              600              605 tcc caa gcc gag aaa cca gcc ccg agt gaa ggt gca caa aat tcc gcc      1872
Ser Gln Ala Glu Lys Pro Ala Pro Ser Glu Gly Ala Gln Asn Ser Ala
        610              615              620 acg ttc agt gcc agt aaa ctg tta caa aat ttg gct cag tgc gga ttg      1920
Thr Phe Ser Ala Ser Lys Leu Leu Gln Asn Leu Ala Gln Cys Gly Leu
625              630              635              640 cag tct tcc ggg cca ggg gaa gag cag aga ccc tgc aaa cag ctg tta      1968
Gln Ser Ser Gly Pro Gly Glu Glu Gln Arg Pro Cys Lys Gln Leu Leu
                645              650              655 agt gga aac cca gac aaa cct ctc ggt ctg att gat aga tta aac agc      2016
Ser Gly Asn Pro Asp Lys Pro Leu Gly Leu Ile Asp Arg Leu Asn Ser
                660              665              670 cct ctg ctc tca aat aaa acc aat gcg gct gaa gag agc aaa gcc ttc      2064
Pro Leu Leu Ser Asn Lys Thr Asn Ala Ala Glu Glu Ser Lys Ala Phe
        675              680              685 agc agt cag cct gcc ggg cct gag ccg gga ctt cct ggt tgt gag ata      2112
Ser Ser Gln Pro Ala Gly Pro Glu Pro Gly Leu Pro Gly Cys Glu Ile
        690              695              700 gaa aat ctc ttg gaa aga cgg act gtc ctt cag ttg ctc ctg gga aat      2160
Glu Asn Leu Leu Glu Arg Arg Thr Val Leu Gln Leu Leu Leu Gly Asn
705              710              715              720 tcc agc aaa ggg aag aat gag aag aaa gag aaa acc ccc gca cga gac      2208
Ser Ser Lys Gly Lys Asn Glu Lys Lys Glu Lys Thr Pro Ala Arg Asp
                725              730              735 gag gct cct cag gag cat tcg gag agg gct gca aat gaa cag ata ctc      2256
Glu Ala Pro Gln Glu His Ser Glu Arg Ala Ala Asn Glu Gln Ile Leu
                740              745              750 atg gtg aag att aaa tcc gag cct tgt gac gac ttc cag acc cac aac      2304
Met Val Lys Ile Lys Ser Glu Pro Cys Asp Asp Phe Gln Thr His Asn
        755              760              765 aca aac ctg ccc tta aac cac gat gcc aag agc gcc ccc ttc tta ggt      2352
Thr Asn Leu Pro Leu Asn His Asp Ala Lys Ser Ala Pro Phe Leu Gly
        770              775              780 gtg act ccc gcc atc cac agg agc aca gcg gcc tta cca gtg tcg gag      2400
Val Thr Pro Ala Ile His Arg Ser Thr Ala Ala Leu Pro Val Ser Glu
785              790              795              800 gac ttt aaa tcc gag cct gct tca cct cag gat ttc tct ttc tca aag      2448
Asp Phe Lys Ser Glu Pro Ala Ser Pro Gln Asp Phe Ser Phe Ser Lys
                805              810              815 aac ggg ctg ttg agt cgc ttg ctg aga cag aat caa gag agt tac ccg      2496
Asn Gly Leu Leu Ser Arg Leu Leu Arg Gln Asn Gln Glu Ser Tyr Pro
                820              825              830 gca gat gag cag gac aag agt cac aga aac agt gag ctg cca acc ctg      2544
Ala Asp Glu Gln Asp Lys Ser His Arg Asn Ser Glu Leu Pro Thr Leu
        835              840              845 gag tcg aag aac atc tgc atg gtc ccg aag aaa agg aag ctg tat acg      2592
Glu Ser Lys Asn Ile Cys Met Val Pro Lys Lys Arg Lys Leu Tyr Thr
        850              855              860 gaa cca ctg gag aat cca ttt aaa aag atg aaa aat act gcc gta gat      2640
Glu Pro Leu Glu Asn Pro Phe Lys Lys Met Lys Asn Thr Ala Val Asp
```

-continued

| | |
|---|---|
| act gcc aat cat cac agc ggc ccg gaa gta ctc tac ggg tcg ttg ctt<br>Thr Ala Asn His His Ser Gly Pro Glu Val Leu Tyr Gly Ser Leu Leu<br>865             870              875             880<br>                      885              890              895 | 2688 |
| cat cag gaa gag ctg aag ttt agc agg aat gag ctc gat tat aaa tac<br>His Gln Glu Glu Leu Lys Phe Ser Arg Asn Glu Leu Asp Tyr Lys Tyr<br>              900              905              910 | 2736 |
| cct gct ggg cat agt tca gcc agc gat ggt gac cac agg agt tgg gcc<br>Pro Ala Gly His Ser Ser Ala Ser Asp Gly Asp His Arg Ser Trp Ala<br>              915              920              925 | 2784 |
| aga gag agc aaa agc ttc aat gtt ctc aag cag ctg ctg ctc tcc gag<br>Arg Glu Ser Lys Ser Phe Asn Val Leu Lys Gln Leu Leu Leu Ser Glu<br>930             935              940 | 2832 |
| aac tgt gtg cga gat ctg tcc cca cac agg agt gac tct gtc ccc gac<br>Asn Cys Val Arg Asp Leu Ser Pro His Arg Ser Asp Ser Val Pro Asp<br>945             950              955             960 | 2880 |
| acg aaa aag aaa gga cac aaa aac aac gcg ccc ggc agc aaa cct gaa<br>Thr Lys Lys Lys Gly His Lys Asn Asn Ala Pro Gly Ser Lys Pro Glu<br>              965              970              975 | 2928 |
| ttc ggc att tct tct tta aat gga ctg atg tat agt tcc ccg cag cct<br>Phe Gly Ile Ser Ser Leu Asn Gly Leu Met Tyr Ser Ser Pro Gln Pro<br>              980              985              990 | 2976 |
| ggc agt tgt gtg acg gat cat agg aca ttt tca tac ccg gga atg gta<br>Gly Ser Cys Val Thr Asp His Arg Thr Phe Ser Tyr Pro Gly Met Val<br>              995            1000           1005 | 3024 |
| aag acc cct ctg agc cct cct ttc cca gag cac ttg ggc tgt gtg<br>Lys Thr Pro Leu Ser Pro Pro Phe Pro Glu His Leu Gly Cys Val<br>1010             1015            1020 | 3069 |
| ggg tcc aga cca gaa cct ggg ctt ttg aat gga tgt tcc gtg ccc<br>Gly Ser Arg Pro Glu Pro Gly Leu Leu Asn Gly Cys Ser Val Pro<br>1025             1030            1035 | 3114 |
| ggt gag aag gga ccc att aag tgg gtc atc gca gat atg gat aag<br>Gly Glu Lys Gly Pro Ile Lys Trp Val Ile Ala Asp Met Asp Lys<br>1040             1045            1050 | 3159 |
| aat gaa tac gaa aaa gac tct cca aga ctg acc aaa act aat ccg<br>Asn Glu Tyr Glu Lys Asp Ser Pro Arg Leu Thr Lys Thr Asn Pro<br>1055             1060            1065 | 3204 |
| atc ctc tat tac atg ctc cag aag gga ggg ggc aat tct gtt acc<br>Ile Leu Tyr Tyr Met Leu Gln Lys Gly Gly Gly Asn Ser Val Thr<br>1070             1075            1080 | 3249 |
| aca caa gaa acc cag gac aaa gac atc tgg agg gag cct gcg tca<br>Thr Gln Glu Thr Gln Asp Lys Asp Ile Trp Arg Glu Pro Ala Ser<br>1085             1090            1095 | 3294 |
| gcc gag agt ctc tca cag gtt aca gtc aaa gaa gag cta ctt ccc<br>Ala Glu Ser Leu Ser Gln Val Thr Val Lys Glu Glu Leu Leu Pro<br>1100             1105            1110 | 3339 |
| gct gca gaa act aaa gct tct ttc ttt aat cta aga agc ccg tac<br>Ala Ala Glu Thr Lys Ala Ser Phe Phe Asn Leu Arg Ser Pro Tyr<br>1115             1120            1125 | 3384 |
| aat agc cat atg gga aat aat gct tct cgc cca cac agt aca aat<br>Asn Ser His Met Gly Asn Asn Ala Ser Arg Pro His Ser Thr Asn<br>1130             1135            1140 | 3429 |
| gga gaa gtg tat gga ctt ctg gga aac gcg ctc acc ata aaa aaa<br>Gly Glu Val Tyr Gly Leu Leu Gly Asn Ala Leu Thr Ile Lys Lys<br>1145             1150            1155 | 3474 |
| gag tca gaa taa<br>Glu Ser Glu<br>1160 | 3486 |

<210> SEQ ID NO 6

<211> LENGTH: 1161
<212> TYPE: PRT
<213> ORGANISM: Mus

<400> SEQUENCE: 6

```
Met Thr His Gly Glu Glu Leu Gly Ser Asp Val His Gln Asp Ser Ile
1               5                   10                  15

Val Leu Thr Tyr Leu Glu Gly Leu Leu Met His Gln Ala Ala Gly Gly
            20                  25                  30

Ser Gly Thr Ala Ile Asn Lys Lys Ser Ala Gly His Lys Glu Glu Asp
        35                  40                  45

Gln Asn Phe Asn Leu Ser Gly Ser Ala Phe Pro Ser Cys Gln Ser Asn
    50                  55                  60

Gly Pro Thr Val Ser Thr Gln Thr Tyr Gln Gly Ser Gly Met Leu His
65                  70                  75                  80

Leu Lys Lys Ala Arg Leu Leu Gln Ser Glu Asp Trp Asn Ala Ala
                85                  90                  95

Lys Arg Lys Arg Leu Ser Asp Ser Ile Val Asn Leu Asn Val Lys Lys
                100                 105                 110

Glu Ala Leu Leu Ala Gly Met Val Asp Ser Val Pro Lys Gly Lys Gln
            115                 120                 125

Asp Ser Thr Leu Leu Ala Ser Leu Leu Gln Ser Phe Ser Ser Arg Leu
    130                 135                 140

Gln Thr Val Ala Leu Ser Gln Gln Ile Arg Gln Ser Leu Lys Glu Gln
145                 150                 155                 160

Gly Tyr Ala Leu Ser His Glu Ser Leu Lys Val Glu Lys Asp Leu Arg
                165                 170                 175

Cys Tyr Gly Val Ala Ser Ser His Leu Lys Thr Leu Leu Lys Lys Ser
            180                 185                 190

Lys Thr Lys Asp Gln Lys Ser Gly Pro Thr Leu Pro Asp Val Thr Pro
        195                 200                 205

Asn Leu Ile Arg Asp Ser Phe Val Glu Ser Ser His Pro Ala Val Gly
    210                 215                 220

Gln Ser Gly Thr Lys Val Met Ser Glu Pro Leu Ser Cys Ala Ala Arg
225                 230                 235                 240

Leu Gln Ala Val Ala Ser Met Val Glu Lys Arg Ala Ser Pro Ala Ala
                245                 250                 255

Ser Pro Lys Pro Ser Val Ala Cys Ser Gln Leu Ala Leu Leu Leu Ser
            260                 265                 270

Ser Glu Ala His Leu Gln Gln Tyr Ser Arg Glu His Ala Leu Lys Thr
        275                 280                 285

Gln Asn Ala His Gln Val Ala Ser Glu Arg Leu Ala Ala Met Ala Arg
    290                 295                 300

Leu Gln Glu Asn Gly Gln Lys Asp Val Gly Ser Ser Gln Leu Ser Lys
305                 310                 315                 320

Gly Val Ser Gly His Leu Asn Gly Gln Ala Arg Ala Leu Pro Ala Ser
                325                 330                 335

Lys Leu Val Ala Asn Lys Asn Asn Ala Ala Thr Phe Gln Ser Pro Met
            340                 345                 350

Gly Val Val Pro Ser Ser Pro Lys Asn Thr Ser Tyr Lys Asn Ser Leu
        355                 360                 365

Glu Arg Asn Asn Leu Lys Gln Ala Ala Asn Ser Leu Leu Leu His
    370                 375                 380

Leu Leu Lys Ser Gln Thr Ile Pro Thr Pro Met Asn Gly His Ser Gln
385                 390                 395                 400
```

```
Asn Glu Arg Ala Ser Ser Phe Glu Ser Thr Pro Thr Thr Ile Asp
            405                 410                 415

Glu Tyr Ser Asp Asn Asn Pro Ser Phe Thr Asp Asp Ser Ser Gly Asp
        420                 425                 430

Glu Ser Ser Tyr Ser Asn Cys Val Pro Ile Asp Leu Ser Cys Lys His
            435                 440                 445

Arg Ile Glu Lys Pro Glu Ala Glu Arg Pro Val Ser Leu Glu Asn Leu
        450                 455                 460

Thr Gln Ser Leu Leu Asn Thr Trp Asp Pro Lys Ile Pro Gly Val Asp
465                 470                 475                 480

Ile Lys Glu Asp Gln Asp Thr Ser Thr Asn Ser Lys Leu Asn Ser His
                485                 490                 495

Gln Lys Val Thr Leu Leu Gln Leu Leu Leu Gly His Lys Ser Glu Glu
                500                 505                 510

Thr Val Glu Arg Asn Ala Ser Pro Gln Asp Ile His Ser Asp Gly Thr
            515                 520                 525

Lys Phe Ser Pro Gln Asn Tyr Thr Arg Thr Ser Val Ile Glu Ser Pro
        530                 535                 540

Ser Thr Asn Arg Thr Thr Pro Val Ser Thr Pro Pro Leu Tyr Thr Ala
545                 550                 555                 560

Ser Gln Ala Glu Ser Pro Ile Asn Leu Ser Gln His Ser Leu Val Ile
                565                 570                 575

Lys Trp Asn Ser Pro Pro Tyr Ala Cys Ser Thr Pro Ala Ser Lys Leu
                580                 585                 590

Thr Asn Thr Ala Pro Ser His Leu Met Asp Leu Thr Lys Gly Lys Glu
            595                 600                 605

Ser Gln Ala Glu Lys Pro Ala Pro Ser Glu Gly Ala Gln Asn Ser Ala
        610                 615                 620

Thr Phe Ser Ala Ser Lys Leu Leu Gln Asn Leu Ala Gln Cys Gly Leu
625                 630                 635                 640

Gln Ser Ser Gly Pro Gly Glu Glu Gln Arg Pro Cys Lys Gln Leu Leu
                645                 650                 655

Ser Gly Asn Pro Asp Lys Pro Leu Gly Leu Ile Asp Arg Leu Asn Ser
            660                 665                 670

Pro Leu Leu Ser Asn Lys Thr Asn Ala Ala Glu Glu Ser Lys Ala Phe
        675                 680                 685

Ser Ser Gln Pro Ala Gly Pro Glu Pro Gly Leu Pro Gly Cys Glu Ile
        690                 695                 700

Glu Asn Leu Leu Glu Arg Arg Thr Val Leu Gln Leu Leu Leu Gly Asn
705                 710                 715                 720

Ser Ser Lys Gly Lys Asn Glu Lys Lys Leu Thr Pro Ala Arg Asp
                725                 730                 735

Glu Ala Pro Gln Glu His Ser Glu Arg Ala Ala Asn Glu Gln Ile Leu
            740                 745                 750

Met Val Lys Ile Lys Ser Glu Pro Cys Asp Asp Phe Gln Thr His Asn
                755                 760                 765

Thr Asn Leu Pro Leu Asn His Asp Ala Lys Ser Ala Pro Phe Leu Gly
            770                 775                 780

Val Thr Pro Ala Ile His Arg Ser Thr Ala Ala Leu Pro Val Ser Glu
785                 790                 795                 800

Asp Phe Lys Ser Glu Pro Ala Ser Pro Gln Asp Phe Ser Phe Ser Lys
                805                 810                 815

Asn Gly Leu Leu Ser Arg Leu Leu Arg Gln Asn Gln Glu Ser Tyr Pro
```

```
                    820                 825                 830
Ala Asp Glu Gln Asp Lys Ser His Arg Asn Ser Glu Leu Pro Thr Leu
            835                 840                 845

Glu Ser Lys Asn Ile Cys Met Val Pro Lys Lys Arg Lys Leu Tyr Thr
            850                 855                 860

Glu Pro Leu Glu Asn Pro Phe Lys Lys Met Lys Asn Thr Ala Val Asp
865                 870                 875                 880

Thr Ala Asn His His Ser Gly Pro Glu Val Leu Tyr Gly Ser Leu Leu
                885                 890                 895

His Gln Glu Glu Leu Lys Phe Ser Arg Asn Glu Leu Asp Tyr Lys Tyr
            900                 905                 910

Pro Ala Gly His Ser Ser Ala Ser Asp Gly Asp His Arg Ser Trp Ala
            915                 920                 925

Arg Glu Ser Lys Ser Phe Asn Val Leu Lys Gln Leu Leu Leu Ser Glu
            930                 935                 940

Asn Cys Val Arg Asp Leu Ser Pro His Arg Ser Asp Ser Val Pro Asp
945                 950                 955                 960

Thr Lys Lys Lys Gly His Lys Asn Asn Ala Pro Gly Ser Lys Pro Glu
                965                 970                 975

Phe Gly Ile Ser Ser Leu Asn Gly Leu Met Tyr Ser Ser Pro Gln Pro
            980                 985                 990

Gly Ser Cys Val Thr Asp His Arg Thr Phe Ser Tyr Pro Gly Met Val
            995                 1000                1005

Lys Thr Pro Leu Ser Pro Pro Phe Pro Glu His Leu Gly Cys Val
    1010                1015                1020

Gly Ser Arg Pro Glu Pro Gly Leu Leu Asn Gly Cys Ser Val Pro
    1025                1030                1035

Gly Glu Lys Gly Pro Ile Lys Trp Val Ile Ala Asp Met Asp Lys
    1040                1045                1050

Asn Glu Tyr Glu Lys Asp Ser Pro Arg Leu Thr Lys Thr Asn Pro
    1055                1060                1065

Ile Leu Tyr Tyr Met Leu Gln Lys Gly Gly Asn Ser Val Thr
    1070                1075                1080

Thr Gln Glu Thr Gln Asp Lys Asp Ile Trp Arg Glu Pro Ala Ser
    1085                1090                1095

Ala Glu Ser Leu Ser Gln Val Thr Val Lys Glu Glu Leu Leu Pro
    1100                1105                1110

Ala Ala Glu Thr Lys Ala Ser Phe Phe Asn Leu Arg Ser Pro Tyr
    1115                1120                1125

Asn Ser His Met Gly Asn Asn Ala Ser Arg Pro His Ser Thr Asn
    1130                1135                1140

Gly Glu Val Tyr Gly Leu Leu Gly Asn Ala Leu Thr Ile Lys Lys
    1145                1150                1155

Glu Ser Glu
    1160

<210> SEQ ID NO 7
<211> LENGTH: 21
<212> TYPE: RNA
<213> ORGANISM: Artificial Sequence
<220> FEATURE:
<223> OTHER INFORMATION: siRNA #27-5

<400> SEQUENCE: 7
gaagcgugcu aacgauaaau u                                              21
```

```
<210> SEQ ID NO 8
<211> LENGTH: 21
<212> TYPE: RNA
<213> ORGANISM: Artificial Sequence
<220> FEATURE:
<223> OTHER INFORMATION: siRNA #27-6

<400> SEQUENCE: 8
agaaggaugu uggcaguuau u                                            21

<210> SEQ ID NO 9
<211> LENGTH: 21
<212> TYPE: RNA
<213> ORGANISM: Artificial Sequence
<220> FEATURE:
<223> OTHER INFORMATION: siRNA #27-8

<400> SEQUENCE: 9
auacgaaucu uccugauguu u                                            21

<210> SEQ ID NO 10
<211> LENGTH: 19
<212> TYPE: RNA
<213> ORGANISM: Artificial Sequence
<220> FEATURE:
<223> OTHER INFORMATION: dsiRNA #27-1

<400> SEQUENCE: 10
agacuauacc uaagccaau                                               19

<210> SEQ ID NO 11
<211> LENGTH: 19
<212> TYPE: RNA
<213> ORGANISM: Artificial Sequence
<220> FEATURE:
<223> OTHER INFORMATION: dsiRNA #27-2

<400> SEQUENCE: 11
aggagucaca gaaauaaug                                               19

<210> SEQ ID NO 12
<211> LENGTH: 21
<212> TYPE: RNA
<213> ORGANISM: Artificial Sequence
<220> FEATURE:
<223> OTHER INFORMATION: antisense
<220> FEATURE:
<221> NAME/KEY: misc_feature
<222> LOCATION: (1)..(1)
<223> OTHER INFORMATION: 5'-phospho

<400> SEQUENCE: 12
uuuaucguua gcacgcuucu u                                            21

<210> SEQ ID NO 13
<211> LENGTH: 21
<212> TYPE: RNA
<213> ORGANISM: Artificial Sequence
<220> FEATURE:
<223> OTHER INFORMATION: antisense
<220> FEATURE:
<221> NAME/KEY: misc_feature
<222> LOCATION: (1)..(1)
<223> OTHER INFORMATION: 5'-phospho

<400> SEQUENCE: 13
uaacugccaa cauccuucuu u                                            21
```

```
<210> SEQ ID NO 14
<211> LENGTH: 21
<212> TYPE: RNA
<213> ORGANISM: Artificial Sequence
<220> FEATURE:
<223> OTHER INFORMATION: #7 sense

<400> SEQUENCE: 14
ggacuggaau gcagcaaagu u                                          21

<210> SEQ ID NO 15
<211> LENGTH: 21
<212> TYPE: RNA
<213> ORGANISM: Artificial Sequence
<220> FEATURE:
<223> OTHER INFORMATION: antisense
<220> FEATURE:
<221> NAME/KEY: misc_feature
<222> LOCATION: (1)..(1)
<223> OTHER INFORMATION: 5'-phospho

<400> SEQUENCE: 15
cuuugcugca uuccaguccu u                                          21

<210> SEQ ID NO 16
<211> LENGTH: 21
<212> TYPE: RNA
<213> ORGANISM: Artificial Sequence
<220> FEATURE:
<223> OTHER INFORMATION: antisense
<220> FEATURE:
<221> NAME/KEY: misc_feature
<222> LOCATION: (1)..(1)
<223> OTHER INFORMATION: 5'-phospho

<400> SEQUENCE: 16
acaucaggaa gauucguauu u                                          21

<210> SEQ ID NO 17
<211> LENGTH: 21
<212> TYPE: DNA
<213> ORGANISM: Artificial Sequence
<220> FEATURE:
<223> OTHER INFORMATION: ApoA1 forward primer

<400> SEQUENCE: 17
gacctccacc ttcagcaagc t                                          21

<210> SEQ ID NO 18
<211> LENGTH: 22
<212> TYPE: DNA
<213> ORGANISM: Artificial Sequence
<220> FEATURE:
<223> OTHER INFORMATION: ApoA1 reverse primer

<400> SEQUENCE: 18 cctttttccag gttatcccag aa                                        22

<210> SEQ ID NO 19
<211> LENGTH: 22
<212> TYPE: DNA
<213> ORGANISM: Artificial Sequence
<220> FEATURE:
<223> OTHER INFORMATION: ApoA1 probe

<400> SEQUENCE: 19
agctcggccc tgtgacccag ga                                         22
```

```
<210> SEQ ID NO 20
<211> LENGTH: 24
<212> TYPE: DNA
<213> ORGANISM: Artificial Sequence
<220> FEATURE:
<223> OTHER INFORMATION: NRIP1 forward primer

<400> SEQUENCE: 20
tgctacagac ctatgtgtta ggaa                                              24

<210> SEQ ID NO 21
<211> LENGTH: 22
<212> TYPE: DNA
<213> ORGANISM: Artificial Sequence
<220> FEATURE:
<223> OTHER INFORMATION: NRIP1 reverse primer

<400> SEQUENCE: 21
cagtgctgat caacttctac gc                                                22

<210> SEQ ID NO 22
<211> LENGTH: 8
<212> TYPE: DNA
<213> ORGANISM: Artificial Sequence
<220> FEATURE:
<223> OTHER INFORMATION: NRIP1 probe

<400> SEQUENCE: 22 ctcctcct                                                                 8

<210> SEQ ID NO 23
<211> LENGTH: 27
<212> TYPE: RNA
<213> ORGANISM: Artificial Sequence
<220> FEATURE:
<223> OTHER INFORMATION: antisense

<400> SEQUENCE: 23
ccauuucauu auuucuguga cuccugu                                           27

<210> SEQ ID NO 24
<211> LENGTH: 25
<212> TYPE: RNA
<213> ORGANISM: Artificial Sequence
<220> FEATURE:
<223> OTHER INFORMATION: dsiRNAi#3

<400> SEQUENCE: 24
agcuaacaaa uacugcaucu aacca                                             25

<210> SEQ ID NO 25
<211> LENGTH: 27
<212> TYPE: RNA
<213> ORGANISM: Artificial Sequence
<220> FEATURE:
<223> OTHER INFORMATION: antisense

<400> SEQUENCE: 25
ugguuagaug caguauuugu uagcuuu                                           27
```

NRIP1 REGULATION OF APOLIPOPROTEIN A1

This application claims the benefit of U.S. provisional patent application No. 61/139,842; filed Dec. 22, 2008, which is herein incorporated by reference in its entirety.

FIELD OF THE INVENTION

The invention relates to methods for identifying therapeutic agents using nuclear receptor-interacting protein 1 (NRIP1) as a target.

BACKGROUND

A factor leading to development of vascular disease, a leading cause of death in industrialized nations, is elevated serum cholesterol. It is estimated that 19% of Americans between the ages of 20 and 74 years of age have high serum cholesterol. Blood cholesterol levels correlate to a risk of developing atherosclerosis and coronary heart disease, which creates an increased danger of heart attacks and strokes.

Due to the insolubility of cholesterol, blood transports cholesterol in a modified form of lipoproteins. Two primary forms of the lipoproteins include low-density lipoprotein (LDL), also known as "bad" cholesterol, and high-density lipoprotein (HDL), also known as "good" cholesterol. HDL cholesterol is beneficial largely because of its ability to perform reverse cholesterol transport, i.e. to scavenge excess cholesterol from arteries and deposit it in the liver for clearance through biliary excretion. See Zannis et al., *J Mol. Med.* 84(4):276-94 (2006), Lewis et al., *Circ Res.* 96(12):1221-32 (2005) and Tall et al., *Arterioscler. Thromb. Vasc. Biol.* 20(5): 1185-8 (2000). HDL also exhibits other anti-inflammatory and antioxidant properties. See Barter et al., *Circ Res.* 95(8): 764-72 (2004).

HDL is the smallest (7.0-12 nm diameter) and densest of the plasma lipoproteins. It consists of a hydrophobic core composed mainly of cholesteryl esters plus a small amount of triglyceride (TG) and unesterified cholesterol surrounded by a surface monolayer of phospholipids, unesterified cholesterol and apolipoproteins. The main HDL apolipoproteins (apo) are apoAI and apoAII. See Zannis et al., *J Mol. Med.* 84(4):276-94 (2006) and Lewis et al., *Circ Res.* 96(12):1221-32 (2005).

There are currently no drugs on the market that act directly on the reverse cholesterol pathway. See Ashen et al., *N Engl J. Med.* 353(12):1252-60 (2005). Pathways targeted by industry to increase HDL have been to increase synthesis and secretion of apoA1, and/or to decrease HDL catabolism. Several known agents called fibrates (e.g. Gemfibrozil) increase HDLc levels by acting on the liver. See Linsel-Nitschke et al., *Nat Rev Drug Discov.* 4(3): 193-205 (2005).

NRIP1, (Nuclear Receptor Interacting Protein 1, also known as RIP140), is a to corepressor that can inhibit the transcriptional activity of a number of nuclear receptors that influence such diverse processes as muscle metabolism, adipocyte and hepatocyte function, and reproduction. See, e.g., White et al., *FEBS Lett.* 582:39-45 (2008); Augereau et al., *J. Steroid Biochem. & Mol. Biol.* 102:51-59 (2006).

SUMMARY OF THE INVENTION

The present invention relates to findings regarding the role of NRIP1 in increasing apolipoprotein A1 (apoA1)) production.

Accordingly, the invention is directed to methods for increasing apolipoprotein A1 production in a cell or in a subject by inhibiting NRIP1 expression or activity. In some cases, NRIP1 expression is inhibited by a mechanism that involves RNA inhibition (RNAi) (e.g. siRNA) or other mechanism related to the use of a nucleic acid (e.g., an antisense nucleic acid that is targeted to NRIP1).

Provided herein is a method for identifying a candidate agent that increases transcription or production of apolipoprotein A1 (apoA1) comprising providing a sample comprising an NRIP1 polypeptide or a nucleic acid encoding the polypeptide, contacting the sample with a candidate agent under conditions in which the polypeptide is active, the nucleic acid is expressed, or both, and evaluating expression or activity of the NRIP1 polypeptide in the sample, wherein a decrease in NRIP1 polypeptide expression or activity as compared to a control sample indicates that the candidate agent increases transcription or production of apoA1 or antagonizes NRIP1 expression or activity. The method can be performed in a cell-based or cell-free assay. In certain embodiments the activity of NRIP1 can be evaluated by determining the level of interaction of NRIP1 with a second polypeptide such as PPAR. In preferred embodiments, the PPAR is PPARalpha, PPARdelta, or PPARgamma.

In certain embodiments, the methods are for identifying an RNAi molecule that inhibits expression of NRIP1 or that increases production of apoA1 comprising contacting a nucleic acid sense strand encoding NRIP1 with a candidate agent which is an RNA or DNA molecule and determining if the candidate agent hybridizes to the sense strand, wherein the candidate agent is identified as an RNAi molecule that inhibits expression of NRIP1 if said agent hybridizes to the sense strand. In alternate embodiments, the methods are for identifying an RNAi molecule that inhibits expression of NRIP1 or that increases production of apoA1 comprising contacting an mRNA encoding NRIP1 in a cell with a candidate agent which is an RNA or DNA molecule and determining if expression of NRIP1 in the cell decreases, wherein the candidate agent is identified as an RNAi molecule that inhibits expression of NRIP1 if said expression is observed to decrease.

In certain embodiments, the claimed methods for identifying an agent that increases transcription or production of apoA1 or that antagonizes NRIP1 activity comprises contacting an NRIP1 polypeptide with a candidate agent and determining if said agent binds to said NRIP1, wherein the candidate agent is identified as an agent that increases transcription or production of apoA1 or that antagonizes NRIP1 expression if said binding is observed.

In other embodiments, the methods for identifying an agent that increases transcription or production of apolipoprotein A1 (apoA1) or that antagonizes NRIP1 activity; comprises incubating a mixture comprising NRIP1 polypeptide that is labeled with a FET donor label or FET acceptor label and a second polypeptide binding partner that binds to NRIP1 that is labeled with the other label; under conditions which allow association between the polypeptides, in the presence of a candidate agent; wherein the donor and acceptor are chosen such that when the NRIP1 binds to the second polypeptide binding partner, the donor and the acceptor are brought into interacting proximity, producing a detectable luminescence lifetime change in the photoluminescence lifetime of the donor; and exposing the sample to an exciting amount of radiation, detecting the resulting emission; and calculating the apparent luminescence lifetime of the donor to quantify binding of the NRIP1 polypeptide to the binding partner polypeptide; wherein the candidate agent is identified as an agent that increases transcription or production of apolipoprotein A1 (apoA1) or that antagonizes NRIP1 activity if fluorescence by the donor occurs at a lower level than that observed in the absence of said candidate agent.

In other embodiments, the claimed methods for identifying an agent that increases transcription or production of apolipoprotein A1 (apoA1)) or that antagonizes NRIP1 activity comprises contacting NRIP1 polypeptide with a polypeptide binding partner in the presence of a candidate agent wherein the agent is identified as an agent that increases transcription or production of apolipoprotein A1 (apoA1)) or that antagonizes NRIP1 activity if less binding between NRIP1 and the polypeptide binding partner is observed in the presence of the candidate agent than in the absence of the candidate agent.

In certain embodiments, the candidate agent can comprise a polynucleotide, a polypeptide, a small non-nucleic acid organic molecule, a small inorganic molecule, or an antibody. In other embodiments, the candidate agent can comprise an antisense oligonucleotide, an inhibitory RNA, or a ribozyme. The candidate agent can be an RNA molecule or a DNA molecule.

The method can further comprise determining whether apoA1 production is modulated in the presence of the test compound, preferably using an antibody. In other embodiments, the activity of NRIP1 can be evaluated by determining the level of interaction of NRIP1 with a polypeptide binding partner, such as peroxisome proliferator-activated receptor (PPAR). Preferably, the peroxisome proliferator-activated receptor (PPAR) is PPAR alpha, PPARdelta or PPARgamma.

The invention also provides a method for increasing apoA1 production in a cell comprising contacting a cell with an agent that inhibits expression or activity of an NRIP1 polypeptide.

In preferred embodiments, the agent can comprise a polynucleotide, a polypeptide, a DNA molecule, an RNA molecule, a small non-nucleic acid organic molecule, a small inorganic molecule, or an antibody. In other embodiments, the agent can comprise an antisense oligonucleotide, an inhibitory RNA, or a ribozyme. In other embodiments the agent can comprise a small inhibitory RNA (siRNA). Preferably, the siRNA targets a sequence selected from SEQ ID NOS: 7, 8 or 9.

In certain embodiments, the agent inhibits transcription of NRIP1 mRNA or decreases binding of NRIP1 polypeptide to a polypeptide binding partner. Preferably, the polypeptide binding partner is a peroxisome proliferator-activated receptor (PPAR), such as PPAR alpha, PPARdelta or PPARgamma.

Further provided is a method for treating a subject at risk for or suffering from a disorder related to lipid metabolism or at risk for or suffering from coronary heart disease comprising administering to the subject an agent that decreases expression or activity of an NRIP1 polypeptide in an amount sufficient to increase apoA1 transcription or production in a cell of the subject, thereby increasing apoA1 production in the subject.

In preferred embodiments, the agent can comprise a polynucleotide, a polypeptide, a small non-nucleic acid organic molecule, a small inorganic molecule, or an antibody. In other embodiments, the test compound can comprise an antisense oligonucleotide, an inhibitory RNA, or a ribozyme. In further embodiments, the agent comprises a small inhibitory RNA (siRNA). Preferably, the siRNA targets a sequence selected from SEQ ID NOS: 7, 8 or 9.

The method may further comprise administration of one or more additional therapeutic agents that increase high density lipoproteins (HDL) expression in the subject or that decrease low density lipoproteins (LDL) in the subject. In preferred embodiments, the further therapeutic agent is a cholesterol-lowering drug. Preferably, the therapeutic agent is ezetimibe. In further embodiments, the further therapeutic agent is an HMG-CoA reductase inhibitor. Preferably, the HMG-CoA reductase inhibitor is selected from the group consisting of lovastatin, simvastatin, pravastatin, fluvastatin, atorvastatin, itavastatin, ZD-4522 and rivastatin.

DETAILED DESCRIPTION OF THE INVENTION

Figure 1:
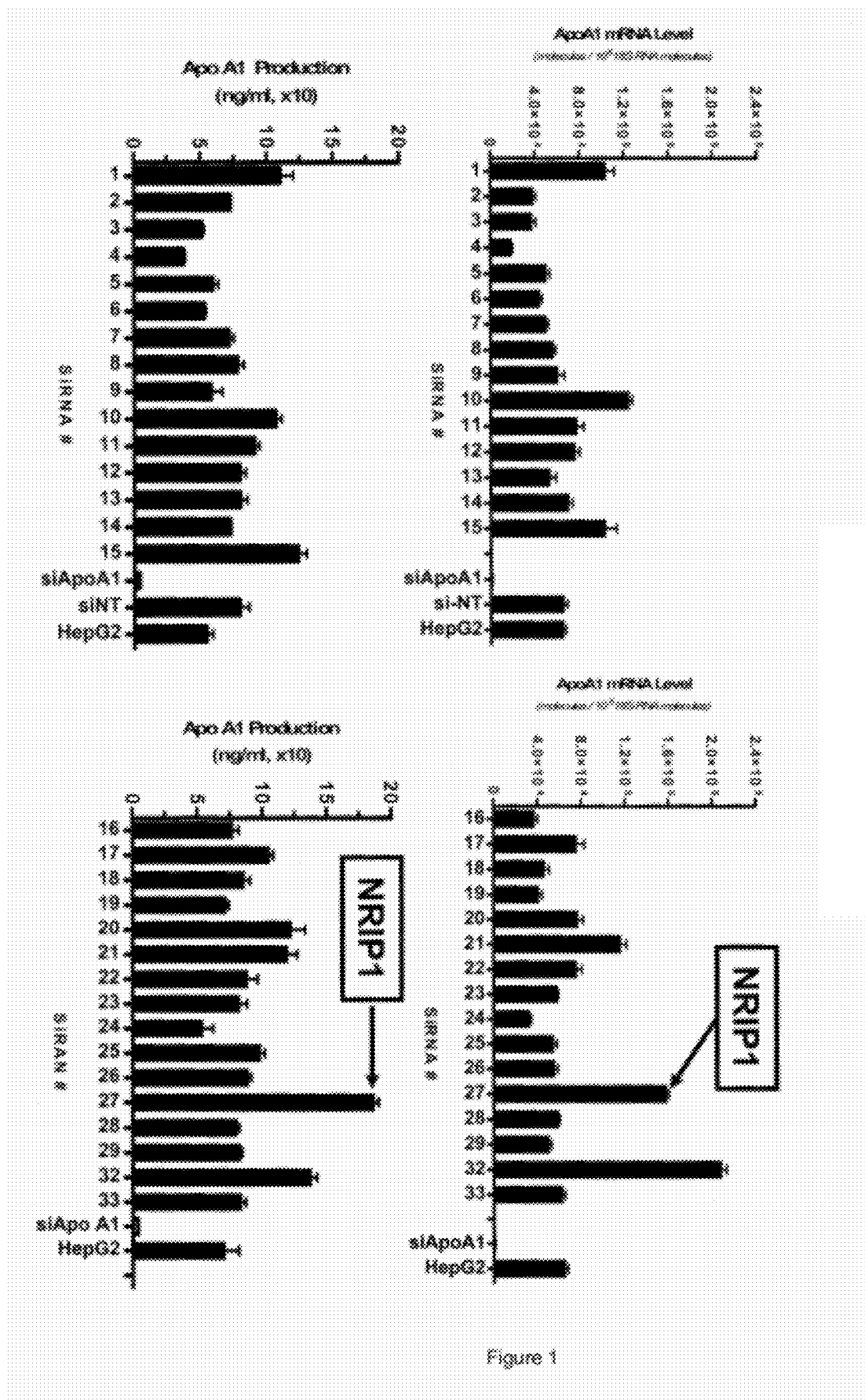
FIG. 1 is a bar graph illustrating the effect of RNAi functional knockdown of various transcription modulators on apoA1 mRNA level and secreted protein production in HepG2 cells.

All publications cited herein are incorporated by reference in their entirety.

It has been found that NRIP1 plays a role in the regulation of apoA1 transcription and selectively increases apoA1 protein production in cells of the liver and intestine. Decreasing the level of NRIP1 expression increases apoA1 transcription and production. Administration of compounds that decrease NRIP1 expression or activity increases production of apoA1 and triggers synthesis of nascent-HDL particles in the liver and small intestine. Thus, compounds that decrease NRIP1 expression or activity are useful as therapeutics for treating disorders in which it is desirable to increase expression or activity of genes related to lipid metabolism (dislipidemia), for example, atherosclerosis, coronary heart disease, hyperlipidemia, hycholesterolemia, arteriosclerosis. Furthermore, NRIP1 interacts with several different PPARs. Compounds that decrease the interaction between NRIP1 and a ligand such as a PPAR (Peroxisome Proliferator-Activated Receptor; e.g., PPARalpha, PPARdelta, and PPARgamma) are useful for treating disorders mediated by NRIP1, e.g., dislipidemia or coronary heart disease.

The present invention includes treating "subjects" and "patients" and the like which are mammals such as humans, canines, mice, rats, cats, horses, monkeys and other primates, hamsters and rabbits.

NRIP1 and PPAR

NRIP1, also known as RIP140, is a nuclear protein containing approximately 1158 amino acids, with a size of approximately 128 kDa. NRIP1 binds to nuclear receptors via LXXLL (SEQ ID NO: 1) motifs, wherein L is leucine and X is any amino acid (Heery et al., Nature 387(6634):733-6 (1997)). Ten LXXLL (SEQ ID NO: 1) motifs are found in the NRIP1 sequence. NRIP1 also interacts with histone deacetylases and with C-terminal binding protein (CTBP) via a PXDLS ((SEQ ID NO: 2)) motif found in the NRIP1 sequence.

Thus, "activities" of NRIP1 include binding to various "binding partner" or "target molecule" polypeptides such as PPAR, histone deacetylases, CTBP or one or more nuclear receptors as well as modulation of apoA1 expression (transcription or ultimately, protein production). Methods described herein which determine NRIP1 activity include any which determine the ability of NRIP1 to do any of the foregoing activities. Thus, an "inhibitor" or NRIP1 may inhibit any of these activities to any detectable degree.

A human NRIP1 nucleotide sequence is listed in GenBank under Accession No. NM_003489. The corresponding human amino acid sequence is found under Accession No. NP_003480. The nucleotide sequence of the chromosomal region containing the entire human NRIP1 gene can be found in GenBank under Accession No. AF248484. A murine NRIP1 nucleotide sequence can be found in GenBank under Genbank Accession No. NM_173440. The corresponding murine amino acid sequence is found under Accession No. NP_775616.

In an embodiment of the invention, human NRIP1 polynucleotide comprises the nucleotide sequence:

```
                                                          (SEQ ID NO: 3)
        atgactcatg gagaagagct tggctctgat gtgcaccagg attctattgt tttaacttac    60
ctagaaggat tactaatgca tcaggcagca gggggatcag gtactgccgt tgacaaaaag   120
tctgctgggc ataatgaaga ggatcagaac tttaacattt ctggcagtgc atttcccacc   180
tgtcaaaagt atggtccagt tctcaataca catacatatc aggggtctgg catgctgcac   240
ctcaaaaaag ccagactgtt gcagtcttct gaggactgga atgcagcaaa gcggaagagg   300
ctgtctgatt ctatcatgaa tttaaacgta aagaaggaag ctttgctagc tggcatggtt   360
gacagtgtgc ctaaaggcaa acaggatagc acattactgg cctctttgct tcagtcattc   420
agctctaggc tgcagactgt tgctctgtca caacaaatca ggcagagcct caaggagcaa   480
ggatatgccc tcagtcatga ttctttaaaa gtggagaagg atttaaggtg ctatggtgtt   540
gcatcaagtc acttaaaaac tttgttgaag aaaagtaaag ttaaagatca aaagcctgat   600
acgaatcttc ctgatgtgac taaaaccttc atcagagata ggtttgcaga gtctcctcat   660
catgttggac aaagtggaac aaaggtcatg agtgaaccgt tgtcatgtgc tgcaagatta   720
caggctgttg caagcatggt ggaaaaaagg gctagtcctg ccacctcacc taaacctagt   780
gttgcttgta gccagttagc attacttctg tcaagcgaag cccatttgca gcagtattct   840
cgagaacacg ctttaaaaac gcaaaatgca aatcaagcag caagtgaaag acttgctgct   900
atggccagat tgcaagaaaa tggccagaag gatgttggca gttaccagct cccaaaagga   960
atgtcaagcc atcttaatgg tcaggcaaga acatcatcaa gcaaactgat ggctagcaaa  1020
agtagtgcta cagtgtttca aaatccaatg ggtatcattc cttcttcccc taaaaatgca  1080
ggttataaga actcactgga aagaaacaat ataaaacaag ctgctaacaa tagtttgctt  1140
ttacatcttc ttaaaagcca gactatacct aagccaatga atggacacag tcacagtgag  1200
agaggaagca tttttgagga aagtagtaca cctacaacta ttgatgaata ttcagataac  1260
aatcctagtt ttacagatga cagcagtggt gatgaaagtt cttattccaa ctgtgttccc  1320
atagacttgt cttgcaaaca ccgaactgaa aaatcagaat ctgaccaacc tgtttccctg  1380
gataacttca ctcaatcctt gctaaacact tgggatccaa aagtcccaga tgtagatatc  1440
aaagaagatc aagatacctc aaagaattct aagctaaact cacaccagaa agtaacactt  1500
cttcaattgc tacttggcca taagaatgaa gaaaatgtag aaaaaaacac cagccctcag  1560
ggagtacaca atgatgtgag caagttcaat acacaaaatt atgcaaggac ttctgtgata  1620
gaaagcccca gtacaaatcg gactactcca gtgagcactc caccttttact tacatcaagc  1680 aaagcagggt ctcccatcaa tctctctcaa cactctctgg tcatcaaatg gaattcccca  1740
ccatatgtct gcagtactca gtctgaaaag ctaacaaata ctgcatctaa ccactcaatg  1800
```

```
gaccttacaa aaagcaaaga cccaccagga gagaaaccag cccaaaatga aggtgcacag   1860
aactctgcaa cgtttagtgc cagtaagctg ttacaaaatt tagcacaatg tggaatgcag   1920
tcatccatgt cagtggaaga gcagagaccc agcaaacagc tgttaactgg aaacacagat   1980
aaaccgatag gtatgattga tagattaaat agcccttgc tctcaaataa aacaaatgca   2040
gttgaagaaa ataaagcatt tagtagtcaa ccaacaggtc ctgaaccagg ctttctggt   2100 tctgaaatag aaaatctgct tgaaagacgt actgtcctcc agttgctcct ggggaacccc   2160
aacaaaggga agagtgaaaa aaaagagaaa actcccttaa gagatgaaag tactcaggaa   2220
cactcagaga gagctttaag tgaacaaata ctgatggtga aaataaaatc tgagccttgt   2280
gatgacttac aaattcctaa cacaaatgtg cacttgagcc atgatgctaa gagtgcccca   2340
ttcttgggta tggctcctgc tgtgcagaga agcgcacctg ccttaccagt gtccgaagac   2400
tttaaatcgg agcctgtttc acctcaggat ttttcttct ccaagaatgg tctgctaagt   2460
cgattgctaa gacaaaatca agatagttac ctggcagatg attcagacag gagtcacaga   2520
aataatgaaa tggcacttct agaatcaaag aatctttgca tggtccctaa gaaaaggaag   2580
ctttatactg agccattaga aaatccattt aaaaagatga aaacaacat tgttgatgct   2640 gcaaacaatc acagtgcccc agaagtactg tatgggtcct tgcttaacca ggaagagctg   2700
aaatttagca gaaatgatct tgaatttaaa tatcctgctg gtcatggctc agccagcgaa   2760
agtgaacaca ggagttgggc cagagagagc aaaagcttta atgttctgaa acagctgctt   2820
ctctcagaaa actgtgtgcg agatttgtcc ccgcacagaa gtaactctgt ggctgacagt   2880 aaaagaaag gacacaaaaa taatgtgacc aacagcaaac ctgaatttag catttcttct   2940
ttaaatggac tgatgtacag ttccactcag cccagcagtt gcatggataa caggacattt   3000
tcatacccag gtgtagtaaa aactcctgtg agtcctactt tccctgagca cttgggctgt   3060
gcagggtcta gaccagaatc tgggctttg aatgggtgtt ccatgcccag tgagaaagga   3120
cccattaagt gggttatcac tgatgcggag aagaatgagt atgaaaaaga ctctccaaga   3180
ttgaccaaaa ccaacccaat actatattac atgcttcaaa aaggaggcaa ttctgttacc   3240
agtcgagaaa cacaagacaa ggacatttgg agggaggctt catctgctga aagtgtctca   3300
caggtcacag ccaaagaaga gttacttcct actgcagaaa cgaaagcttc tttcttaat   3360 ttaagaagcc cttacaatag ccatatggga aataatgctt ctcgcccaca cagcgcaaat   3420
ggagaagttt atggacttct gggaagcgtg ctaacgataa agaaagaatc agaataa       3477
```

In an embodiment of the invention, human NRIP1 polypeptide comprises the amino acid sequence:

```
                                                  (SEQ ID NO: 4)
MLHGEELGSD VHQDSIVLLY LEGLLMHQAA GGSGLAVDKK SAGHNEEDQN FNISGSAFPL    60

CQSNGPVLNL HLYQGSGMLH LKKARLLQSS EDWNAAKRKR LSDSIMNLNV KKEALLAGMV   120

DSVPKGKQDS LLLASLLQSF SSRLQLVALS QQIRQSLKEQ GYALSHDSLK VEKDLRCYGV   180

ASSHLKLLLK KSKVKDQKPD LNLPDVLKNL IRDRFAESPH HVGQSGLKVM SEPLSCAARL   240

QAVASMVEKR ASPALSPKPS VACSQLALLL SSEAHLQQYS REHALKLQNA NQAASERLAA   300

MARLQENGQK DVGSYQLPKG MSSHLNGQAR LSSSKLMASK SSALVFQNPM GIIPSSPKNA   360

GYKNSLERNN IKQAANNSLL LHLLKSQLIP KPMNGHSHSE RGSIFEESSL PLLIDEYSDN   420

NPSFLDDSSG DESSYSNCVP IDLSCKHRLE KSESDQPVSL DNFLQSLLNL WDPKVPDVDI   480

KEDQDLSKNS KLNSHQKVLL LQLLLGHKNE ENVEKNLSPQ GVHNDVSKEN LQNYARLSVI   540
```

```
ESPSLNRLLP VSLPPLLLSS KAGSPINLSQ HSLVIKWNSP PYVCSLQSEK LLNLASNHSM    600

DLLKSKDPPG EKPAQNEGAQ NSALFSASKL LQNLAQCGMQ SSMSVEEQRP SKQLLLGNLD    660

KPIGMIDRLN SPLLSNKLNA VEENKAFSSQ PLGPEPGLSG SEIENLLERR LVLQLLLGNP    720

NKGKSEKKEK LPLRDESLQE HSERALSEQI LMVKIKSEPC DDLQIPNLNV HLSHDAKSAP    780

FLGMAPAVQR SAPALPVSED FKSEPVSPQD FSFSKNGLLS RLLRQNQDSY LADDSDRSHR    840

NNEMALLESK NLCMVPKKRK LYLEPLENPF KKMKNNIVDA ANNHSAPEVL YGSLLNQEEL    900

KFSRNDLEFK YPAGHGSASE SEHRSWARES KSFNVLKQLL LSENCVRDLS PHRSNSVADS    960

KKKGHKNNVL NSKPEFSISS LNGLMYSSLQ PSSCMDNRLF SYPGVVKLPV SPLFPEHLGC   1020

AGSRPESGLL NGCSMPSEKG PIKWVILDAE KNEYEKDSPR LLKLNPILYY MLQKGGNSVL   1080

SRELQDKDIW REASSAESVS QVLAKEELLP LAELKASFFN LRSPYNSHMG NNASRPHSAN   1140

GEVYGLLGSV LLIKKESE                                                1158
```

In an embodiment of the invention, mouse NRIP1 polynucleotide comprises the nucleotide sequence:

```
                                                       (SEQ ID NO: 5)
atgactcatg gagaagagct tggctctgat gtgcatcagg attctattgt cttaacttac     60
ctcgaagggt tactaatgca tcaggcagca gggggatcag gcactgccat taacaaaaag    120
tctgctggcc acaaagagga agaccagaac tttaacctct cgggcagtgc gtttccctcc    180
tgtcaaagca atggtcccac tgtcagtacc cagacgtacc agggatctgg catgctgcac    240
ctcaaaaaag ccagactgct gcagtcttcc gaggactgga acgcggcaaa gcggaagagg    300
ctgtctgatt ccatcgtgaa tttaaacgta agaaggaag cgtcgctggc tggcatggtt    360
gacagtgtgc ctaaaggcaa acaggatagc acattgctgg cctctttgct tcagtcattc    420
agctctaggc tgcagactgc tgctctgtca cagcagatta gacagagcct caaggagcag    480
ggatatgccc tcagtcacga gtctttaaaa gtggagaagg atttaaggtg ctatggcgtg    540
gcctcaagtc acttaaaaac tctgttgaag aaaagtaaaa ccaaggatca aaagtcaggt    600 cccacccctcc ctgacgtgac tccaaaacctt atcagagata gctttgttga gtcatcccat    660
cccgcagtgg gacaaagcgg gacaaaggtc atgagtgagc ccttgtcatg tgctgcaaga    720
ttacaggctg ttgccagcat ggtggagaaa agggcgagtc ccgctgcctc cccaaagcct    780
agtgttgcct gcagccagtt ggcgctgctc ctgtccagcg aggcccacct gcagcagtac    840
tctcgggaac atgctctaaa aacgcagaac gcacatcagg tggcaagcga aagacttgca    900
gccatggcca gattgcaaga gaacgggcag aaggacgtgg gcagttcgca gctctccaaa    960
ggggcgcccg gccaCctcaa cgggcaggcc agagcactgc cggcaagcaa actggtggcc   1020
aacaagaata acgctgccac ctttcagagt ccaatgggtg ttgtcccttc ctcccccaaa   1080
aacacgagct ataagaactc actggaaaga aacaacctaa agcaggctgc taaCaacagt   1140
ctgcttttgc atctcctcaa aagccagacc atacccacgc cgatgaacgg gcacagccag   1200
aacgagagag cgagcagttt tgagagtagc acgcccacca cgattgatga gtactccgat   1260
aacaacccga gctttacaga tgacagcagt ggagacgaaa gctcgtactc caattgcgtt   1320
cccatagacc tgtcttgcaa acaccggatc gaaaagccgg aagctgagcg gcccgtttcg   1380
ctggagaacc taacccagtc cttgttaaac acgtgggatc ccaagatccc cggcgttgac   1440 atcaagaag atcaagatac cCcaacaaat tccaagctga attcacacca gaaagtcact   1500
cttcttcagt tgccgctcgg ccacaaaagt gaagaaactg ttgaaaggaa cgccagccct   1560
```

-continued

```
caggacatcc aragtgatgg gaccaagttc agccctcaga attacacaag gacttctgtc   1620
atcgaaagcc ccagtaccaa caggactacc ccagtgagca ccccaccacc gcatacagcc   1680
agccaagcag agcctcccat caacctttcc cagcaccctc tggtcatcaa gtggaattcc   1740
ccgccgtatg cctgcagtac tcccgcttcc aagctcacga acaccgcgcc tagccacctg   1800
atggacctca cgaaaggcaa agagtcccaa gccgagaaac cagccccgag tgaaggcgca   1860
caaaattccg ccacgtccag tgccagtaaa ctgttacaaa atttggctca gtgcggattg   1920
cagtcttccg ggccagggga agagcagaga ccctgcaaac agctgttaag tggaaaccca   1980
gacaaacctc tcggtctgat tgatagatta aacagccctc tgctctcaaa taaaaccaat   2040
gcggctgaag agagcaaagc cttcagcagt cagcctgccg ggcctgagcc gggacttcct   2100
ggttgtgaga tagaaaatct cttggaaaga cggactgtcc ttcagttgct cctgggaaac   2160
tccagcaaag ggaagaatga aagaaagag aaaaccccg cacgagacga ggctcctcag   2220
gagcattcgg agagggctgc aaatgaacag atactcatgg tgaagaccaa acccgagcct   2280
tgtgacgact ccagacccca aacacaaac ctgcccttaa accacgatgc aagagcgcc    2340
ccccccttag gtgtgactcc cgccatccac aggagcacag cggccttacc agtgtcggag   2400
gactctaaat ccgagcctgc ttcacctcag gacttctctt tctcaaagaa cgggctgttg   2460
agtcgcCtgc tgagacagaa tcaagagagt tacccggcag atgagcagga caagagccac   2520
agaaacagtg agctgccaac cctggagtcg aagaacatct gcatggtccc gaagaaaagg   2580
aagctgtata cggaaccact ggagaatcca tttaaaaaga tgaaaaatac tgccgtagat   2640
actgccaatc atcacagcgg cccggaagta ctctacgggt cgttgcttca tcaggaagag   2700
ctgaagttta gcaggaatga gctcgattat aaatacctg ctgggcatag ttcagccagc    2760
gatggtgacc acaggagttg ggccagagag agcaaaagct tcaatgttct caagcagctg   2820
ctgctctccg agaactgtgt gcgagatctg tccccacaca ggagtgactc tgtccccgac   2880
acgaaaaaga aaggacacaa aaacaacgcg cccggcagca aacctgaatt cggcatttct   2940
tctttaaatg gactgatgta tagttccccg cagcctggca gttgtgtgac ggatcatagg   3000
acatttcat acccgggaat ggtaaagacc cctctgagcc ctcctttccc agagcacttg    3060
ggctgtgtgg ggtccagacc agaacctggg cttttgaatg gatgttccgt gcccggtgag   3120
aagggaccca ttaagtgggt catcgcagat atggataaga atgaatacga aaaagactct   3180
ccaagactga ccaaaactaa tccgatcctc tattacatgc tccagaaggg aggggcaat    3240
tctgttacca cacaagaaac ccaggacaaa gacatctgga gggagcctgc gtcagccgag   3300
agtctctcac aggttacagt caaagaagag ctacttcccg ctgcagaaac taaagcttct   3360
ttctttaatc taagaagccc gtacaatagc catatgggaa ataatgcttc tcgcccacac   3420
agtacaaatg gagaagtgta tggacttctg ggaaacgcgc tcaccataaa aaaagagtca   3480
gaataa                                                              3486
```

In an embodiment of the invention, mouse NRIP1 polypeptide comprises the amino acid sequence:

```
                                                         (SEQ ID NO: 6)
MLHGEELGSD VHQDSIVLLY LEGLLMHQAA GGSGLAINKK SAGHKEEDQN FNLSGSAFPS    60

CQSNGPLVSL QLYQGSGMLH LKKARLLQSS EDWNAAKRKR LSDSIVNLNV KKEALLAGMV   120

DSVPKGKQDS LLLASLLQSF SSRLQLVALS QQIRQSLKEQ GYALSHESLK VEKDLRCYGV   180

ASSHLKLLLK KSKLKDQKSG PLLPDVLPNL IRDSFVESSH PAVGQSGLKV MSEPLSCAAR   240
```

```
LQAVASMVEK RASPAASPKP SVACSQLALL LSSEAHLQQY SREHALKLQN AHQVASERLA    300

AMARLQENGQ KDVGSSQLSK GVSGHLNGQA RALPASKLVA NKNNAALFQS PMGVVPSSPK    360

NLSYKNSLER NNLKQAANNS LLLHLLKSQL IPLPMNGHSQ NERASSFESS LPLLIDEYSD    420

NNPSFLDDSS GDESSYSNCV PIDLSCKHRI EKPEAERPVS LENLLQSLLN LWDPKIPGVD    480

IKEDQDLSLN SKLNSHQKVL LLQLLLGHKS EELVERNASP QDIHSDGLKF SPQNYLRLSV    540

IESPSLNRLL PVSLPPLYLA SQAESPINLS QHSLVIKWNS PPYACSLPAS KLLNLAPSHL    600

MDLLKGKESQ AEKPAPSEGA QNSALFSASK LLQNLAQCGL QSSGPGEEQR PCKQLLSGNP    660

DKPLGLIDRL NSPLLSNKLN AAEESKAFSS QPAGPEPGLP GCEIENLLER RLVLQLLLGN    720

SSKGKNEKKE KLPARDEAPQ EHSERAANEQ ILMVKIKSEP CDDFQLHNLN LPLNHDAKSA    780

PFLGVLPAIH RSLAALPVSE DFKSEPASPQ DFSFSKNGLL SRLLRQNQES YPADEQDKSH    840

RNSELPLLES KNICMVPKKR KLYLEPLENP FKKMKNLAVD LANHHSGPEV LYGSLLHQEE    900

LKFSRNELDY KYPAGHSSAS DGDHRSWARE SKSENVLKQL LLSENCVRDL SPHRSDSVPD    960

LKKKGHKNNA PGSKPEFGIS SLNGLMYSSP QPGSCVLDHR LFSYPGMVKL PLSPPFPEHL   1020

GCVGSRPEPG LLNGCSVPGE KGPIKWVIAD MDKNEYEKDS PRLLKLNPIL YYMLQKGGGN   1080

SVLLQELQDK DIWREPASAE SLSQVLVKEE LLPAAELKAS FFNLRSPYNS HMGNNASRPH   1140

SLNGEVYGLL GNALLIKKES E                                            1161
```

Embodiments of the invention include use of the foregoing NRIP1 polypeptides or polynucleotides. A number of NRIP1 homologs are known in the art. See White et al., *FEBS Lett.* 582:39-45 (2008). A biologically active NRIP1 or fragment thereof includes sequences that can be transfected into an NRIP1−/− cell and restore NRIP1 "activity" or which otherwise possess any of the foregoing "activities".

In some embodiments, NRIP1 activity can be determined by examining levels of NRIP1 binding to PPARs. PPAR sequences are known in the art, for example see Genbank accession nos. NP005027 (PPARalpha), Q03181 (PPARdelta), P37231 (PPARgamma).

Screening Assays

The methods described herein include methods (also referred to herein as "screening assays") for identifying modulators of NRIP1 expression or NRIP1 activity. Such modulators include, e.g., polypeptides, peptides, peptidomimetics, peptoids, small inorganic molecules, small non-nucleic acid organic molecules, nucleic acids (e.g., anti-sense nucleic acids, siRNA, oligonucleotides, synthetic oligonucleotides), carbohydrates, or other agents that bind to NRIP1 proteins, have a stimulatory or inhibitory effect on, for example, NRIP1 expression or NRIP1 activity, or have a stimulatory or inhibitory effect on, for example, the expression or activity of an NRIP1 substrate. Compounds thus identified can be used to modulate the activity of NRIP1 in a therapeutic protocol, to elaborate the biological function of a NRIP1, or to identify compounds that disrupt NRIP1 interactions (e.g., with a PPAR such as PPARalpha, PPARdelta, or PPARgamma).

In general, screening assays include assaying the effect of a candidate agent on expression or activity of an NRIP1 nucleic acid or polypeptide in a test sample (i.e., a sample containing the NRIP1 nucleic acid or polypeptide). Expression or activity in the presence of the candidate agents is compared to expression or activity in a control sample (i.e., a sample containing an NRIP1 polypeptide that was incubated under the same conditions, but without the candidate agent). A change in the expression or activity of the NRIP1 nucleic acid or polypeptide in the test sample compared to the control indicates that the candidate agent modulates expression or activity of the NRIP1 nucleic acid or polypeptide.

Compounds can be tested for their ability to modulate one or more NRIP1 mediated activities. For example, compounds that inhibit NRIP1 activity result in at least one of: increased apoA1 transcription or translation or decreased interaction between NRIP1 and a binding partner, such as PPAR or decreased transcription or translation of NRIP1. In some cases, a candidate agent is tested for its ability to directly affect NRIP1 expression or binding to an NRIP1 binding partner (e.g., by decreasing the amount of NRIP1 RNA in a cell, decreasing the amount of NRIP1 protein in a cell, or decreasing the repressor-associated binding of NRIP1) and then tested for its ability to modulate an activity associated with NRIP1 (e.g., increased apoA1 transcription or increased apoA1 protein production).

In one embodiment of the invention, assays are provided for screening candidate agents that bind to and inhibit NRIP1 polypeptide or a biologically active portion thereof in a cell in target tissues including liver and small intestine. In another embodiment, the assays are for screening candidate agents that bind to an NRIP1 or modulate the activity of an NRIP1 or a biologically active fragment thereof. Such compounds include those that disrupt the interaction between NRIP1 and a binding partner such as PPAR (e.g., PPARalpha, PPARdelta, or PPARgamma).

The candidate agents used in the methods can be obtained using any of the numerous approaches in the art including combinatorial library methods, including: biological libraries; peptoid libraries (libraries of molecules having the functionalities of peptides, but with a novel, non-peptide backbone which are resistant to enzymatic degradation but which nevertheless remain bioactive; e.g., Zuckermann et al., *J. Med. Chem.*, 37:2678-2685 (1994); spatially addressable parallel solid phase or solution phase libraries; synthetic library methods requiring deconvolution; the 'one-bead one-compound' library method; and synthetic library methods using affinity chromatography selection. The biological library and peptoid library approaches are limited to peptide libraries, while the other four approaches are applicable to peptide, non-peptide oligomer or small molecule libraries of compounds (Lam, *Anticancer Drug Des.*, 12:145 (1997)).

Examples of methods for the synthesis of molecular libraries can be found in the literature, for example in: DeWitt et al., *PNAS* 90:6909 (1993); Erb et al., *PNAS* 91:11422 (1994); Zuckermann et al., *J. Med. Chem.* 37:2678 (1994); Cho et al., *Science* 261:1303 (1993); Carrell et al., *Anqew. Chem. Int. Ed. Engl.* 33:2059, 1994; Carell et al., *Anqew. Chem. Int. Ed. Engl.*, 33:2061 (1994) and Gallop et al., *J. Med. Chem.*, 37:1233 (1994).

Libraries of compounds may be presented in solution (e.g., Houghten, *Bio/Techniques*, 13:412421 (1992), or on beads (Lam, *Nature* 354:82-84 (1991), chips (Fodor, *Nature* 364: 555-556 (1993)), bacteria (U.S. Pat. No. 5,223,409), spores (U.S. Pat. Nos. 5,571,698; 5,403,484; and 5,223,409), plasmids (Cull et al., *PNAS* 89:1865-1869 (1992) or phage (Scott and Smith, *Science* 249:386-390 (1990); Devlin, *Science* 249:404-406 (1990); Cwirla et al., *PNAS* 87:6378-6382 (1990); and Felici, *J. Mol. Biol.* 222:301-310 (1991).

A competitive binding assay within the scope of the invention includes a method for identifying a candidate agent that increases transcription or production of apolipoprotein A-1 (apoA1) or that antagonizes NRIP1 activity comprising contacting NRIP1 polypeptide with polypeptide binding partner (e.g., PPAR) in the presence of the candidate agent wherein the agent is identified as an agent that increases transcription or production of apolipoprotein A-1 (apoA1) or that antagonizes NRIP1 activity if less binding between NRIP1 and the polypeptide binding partner is observed in the presence of the candidate agent than in the absence of the candidate agent. Again, if the candidate agent inhibits binding with NRIP1, then this would be a basis on which to further examine the agent to confirm that it exhibits NRIP1 antagonist activity.

In one embodiment of the invention, a cell-based assay is employed in which a cell that expresses an NRIP1 protein or biologically active fragment thereof is contacted with a candidate agent. The ability of the candidate agents to modulate NRIP1 expression or activity is then determined, e.g., by monitoring apoA1 transcription or apoA1 protein production. The cell, for example, can be a yeast cell or a cell of mammalian origin, e.g., rat, mouse, or human, e.g., liver or small intestine, e.g., HepG2 cells. If the expression level of apoA1 increases, then the candidate agent is identified as an inhibitor of NRIP1 or an agonist of apoA1 expression.

The ability of the candidate agents to modulate NRIP1 binding to an NRIP1 polypeptide binding partner (e.g., PPAR), or simply to bind to NRIP1 can also be evaluated. This can be accomplished, for example, by coupling the binding partner with a radioisotope or enzymatic label such that binding of the binding partner to NRIP1 can be determined by detecting the labeled binding partner in a complex with NRIP1, e.g., wherein the labeled NRIP1/binding partner complexes are detected. Alternatively, NRIP1 can be coupled with a radioisotope or enzymatic label to monitor the ability of a candidate agent to modulate NRIP1 binding to an NRIP1 binding partner in a complex. For example, compounds (e.g., NRIP1 binding partner s) can be labeled with $^{125}I$, $^{35}S$, $^{14}C$, or $^{3}H$, either directly or indirectly, and the radioisotope detected by direct counting of radioemission or by scintillation counting. Alternatively, compounds can be enzymatically labeled with, for example, horseradish peroxidase, alkaline phosphatase, or luciferase, and the enzymatic label detected by determination of conversion of an appropriate binding partner to product. In an alternative embodiment of the invention, neither NRIP1 nor the binding partner is labeled and the NRIP1/binding partner complex is detected directly by methods known in the art.

The ability of a compound (e.g., an NRIP1 binding partner) to interact with NRIP1 with or without the labeling of any of the interactants can be evaluated. For example, a microphysiometer can be used to detect the interaction of a compound with NRIP1 without the labeling of either the compound or the NRIP1 (McConnell et al., *Science* 257:1906-1912 (1992)). As used herein, a "microphysiometer" (e.g., Cytosensor.RTM.) is an analytical instrument that measures the rate at which a cell acidifies its environment using a light-addressable potentiometric sensor (LAPS). Changes in this acidification rate can be used as an indicator of the interaction between a compound and NRIP1.

A basic binding assay within the scope of the present invention includes a method for identifying a candidate agent that increases transcription or production of apolipoprotein A-1 (apoA1) or that antagonizes NRIP1 activity comprising contacting NRIP1 polypeptide with a candidate agent and determining if said agent binds to said NRIP1 or a biologically active portion thereof wherein the candidate agent is identified as an agent that increases transcription or production of apolipoprotein A-1 (apoA1) or that antagonizes NRIP1 expression or activity if said binding is observed. If the candidate agent binds to NRIP1, then this would be a basis on which to further examine the agent to confirm that it exhibits NRIP1 antagonist activity. In an embodiment of the invention, this assay is a cell-free assay is provided in which an NRIP1 protein or biologically active portion thereof is contacted with a candidate agent and the ability of the candidate agent to bind to the NRIP1 protein or biologically active portion thereof is evaluated. Interaction between NRIP1 and a candidate agent may indicate that the candidate agent is an inhibitor of NRIP1. Further tests may be used to determine if the binding leads to antagonism of NRIP1. Cell-free assays include preparing a reaction mixture of NRIP1 and the candidate agent under conditions and for a time sufficient to allow the two components to interact and bind, thus forming a complex. The reaction mixture is then analyzed to detect any presence of the complex.

The interaction between two molecules, such as NRIP1 and a PPAR can be detected using fluorescence energy transfer (FET) (see, for example, Lakowicz et al., U.S. Pat. No. 5,631,169; Stavrianopoulos et al., U.S. Pat. No. 4,868,103). A fluorophore label on the first, 'donor' molecule (e.g., NRIP1 or PPAR) is selected such that its emitted fluorescent energy will be absorbed by a fluorescent label on a second, 'acceptor' molecule (e.g., NRIP1 or PPAR), which in turn is able to fluoresce due to the absorbed energy. Alternately, the 'donor' protein molecule may utilize the natural fluorescent energy of tryptophan residues. Labels are chosen that emit different wavelengths of light, such that the 'acceptor' molecule label may be differentiated from that of the 'donor'. Since the efficiency of energy transfer between the labels is related to the distance separating the molecules, the spatial relationship between the molecules can be assessed. In a situation in which binding occurs between the molecules, the fluorescent emission of the 'acceptor' molecule label in the assay should, in an embodiment of the invention, be maximal. An FET binding event can be conveniently measured through standard fluorometric detection means well known in the art (e.g., using a fluorimeter). Using this system, the ability of a candidate agent to inhibit interaction between NRIP1 and protein binding partners, such as PPAR, can be evaluated. Compounds that inhibit the interaction are identified as NRIP1 inhibitors.

For example, the present invention includes a method for identifying a candidate agent that increases transcription or production of apolipoprotein A-1 (apoA1) or that antagonizes NRIP1 activity; comprising (i) incubating a mixture comprising NRIP1 polypeptide that is labeled with a FET donor label or FET acceptor label and a polypeptide binding partner that binds to NRIP1 that is labeled with the other label; under conditions which allow association between the polypeptides, in the presence of a candidate agent; wherein the donor and acceptor are chosen such that when the NRIP1 binds to the polypeptide binding partner, the donor and the acceptor are brought into interacting proximity, producing a detectable luminescence lifetime change in the photoluminescence lifetime of the donor; and (ii) exposing the sample to an exciting amount of radiation, detecting the resulting emission; and calculating the apparent luminescence lifetime of the donor to quantify binding of the NRIP1 polypeptide to the binding partner polypeptide; wherein the candidate agent is identified as the NRIP1 inhibitor if fluorescence by the donor occurs at a lower level than that observed in the absence of said candidate agent.

In another embodiment, the ability of the NRIP1 protein to bind to a polypeptide binding partner (e.g., a PPAR) can be determined using real-time Biomolecular Interaction Analysis (BIA) (e.g., Sjolander et al., *Anal. Chem.* 63:2338-2345 (1991), and Szabo et al., *Curr. Opin. Struct. Biol* 5:699-705 (1995)). "Surface plasmon resonance" or "BIA" detects biospecific interactions in real time, without labeling any of the interactants (e.g., BIAcore). Changes in the mass at the binding surface (indicative of a binding event) result in alterations of the refractive index of light near the surface (the optical phenomenon of surface plasmon resonance (SPR)), resulting in a detectable signal which can be used as an indication of real-time reactions between biological molecules (NRIP1 and polypeptide binding partner). Using this system, the ability of a candidate agent to inhibit interaction between NRIP1 and binding partners, such as PPAR, can be evaluated. Compounds that inhibit the interaction are identified as potential NRIP1 inhibitors.

In some embodiments of the invention, NRIP1 or the candidate agent is anchored onto a solid phase. The NRIP1/candidate agent complexes anchored on the solid phase can be detected. Generally, the NRIP1 is anchored onto a solid surface, and the candidate agent (which is not anchored) can be labeled, either directly or indirectly, with detectable labels discussed herein. Candidate agents that bind to NRIP1 may be inhibitors and may, optionally, be further analyzed for inhibitory activity.

It may be desirable to immobilize either NRIP1, an anti-NRIP1 antibody, or its binding partner (e.g., a PPAR such as PPARalpha, PPARdelta, or PPARgamma) to a solid substrate or matrix to facilitate separation of complexed from uncomplexed forms of NRIP1, as well as to accommodate automation of the assay. Binding of a candidate agent to an NRIP1 protein, or interaction of an NRIP1 and a binding partner in the presence and absence of a candidate agent, can be accomplished in any vessel suitable for containing the reactants. Examples of such vessels include microtiter plates, test tubes, and micro-centrifuge tubes. In one embodiment, an NRIP1 or binding partner fusion protein can be provided that adds a domain that allows one or both of the proteins to be bound to the solid substrate. For example, glutathione-S-transferase/NRIP1 fusion proteins or glutathione-S-transferase/binding partner fusion proteins (e.g., GST-PPAR) can be adsorbed onto glutathione Sepharose beads (Sigma Chemical, St. Louis, Mo.) or glutathione derivatized microtiter plates, which are then combined with the candidate agent. In such an embodiment of the invention, only one of the members of the complex to be formed is fused to GST; the other member is free to diffuse away from the solid substrate. In a positive control assay, NRIP1 and binding partner complex are allowed to form on the solid substrate in the absence of any candidate agent or inhibitor of complex formation. The mixture is then incubated under conditions conducive to complex formation (e.g., at physiological conditions for salt and pH). Following incubation, the beads or microtiter plate wells are washed to remove any unbound components (e.g., the non-GST-fused protein), the solid substrate can be immobilized in the case of beads, and the complex is determined either directly or indirectly, for example, as described above. Alternatively, the complexes can be dissociated from the matrix, and the level of complex bound and then dissociated can be determined using standard techniques. Candidate agents which inhibit binding between the NRIP1 and the binding partner (e.g., PPAR) can be identified as inhibitors of NRIP1. For example, candidate agents that cause a decrease in the amount of complex bound relative to a positive control assay (e.g., discussed above) are identified as inhibitors.

Other techniques for immobilizing either an NRIP1 protein or a binding partner on matrices include using conjugation of biotin and streptavidin. Biotinylated NRIP1 protein or binding partner can be prepared from biotin-NHS(N-hydroxysuccinimide) using techniques known in the art (e.g., biotinylation kit, Pierce Chemicals, Rockford, Ill.), and immobilized on the wells of streptavidin-coated 96 well plates (Pierce Chemical). Moreover, NRIP1 or the binding partner can be fused to a histidine tag ($His_6$) and immobilized to a divalent cation matrix (e.g., $Ni^{2+}$ or $Co^{2+}$).

Where the previously non-immobilized component is pre-labeled, the presence of a label immobilized on the surface indicates that complexes were formed. Where the previously non-immobilized component is not pre-labeled, an indirect label can be used to detect complexes anchored on the surface; e.g., using a labeled antibody specific for the immobilized component (the antibody, in turn, can be directly labeled or indirectly labeled with, e.g., a labeled anti-Ig secondary antibody).

In some cases, a sandwich-type immune assay (e.g., ELISA; enzyme linked immunosorbent assay) is performed utilizing antibodies reactive with NRIP1 protein or binding partners, but which do not interfere with binding of the NRIP1 protein to its binding partners (e.g., a PPAR). Such antibodies (capture antibodies) can be derivatized to the wells of the plate, and unbound reactant, (e.g., PPAR) or NRIP1 protein, can be trapped in the wells by binding to the capture antibody-bound protein (e.g., well/antibody/NRIP1/PPAR). Methods for detecting such complexes include immunodetection of complexes using detecting antibodies reactive with the protein that is not directly bound to the wells via antibody binding. For example, if NRIP1 is bound to the well via anti-NRIP1 antibody binding, the binding partner, PPAR, bound to NRIP1 may be detected by binding a labeled antibody to the bound PPAR. Alternatively, an unlabeled anti-PPAR antibody can be bound directly to PPAR and a labeled secondary antibody, specific for the anti-PPAR detecting antibody immunoglobulin can be used to detect the anti-PPAR. In this embodiment, the presence of the label in the wells would indicate the presence of PPAR and, thus, an NRIP1/PPAR complex. Furthermore, enzyme-linked assays which rely on detecting an enzymatic activity associated with the NRIP1 protein or target molecule may be employed. These assays can be performed in the presence of a candidate agent. A candidate agent that reduces complex formation relative to an assay performed in its absence would indicate that the candidate agent is an NRIP1 inhibitor.

Alternatively, cell-free assays can be conducted in a liquid phase. In such an assay, the reaction products are separated from unreacted components by any of a number of standard techniques, including but not limited to: differential centrifugation (see, for example, Rivas et al., *Trends Biochem. Sci.* 18:284-7 (1993)); chromatography (gel filtration chromatography, ion-exchange chromatography); electrophoresis (e.g., Ausubel et al., eds. Current Protocols in Molecular Biology 1999, J. Wiley: New York.); and immunoprecipitation (see, for example, Ausubel et al., eds., 1999, Current Protocols in Molecular Biology, J. Wiley: New York). Such resins and chromatographic techniques are known to one skilled in the art (e.g., Heegaard, *J. Mol. Recognit.* 11:141-148 (1998); Hage et al., *J. Chromatogr. B. Biomed. Sci. Appl.* 699:499-525 (1997). Further, fluorescence energy transfer may also be conveniently utilized, as described herein, to detect binding without further purification of the complex from solution.

An NRIP1 can, in vivo, interact with one or more cellular or extracellular macromolecules, such as proteins (e.g., a PPAR). Such cellular and extracellular macromolecules may be referred to herein as "binding partners." Compounds that disrupt such interactions are useful for regulating the activity of the NRIP1. Such compounds can include, but are not limited to, molecules such as antibodies, peptides, and small molecules. In alternative embodiments, the invention provides methods for determining the ability of the candidate agent to modulate the activity of an NRIP1 protein through modulation of the activity of a downstream effector of an NRIP1 target molecule. For example, the activity of the effector molecule on an appropriate target can be determined, or the binding of the effector to an appropriate target can be determined, as described herein.

In another embodiment of the invention, modulators of NRIP1 expression (RNA or protein) are identified using screening assays. An example of such modulators includes anti-sense or RNAi molecules that bind to NRIP1 mRNA in the cell. For example, a cell or cell-free mixture is contacted with a candidate agent and the expression of NRIP1 mRNA or protein is evaluated relative to the level of is expression of NRIP1 mRNA or protein in the absence of the candidate agent. When expression of NRIP1 mRNA or protein is greater in the presence of the candidate agent than in its absence, the candidate agent is identified as a stimulator (candidate compound) of NRIP1 mRNA or protein expression. When expression of NRIP1 mRNA or protein is less in the presence of the candidate agent than in its absence, the candidate agent is identified as an inhibitor of NRIP1 mRNA or protein expression. The level of NRIP1 mRNA or protein expression can be determined by methods described herein and methods known in the art such as Northern blot or Western blot for detecting NRIP1 mRNA or protein, respectively.

Specific embodiments of the present invention include a method for identifying an RNAi molecule (e.g., RNA or DNA, single or double stranded) that inhibits expression (e.g., transcription) of NRIP1 or that increases production of apoA1 comprising contacting a nucleic acid sense strand encoding NRIP1 (e.g., mRNA) with a candidate agent which is an RNA or DNA molecule and determining if the candidate agent hybridizes to the sense strand (e.g., and thereby leads to degradation of the mRNA transcript to which it has hybridized or prevents translation of the mRNA to which is has hybridized); wherein the candidate agent is identified as an RNAi molecule that inhibits expression of NRIP1 if said agent hybridizes to the sense strand. Another embodiment of the invention includes a method for identifying an RNAi molecule that inhibits expression of NRIP1 or that increase production of apoA1 comprising contacting an mRNA encoding NRIP1, in a cell, with a candidate agent, which is an RNA or DNA molecule, and determining if expression of NRIP1 in the cell decreases; wherein the candidate agent is identified as an RNAi molecule that inhibits expression of NRIP1 if said expression is observed to decrease.

In another aspect of the invention, the new methods described herein pertain to a combination of two or more of the assays described herein. For example, a modulating agent can be identified using a cell-based or a cell-free assay, and the ability of the agent to modulate the activity of an NRIP1 protein can be confirmed in vivo, e.g., in an animal model. For example, a human apoA1 transgenic animal can be dosed with a candidate agent for 7 days and serum lipoproteins measured. Serum apoA1 and HDL-C can be measured and an increase in apoA1 levels indicates that the candidate agent is an NRIP1 inhibitor. Ideally, the apoA1 level increase should be selective such that increases in apoB containing lipoproteins LDL and VLDL should not occur. Examples of potential apoA1 transgenic animals for use in such a model include transgenic C57BL/6-Tg (APOA1)1Rub/J mice (Rubin et al, *PNAS USA* 88:434-438 (1991), human CETP transgenic C57BL/6-Tg(CETP) (Agellon et al., *J. Biol. Chem.* 266: 10796-10801 (1991), Syrian golden hamsters, rats, cynomologous monkeys and rhesus monkeys.

An alternate animal model is based on the discovery that administration of therapeutically effective amounts of an NRIP1 inhibitor will promote fecal sterol excretion. It has been shown that apoA1 plays a role in promoting macrophage reverse cholesterol transport (RCT). Thurs, an NRIP1 inhibitor will promote cholesterol mobilization from macrophage to plasma, liver and then feces (Zhang et al., *Circulation* 108:661-663 (2003). Compounds that promote cholesterol mobilization from macrophage to plasma, liver and then feces can be identified as or confirmed as NRIP1 inhibitors. In vivo RCT can be measured using methods known in the art. For example, J774 macrophages can be loaded with cholesterol by incubating with acetylated LDL labeled with $^3$H-cholesterol and then intraperitoneal injection of the labeled macrophages into recipient mice. Plasma and feces are collected at 24 hours and 48 hours, respectively. At 48 hours, mice are exsanguinated and liver tissue harvested. All samples are analyzed for tracer counts. Similar studies may be performed in any species by first isolating primary moncyte/macrophages and following the same protocol of labeling the primary cells with $^3$H-cholesterol.

This invention further pertains to novel agents identified by the above-described screening assays. Accordingly, it is within the scope of this invention to further use an agent (compound) identified as described herein (e.g., an NRIP1 modulating agent, an anti-sense NRIP1 nucleic acid molecule, an NRIP1 siRNA, an NRIP1-specific antibody, or an NRIP1-binding partner) in an appropriate animal model to determine the efficacy, toxicity, side effects, or mechanism of action, of treatment with such an agent. Furthermore, novel agents identified by the above-described screening assays can be used for treatments as described herein.

NRIP1 Modulators

Methods of modulating NRIP1 expression or activity can be accomplished using a variety of compounds including nucleic acid molecules that are targeted to an NRIP1 nucleic acid sequence or fragment thereof, or to an NRIP1 polypeptide. Compounds that may be useful for inhibiting NRIP1 expression or activity include polynucleotides, polypeptides, small non-nucleic acid organic molecules, small inorganic molecules, antibodies or fragments thereof, antisense oligonucleotides, siRNAs, and ribozymes. Methods of identifying such compounds are described herein.

RNA Inhibition (RNAi)

The present invention includes methods for screening for inhibitors of NRIP1 expression (e.g., transcription) as well as use of such inhibitors for treatment of NRIP1 mediated medical conditions. Such RNAi molecules or RNAi inhibitors include both RNA and DNA; for example, siRNA, miRNA and anti-sense molecules. Specifically, both double- and single-stranded molecules are in the scope of the invention. Double stranded molecules include both an anti-sense strand that binds to an NRIP1 mRNA and inhibits translation of NRIP1 and a passenger strand that does not bind the mRNA. Moreover, the invention includes DNA/RNA double stranded hybrids.

As mentioned above, RNAi molecules include miRNA molecules. miRNA molecules are short RNA species (~22 nucleotides in length) produced by Dicer cleavage of longer (~70 nucleotides in length) endogenous precursors with imperfect hairpin RNA structures. The miRNAs are believed to bind to sites that have partial sequence complementarity in the 3' untranslated region (UTR) of their target mRNA, causing repression of translation and inhibition of protein synthesis.

Long double-stranded RNA is cleaved by the RNase III family member, Dicer, into siRNAs in an ATP-dependent reaction. Alternatively, double stranded RNA can be smaller than the required length for Dicer processing (approximately 22 nucleotides in length). In this case, the RNA foregoes this step in intracellular processing. These siRNAs are then incorporated into the RNA-inducing silencing complex (RISC). Unwound, single-stranded antisense strand guides RISC to messenger RNA that has a complementary sequence, which results in the endonucleolytic cleavage of the target mRNA.

The RNAi molecules of the present invention include both those with two solid strands as well as those with a solid strand and a nicked or gapped second strand. In an embodiment of the invention, the solid strand is the anti-sense strand whereas the nicked or gapped strand is the passenger strand. Gaps of any length are within the scope of the present invention (e.g., 1, 2, 3, 4, 5, 6, 7, 8, 9 or 10 nucleotides in length).

The size of the RNAi molecules are also without limitation, but may, in some embodiments of the invention, include Dicer substrates and non-Dicer substrates. Lengths of less than 15, 15, 16, 17, 18, 19, 20, 21, 22, 23, 24, 25, 26, 27, 28, 29, 30, 31, 32, 33, 34, 35, 36, 37, 38, 39, 40, and more than 40 nucleotides in length are within the scope of the invention.

The RNAi molecules may also comprise overhangs at any of the 4 ends of the double stranded molecules of the present invention or blunt ends at one or both sides of the molecules.

Moreover, the RNAi molecules may include one or more mismatches between the anti-sense strand and the target NRIP1 mRNA or the passenger strand, thus forming a ragged end or an internal bubble in the mRNA/antisense or passenger/anti-sense molecule.

The molecules may also include high order structure including hairpin loops at one or more ends as well as internal hairpins and cloverleaf bubbles.

Examples of nucleic acids include RNAi molecules targeting the following sequences:

GAAGCGUGCUAACGAUAAAUU (SEQ ID NO: 7) (siRNA #27-5);

AGAAGGAUGUUGGCAGUUAUU (SEQ ID NO: 8) (siRNA #27-6),

AUACGAAUCUUCCUGAUGUUU (SEQ ID NO: 9) (siRNA #27-8), and

AGACUAUACCUAAGCCAAU (SEQ ID NO: 10) (dsiRNA #27-1)

AGGAGUCACAGAAAUAAUG (SEQ ID NO: 11) (dsiRNA #27-2) as well as the corresponding RNA molecules and double stranded versions of any single stranded molecules. Indeed, the RNAi molecules of the present invention can bind to any portion of the NRIP1 mRNA and the scope of the present invention is intended to encompass any such molecule and its use. Other such molecules that function using the mechanisms associated with RNAi can also be used including chemically modified RNAi molecules and vector driven expression of hairpin RNA that are then cleaved to siRNA. The nucleic acid molecules or constructs that are useful as described herein include those wherein the antisense strand is substantially identical, e.g., at least 80% (or more, e.g., 85%, 90%, 95%, or 100%) identical, e.g., having 3, 2, 1, or 0 mismatched nucleotide(s), to a target region in the NRIP1 mRNA. The dsRNA molecules can be chemically synthesized, can be transcribed in vitro from a DNA template, or can be transcribed in vivo. The dsRNA molecules can be designed using methods known in the art, e.g., Dharmacon.com (see, siDESIGN CENTER) or "The siRNA User Guide," available on the Internet at mpibpc.gwdg.de/abteilunge-n/100/105/sirna.html.

Negative control RNAi molecules which may, in an embodiment of the invention, be "scrambled", and have the same nucleotide composition as the selected RNAi molecules, but without significant sequence complementarity to the appropriate genome. Such negative controls can be designed by randomly scrambling the nucleotide sequence of the selected RNAi molecules; a homology search can be performed to ensure that the negative control lacks homology to any other gene in the appropriate genome. Controls can also be designed by introducing an appropriate number of base mismatches into the selected RNAi molecule sequence.

The nucleic acid compositions that are useful for the methods described herein include both un-crosslinked RNAi molecules and crosslinked RNAi molecules. Crosslinking can be used to alter the pharmacokinetics of the composition, for example, to increase half-life in the body. Thus, the invention includes RNAi molecules that have two complementary strands of nucleic acid, such that the two strands are crosslinked. For example, a 3' OH terminus of one of the strands can be modified, or the two strands can be crosslinked and modified at the 3'OH terminus. The RNAi can contain a single crosslink (e.g., a psoralen crosslink). In some cases, the RNAi has at its 3' terminus a biotin molecule (e.g., a photo-cleavable biotin), a peptide (e.g., a Tat peptide), a nanoparticle, a peptidomimetic, organic compounds (e.g., a dye such as a fluorescent dye), or dendrimer. Modifying RNAi molecules in this way can improve cellular uptake or enhance cellular targeting activities of the resulting RNAi molecule as compared to the corresponding RNAi molecule, are useful for tracing the RNAi molecule derivative in the cell, or improve the stability of the RNAi molecule compared to the corresponding RNAi molecule. Moreover, the molecules may be conjugated to a PEG molecule.

In an embodiment of the invention, the RNAi molecule of the invention is conjugated to a peptide that directs the molecule to the appropriate organ, e.g., the liver, pancreas, small intestine, lung, brain, fat (adipose), muscle or kidney. In an embodiment of the invention, the peptide is a Tryptophan-cage (Trp.-cage) peptide (see e.g., U.S. Pat. No. 7,329,725).

The nucleic acid compositions described herein can be unconjugated or can be conjugated to another moiety, such as a nanoparticle, to enhance a property of the compositions, e.g., a pharmacokinetic parameter such as absorption, efficacy, bioavailability, and/or half-life. The conjugation can be accomplished using methods known in the art, e.g., using the methods of Lambert et al., *Drug Deliv. Rev.,* 47:99-112 (2001) (describes nucleic acids loaded to polyalkylcyanoacrylate (PACA) nanoparticles); Fattal et al., *J. Control Release,* 53:137-143 (1998) (describes nucleic acids bound to nanoparticles); Schwab et al., *Ann. Oncol.* 5 Suppl. 4:55-8 (1994) (describes nucleic acids linked to intercalating agents, hydrophobic groups, polycations or PACA nanoparticles); and Godard et al., *Eur. J. Biochem.* 232:404-410 (1995) (describes nucleic acids linked to nanoparticles).

The nucleic acid molecules can also be labeled using any method known in the art; for instance, the nucleic acid compositions can be labeled with a fluorophore, e.g., Cy3, fluorescein, or rhodamine. The labeling can be carried out using a kit, e.g., the Silencer siRNA labeling kit (Ambion). Additionally, the molecule can be radiolabeled, e.g., using $^3$H, $^{32}$P, or other appropriate isotope.

The present invention includes embodiments wherein the NRIP1 RNAi molecules have a 5-methyluridine (ribothymidine) or a 2-thioribothymidine in place of at least one uridine on a strand, or in place of each and every uridine on a strand. In further embodiments, the RNAi molecules may comprise any one or more of 5-methyluridine (ribothymidine), 2-thioribothymidine, deoxyuridine, locked nucleic acid (LNA) molecules (e.g., A, G, C, T or U), unlocked nucleic acid molecules (e.g., A, G, C, T or U), sugar modified with 2'-Omethyl, or G clamp, or any combination thereof. In certain embodiments, the RNAi molecule comprises a 2'-sugar substitution, such as a 2'-O-methyl, 2'-O-methoxyethyl, 2'-O-2-methoxyethyl, 2'-O-allyl, or halogen (e.g., 2'-fluoro). In certain embodiments, the RNAi molecule comprises at least one terminal cap substituent on one or both ends of a strand such as, independently, an alkyl, abasic, deoxy abasic, glyceryl, dinucleotide, acyclic nucleotide, or inverted deoxynucleotide moiety. In other embodiments, the RNAi molecule further comprises at least one modified internucleoside linkage, such as, independently, a phosphorothioate, chiral phosphorothioate, phosphorodithioate, phosphotriester, aminoalkylphosphotriester, methyl phosphonate, alkyl phosphonate, 3'-alkylene phosphonate, 5'-alkylene phosphonate, chiral phosphonate, phosphonoacetate, thiophosphonoacetate, phosphinate, phosphoramidate, 3'-amino phosphoramidate, aminoalkylphosphoramidate, thionophosphoramidate, thionoalkylphosphonate, thionoalkylphosphotriester, selenophosphate, or boranophosphate linkage.

Synthetic RNAi molecules can be delivered into cells by liposome, e.g., cationic liposome, transfection and electroporation. Sequences that are modified to improve their stability can be used. Such modifications can be made using methods known in the art (e.g., siSTABLE, Dharmacon). Such stabilized molecules are particularly useful for in vivo methods such as for administration to a subject to decrease NRIP1 expression. Longer term expression can also be achieved by delivering a vector that expresses the RNAi molecules (or other nucleic acid) to a cell, e.g., a fat, liver, or muscle cell. Several methods for expressing duplexes within cells from recombinant DNA constructs allow longer-term target gene suppression in cells, including mammalian Pol III promoter systems (e.g., HI or U6/snRNA promoter systems (Tuschl, *Nature Biotechnol.* 20:440-448, (2002)) capable of expressing functional double-stranded siRNAs; (Bagella et al., *J. Cell. Physiol.,* 177(2):206-213 (1998); Lee et al., *Nature Biotechnol.* 20:500-505 (2002); Paul et al., *Nature Biotechnol.* 20:505-508 (2002); Yu et al., *PNAS USA* 99(9):6047-6052 (2002); Sui et al., *PNAS USA* 99(6):5515-5520 (2002)). Constructs containing RNAi molecule sequence under the control of T7 promoter also make functional RNAi molecules when cotransfected into the cells with a vector expression T7 RNA polymerase (Jacque, *Nature* 418:435-438 (2002)).

Moreover, RNAi molecules of the present invention can be formulated into liposomal formulations (e.g., cationic liposomes) for therapeutic delivery to a subject, that include the use of RNAi compositions comprising surface-modified liposomes containing poly(ethylene glycol) lipids (PEG-modified, or long-circulating liposomes or stealth liposomes). Such long-circulating liposomes enhance the pharmacokinetics and pharmacodynamics of nucleic acid molecules as compared to conventional cationic liposomes. Long-circulating liposomes may also provide additional protection from nuclease degradation as compared to cationic liposomes in theory due to avoiding accumulation in metabolically aggressive MPS tissues, such as the liver and spleen. In one embodiment, this disclosure provides compositions suitable for administering RNAi molecules of this disclosure to specific cell types, such as hepatocytes. For example, the asialoglycoprotein receptor (ASGPr) (Wu et al., *J. Biol. Chem.* 262: 4429 (1987)) is unique to hepatocytes and binds branched galactose-terminal glycoproteins, such as asialoorosomucoid (ASOR). Binding of such glycoproteins or synthetic glycoconjugates to the receptor takes place with an affinity that strongly depends on the degree of branching of the oligosaccharide chain, for example, triatennary structures are bound with greater affinity than biatenarry or monoatennary chains (Baenziger and Fiete, *Cell* 22: 611 (1980); Connolly et al, *J. Biol. Chem.* 257:939 (1982). Lee and Lee, *Glycoconjugate J.* 4:317, (1987)) obtained this high specificity through the use of N-acetyl-D-galactosamine as the carbohydrate moiety, which has higher affinity for the receptor compared to galactose. This "clustering effect" has also been described for the binding and uptake of mannosyl-terminating glycoproteins or glycoconjugates (Ponpipom et al, *J. Med. Chem.* 24:1388 (1981). The use of galactose and galactosamine based conjugates to transport exogenous compounds across cell membranes can provide a targeted delivery approach to the treatment of liver disease. The use of bioconjugates can also provide a reduction in the required dose of therapeutic compounds required for treatment. Furthermore, therapeutic bioavailability, pharmacodynamics, and pharmacokinetic parameters can be modulated through the use of dsRNA bioconjugates of this disclosure.

In some cases, a pool of RNAi molecules is used to modulate the expression of NRIP1. The pool is composed of at least 2, 3, 4, 5, 8, or 10 different sequences targeted to NRIP1 at different positions (overlapping or non-overlapping).

RNAi molecules or other compositions that inhibit NRIP1 expression or activity are effective for ameliorating undesirable effects of a disorder related to lipid metabolism when NRIP1 RNA levels are reduced by, in an embodiment of the invention, at least 25%, 50%, 75%, 90%, or 95%. In some cases, it is desired that NRIP1 RNA levels be reduced by not more than 10%, 25%, 50%, or 75%. Methods of determining the level of NRIP1 expression can be determined using methods known in the art. For example, the level of NRIP1 RNA can be determined using Northern blot detection on a sample from a cell line or a subject. Levels of NRIP1 protein can also be measured using, e.g., an immunoassay method.

Ribozymes

Ribozymes that have specificity for an NRIP1 nucleic acid sequence can also be used to inhibit NRIP1 expression. Ribozymes are catalytic RNA molecules with ribonuclease activity that are capable of cleaving a single-stranded nucleic acid, such as an mRNA, to which they have a complementary region. Thus, ribozymes (e.g., hammerhead ribozymes (described in Haseloff and Gerlach, *Nature* 334:585-591 (1988)) can be used to catalytically cleave mRNA transcripts to thereby inhibit translation of the protein encoded by the mRNA. Methods of designing and producing ribozymes are known in the art (see, e.g., Scanlon, 1999, Therapeutic Applications of Ribozymes, Humana Press). A ribozyme having specificity for an NRIP1 nucleic acid molecule or fragment thereof can be designed based upon the nucleotide sequence of an NRIP1 cDNA. For example, a derivative of a Tetrahymena L-19 IVS RNA can be constructed in which the nucleotide sequence of the active site is complementary to the nucleotide sequence to be cleaved in an NRIP1 RNA (Cech et al. U.S. Pat. No. 4,987,071; and Cech et al., U.S. Pat. No. 5,116,742). Alternatively, an mRNA encoding an NRIP1 or fragment thereof can be used to select a catalytic RNA having a specific ribonuclease activity from a pool of RNA molecules (See, e.g., Bartel and Szostak, *Science* 261:1411-1418 (1993)).

Nucleic acid molecules that form triple helical structures can also be used to modulate NRIP1 expression. For example, expression of an NRIP1 polypeptide can be inhibited by targeting nucleotide sequences complementary to the regulatory region of the gene encoding the polypeptide (e.g., the promoter and/or enhancer) to form triple helical structures that prevent transcription of the gene in target cells. See generally Helene, *Anticancer Drug Des.* 6(6):569-84 (1991); Helene, *Ann. N.Y. Acad. Sci.* 660:27-36 (1992); and Maher, *Bioassays* 14(12):807-15 (1992).

A nucleic acid molecule for use as described herein can be modified at the base moiety, sugar moiety or phosphate backbone to improve, e.g., the stability, hybridization, or solubility of the molecule. For example, the deoxyribose phosphate backbone of a nucleic acid can be modified to generate peptide nucleic acids (see Hyrup et al., *Bioomanic & Medicinal Chem.* 4(1):5-23 (1996)). Peptide nucleic acids (PNAs) are nucleic acid mimics, e.g., DNA mimics, in which the deoxyribose phosphate backbone is replaced by a pseudopeptide backbone and only the four natural nucleobases are retained. The neutral backbone of PNAs allows for specific hybridization to DNA and RNA under conditions of low ionic strength. The synthesis of PNA oligomers can be performed using standard solid phase peptide synthesis protocols, e.g., as described in Hyrup et al., 1996, supra; Perry-O'Keefe et al., *PNAS USA* 93:14670-675 (1996).

PNAs can be used in therapeutic and diagnostic applications. For example, PNAs can be used as antisense or antigene agents for sequence-specific modulation of gene expression by, e.g., inducing transcription or translation arrest or inhibiting replication. PNAs can also be used, e.g., in the analysis of single base pair mutations in a gene by, e.g., PNA directed PCR clamping; as artificial restriction enzymes when used in combination with other enzymes, e.g., S1 nucleases (Hyrup, 1996, supra; or as probes or primers for DNA sequence and hybridization (Hyrup, 1996, supra; Perry-O'Keefe et al., *PNAS USA* 93:14670-675 (1996)).

PNAs can be modified, e.g., to enhance their stability or cellular uptake, by attaching lipophilic or other helper groups to PNA, by the formation of PNA-DNA chimeras, or by the use of liposomes or other techniques of drug delivery known in the art. For example, PNA-DNA chimeras can be generated which may combine the advantageous properties of PNA and DNA. Such chimeras allow DNA recognition enzymes, e.g., RNAse H and DNA polymerases, to interact with the DNA portion while the PNA portion would provide high binding affinity and specificity. PNA-DNA chimeras can be linked using linkers of appropriate lengths selected in terms of base stacking, number of bonds between the nucleobases, and orientation (Hyrup, 1996, supra). The synthesis of PNA-DNA chimeras can be performed as described in Hyrup, 1996, supra, and Finn et al., *Nucleic Acids Res.* 24:3357-63 (1996). For example, a DNA chain can be synthesized on a solid support using standard phosphoramidite coupling chemistry and modified nucleoside analogs. Compounds such as 5'-(4-methoxytrityl)amino-5'-deoxy-thymidine phosphoramidite can be used as a link between the PNA and the 5' end of DNA (Mag et al., *Nucleic Acids Res.* 17:5973-88 (1989)). PNA monomers are then coupled in a stepwise manner to produce a chimeric molecule with a 5' PNA segment and a 3' DNA segment (Finn et al., *Nucleic Acids Res.* 24:3357-63 (1996)). Alternatively, chimeric molecules can be synthesized with a 5' DNA segment and a 3' PNA segment (Peterser et al., *Bioorganic Med. Chem. Lett.* 5:1119-11124 (1975)).

A nucleic acid targeting an NRIP1 nucleic acid sequence can include appended groups such as peptides (e.g., for targeting host cell receptors in vivo), or agents facilitating transport across the cell membrane (see, e.g., Letsinger et al., *PNAS USA* 86:6553-6556 (1989); Lemaitre et al., *PNAS USA* 84:648-652 (1989); WO 88/09810) or the blood-brain barrier (see, e.g., WO 89/10134). In addition, oligonucleotides can be modified with hybridization-triggered cleavage agents (see, e.g., Krol et al., *Bio/Techniques* 6:958-976 (1988)) or intercalating agents (see, e.g., Zon, *Pharm. Res.* 5:539-549 (1988)). To this end, the oligonucleotide may be conjugated to another molecule, e.g., a peptide, hybridization triggered cross-linking agent, transport agent, or a hybridization-triggered cleavage agent.

NRIP1 Polypeptides

Isolated NRIP1 polypeptides, fragments thereof, and variants thereof are provided herein. These polypeptides can be used, e.g., as immunogens to raise antibodies, in screening methods, or in methods of treating subjects, e.g., by administration of the polypeptides. An "isolated" or "purified" polypeptide or biologically active portion thereof is substantially free of cellular material or other contaminating proteins from the cell or tissue source from which the protein is derived, or substantially free of chemical precursors or other chemicals when chemically synthesized. The language "substantially free of cellular material" includes preparations of polypeptides in which the polypeptide of interest is separated from components of the cells or system from which it is isolated or produced to any degree. Thus, a polypeptide that is substantially free of cellular material includes preparations of polypeptides having less than about 30%, 20%, 10%, or 5% (by dry weight) of heterologous protein (also referred to herein as "contaminating protein"). In general, when the polypeptide or biologically active portion thereof is recombinantly produced, it is also substantially free of culture medium, i.e., culture medium represents less than about 20%, 10%, or 5% of the volume of the protein preparation. In general, when the polypeptide is produced by chemical synthesis, it is substantially free of chemical precursors or other chemicals, i.e., it is separated from chemical precursors or other chemicals that are involved in the synthesis of the polypeptide. Accordingly such preparations of the polypeptide have less than about 30%, 20%, 10%, or 5% (by dry weight) of chemical precursors or compounds other than the polypeptide of interest.

Expression of polypeptides can be assayed to determine the amount of expression. Methods for assaying protein expression are known in the art and include Western blot, immunoprecipitation, and radioimmunoassay.

As used herein, a "biologically active portion" of an NRIP1 protein includes a fragment of a NRIP1 protein that exhibits an NRIP1 activity to any degree, e.g., that participates in an interaction between an NRIP1 molecule and binding partner (e.g., a PPAR). Biologically active portions of an NRIP1 protein include peptides including amino acid sequences sufficiently homologous to the amino acid sequence of an NRIP1 protein that includes fewer amino acids than a full-length NRIP1 protein, and exhibits at least one activity of an NRIP1 protein. Typically, but not necessarily, biologically active portions include a domain or motif with at least one activity of the NRIP1 protein (e.g., an LXXLL motif, or a PXDLS motif). A biologically active portion of an NRIP1 protein can be a polypeptide that is, for example, 10, 25, 50, 100, 200 or more amino acids in length. Biologically active portions of an NRIP1 protein can be used as targets for developing agents that modulate an NRIP1 mediated activity, e.g., compounds that inhibit NRIP1 activity and result in increased transcription or production of apoA1.

In some embodiments, the NRIP1 polypeptide has a sequence identical to a sequence disclosed herein (e.g., a human NRIP1 amino acid sequence found under GenBank Accession No. NP_003480). Other useful polypeptides are substantially identical (e.g., at least about 45%, 55%, 65%, 75%, 85%, 95%, or 99% sequence similarity or identity) to the sequence found under Accession No. NP_003480 and (a) retain an activity of NRIP1 yet differs in amino acid sequence due to natural allelic variation or mutagenesis, and/or (b) exhibits an altered functional activity (e.g., as a dominant negative) where desired. Provided herein are variants that have an altered amino acid sequence which can function as either agonists (mimetics) or as antagonists. Variants can be generated by mutagenesis, e.g., discrete point mutation or truncation. An agonist can retain substantially the same, or a subset, of the biological activities of the naturally occurring form of the polypeptide. An antagonist of a polypeptide can inhibit one or more of the activities of the naturally occurring form of the polypeptide by, for example, competitively binding to a downstream or upstream member of a cellular signaling cascade that includes the polypeptide. Thus, specific biological effects can be elicited by treatment with a variant of limited function. Treatment of a subject with a variant having a subset of the biological activities of the naturally occurring form of the polypeptide can have fewer side effects in a subject relative to treatment with the naturally occurring form of the polypeptide. In some embodiments, the variant NRIP1 polypeptide is a dominant negative form of NRIP1. Dominant negatives may be desired, e.g., in methods in which inhibition of NRIP1 action is desired, e.g., to achieve increased apolipoprotein A-1 production and/or treatment of a disorder associated with low high-density lipoproteins (HDL) such as coronary heart disease.

Sequence identity refers to exact matches between amino acid and nucleotide sequences that are compared. Sequence similarity refers to matches between amino acid sequences wherein the matched amino acid residues are within the same amino acid family (e.g., basic, non-polar or aromatic). Such families are discussed more below.

Also provided herein are chimeric or fusion proteins of NRIP1 which may be used in connection with the various embodiments described herein. The NRIP1 polypeptides may be fused with one or more heterologous (i.e., non-NRIP1) polypeptides; such may be referred to as a "tag". A tag can also be an NRIP1 sequence that is not naturally contiguous with the NRIP1 portion of the fusion. The fusions of the present invention may comprise any of the polynucleotides or polypeptides set forth herein or any subsequence or fragment thereof. The fused polypeptides of the invention may be conveniently constructed, for example, by insertion of a polynucleotide of the invention or fragment thereof into an expression vector. The fusions of the invention include tags which facilitate purification or detection. Such tags include glutathione-S-transferase (GST), hexahistidine (His6) tags, His12 tags, maltose binding protein (MBP) tags, haemagglutinin (HA) tags, cellulose binding protein (CBP) tags and myc tags. Detectable tags such as $^{32}P$, $^{35}S$, $^{3}H$, $^{99m}Tc$, $^{123}I$, $^{111}In$, $^{68}Ga$, $^{18}F$, $^{125}I$, $^{131}I$, $^{113m}In$, $^{76}Br$, $^{67}Ga$, $^{99m}Tc$, $^{123}I$, $^{111}In$ and $^{68}Ga$ may also be used to label the polypeptides and polynucleotides of the invention. Methods for constructing and using such fusions are very conventional and well known in the art.

The comparison of sequences and determination of percent identity between two sequences is accomplished using a mathematical algorithm. The percent identity between two amino acid sequences can be determined using the Needleman and Wunsch, *J. Mol. Biol.* 48:444-453 (1970)) algorithm, which has been incorporated into the GAP program in the GCG software package (available on the Internet at gcg.com), using either a Blossum 62 matrix or a PAM250 matrix, and a gap weight of 16 and a length weight of 1. The percent identity between two nucleotide sequences can be determined using the GAP program in the GCG software package (also available on the Internet at gcg.com), using a NWSgapdna.CMP matrix, a gap weight of 40, and a length weight of 1.

In general, percent identity between amino acid sequences referred to herein can be determined using the BLAST algorithm, which is available to the public on the Internet at ncbi.nlm.nih.gov/BLAST. Sequence comparison can be performed using an ungapped alignment and using the default parameters (Blossum 62 matrix, gap existence cost of 11, per residue gap cost of 1, and a lambda ratio of 0.85). The mathematical algorithm used in BLAST programs is described in Altschul et al., Nucleic Acids Research 25:3389-3402, 1997.

A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, in such an embodiment of the invention, a predicted nonessential amino acid residue in an NRIP1 protein is generally replaced with another amino acid residue from the same side chain family. Alternatively, mutations can be introduced randomly along all or part of an NRIP1 coding sequence, such as by saturation mutagenesis, and the resultant mutants can be screened for NRIP1 biological activity to identify mutants that retain activity. The encoded protein can be expressed recombinantly and the activity of the protein can be determined.

Antibodies

An NRIP1 polypeptide, or a fragment thereof, can be used as an immunogen to generate antibodies using standard techniques for preparation of an antibody or antigen-binding fragment thereof e.g., monoclonal antibodies, camelized single domain antibodies, polyclonal antibodies, bispecific antibodies, chimeric antibodies, recombinant antibodies, anti-idiotypic antibodies, humanized antibodies, bispecific antibodies, diabodies, nanobodies, single chain antibodies, disulfide Fvs (dsfv), Fvs, Fabs, Fab' s, F(ab')₂s and domain antibodies. The full-length polypeptide or protein can be used or, alternatively, antigenic peptide fragments thereof, can be used as immunogens. The antigenic peptide of a protein comprises, in an embodiment of the invention, at least 8 (e.g., at least 10, 15, 20, or 30) contiguous amino acid residues of the amino acid sequence of an NRIP1 polypeptide, and encompasses an epitope of NRIP1 such that an antibody raised against the peptide forms a specific immune complex with the polypeptide. Such antibodies may be used, for example, therapeutically to treat medical disorders mediated by NRIP1 (e.g., as discussed herein).

An immunogen typically is used to prepare antibodies by immunizing a suitable subject (e.g., rabbit, goat, mouse or other mammal). An appropriate immunogenic preparation can contain, for example, a recombinantly expressed or a chemically synthesized polypeptide. The preparation can further include an adjuvant, such as Freund's complete or incomplete adjuvant, or similar immunostimulatory agent.

Polyclonal antibodies can be prepared as described above by immunizing a suitable subject with an NRIP1 polypeptide as an immunogen. The antibody titer in the immunized subject can be monitored over time by standard techniques, such as with an enzyme linked immunosorbent assay (ELISA) using immobilized polypeptide. If desired, the antibody molecules can be isolated from the mammal (e.g., from the blood) and further purified by well-known techniques, such as protein A chromatography to obtain the IgG fraction. At an appropriate time after immunization, e.g., when the specific antibody titers are highest, antibody-producing cells can be obtained from the subject and used to prepare monoclonal antibodies by standard techniques, such as the hybridoma technique originally described by Kohler and Milstein, *Nature* 256:495-497 (1975), the human B cell hybridoma technique (Kozbor et al., *Immunol. Today* 4:72 (1983)), the EBV-hybridoma technique (Cole et al., Monoclonal Antibodies and Cancer Therapy, Alan R. Liss, Inc., pp. 77-96, 1985) or trioma techniques. The technology for producing hybridomas is well known (see generally Current Protocols in Immunology, 30 1994, Coligan et al. (eds.) John Wiley & Sons, Inc., New York, N.Y.). Hybridoma cells producing a monoclonal antibody are detected by screening the hybridoma culture supernatants for antibodies that bind the polypeptide of interest, e.g., using a standard ELISA assay.

As an alternative to preparing monoclonal antibody-secreting hybridomas, a monoclonal antibody directed against a polypeptide can be identified and isolated by screening a recombinant combinatorial immunoglobulin library (e.g., an antibody phage display library) with the polypeptide of interest. Kits for generating and screening phage display libraries are commercially available (e.g., the Pharmacia Recombinant Phage Antibody System, Catalog No. 27-9400-01; and the Stratagene SurfZAP™ Phage Display Kit, Catalog No. 240612). Additionally, examples of methods and reagents particularly amenable for use in generating and screening antibody display library can be found in, for example, U.S. Pat. No. 5,223,409; WO 92/18619; WO 91/17271; WO 92/20791; WO 92/15679; WO 93/01288; WO 92/01047; WO 92/09690; WO 90/02809; Fuchs et al., *Bio/Technology* 9:1370-1372 (1991); Hay et al., *Hum. Antibod. Hybridomas* 3:81-85 (1992); Huse et al., *Science* 246:1275-1281 (1989); Griffiths et al., *EMBO J.* 12:725-734 (1993).

Additionally, recombinant antibodies, such as chimeric and humanized monoclonal antibodies, including both human and non-human portions, which can be made using standard recombinant DNA techniques, are provided herein. Such chimeric and humanized monoclonal antibodies can be produced by recombinant DNA techniques known in the art, for example using methods described in WO 87/02671; European Patent Application 184,187; European Patent Application 171,496; European Patent Application 173,494; WO 86/01533; U.S. Pat. No. 4,816,567; European Patent Application 125,023; Better et al., *Science* 240:1041-1043 (1988); Liu et al., *PNAS USA* 84:3439-3443 (1987); Liu et al., *J. Immunol.* 139:3521-3526 (1987); Sun et al., *PNAS USA*, 84:214-218 (1987); Nishimura et al., *Canc. Res.* 47:999-1005 (1987); Wood et al., *Nature* 314:446-449 (1985); and Shaw et al., *J. Natl. Cancer Inst.* 80:1553-1559 (1988); Morrison, *Science* 229:1202-1207 (1985); Oi et al., *Bio/Techniques* 4:214 (1986); U.S. Pat. No. 5,225,539; Jones et al., *Nature,* 321:552-525 (1986); Verhoeyan et al., *Science* 239:1534 (1988); and Beidler et al., *J. Immunol.* 141:4053-4060 (1988).

Completely human antibodies may be desirable for therapeutic treatment of human patients. Such antibodies can be produced using transgenic mice which are incapable of expressing endogenous immunoglobulin heavy and light chains genes, but which can express human heavy and light chain genes. The transgenic mice are immunized in the normal fashion with a selected antigen, e.g., all or a portion of a polypeptide. Monoclonal antibodies directed against the antigen can be obtained using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, and IgE antibodies. For an overview of this technology for producing human antibodies, see Lonberg and Huszar, *Int. Rev. Immunol.* 13:65-93 (1995). For a detailed discussion of this technology for producing human antibodies and human monoclonal antibodies and protocols for producing such antibodies, see, e.g., U.S. Pat. No. 5,625,126; U.S. Pat. No. 5,633,425; U.S. Pat. No. 5,569,825; U.S. Pat. No. 5,661,016; and U.S. Pat. No. 5,545,806. In addition, companies such as Abgenix, Inc. (Freemont, Calif.), can to be engaged to provide human antibodies directed against a selected antigen using technology similar to that described above.

Completely human antibodies that recognize a selected epitope can be generated using a technique referred to as "guided selection." In this approach a selected non-human monoclonal antibody, e.g., a murine antibody, is used to guide the selection of a completely human antibody recognizing the same epitope. (Jespers et al., *Biotechnology* 12:899-903 (1994)).

An antibody directed against NRIP1 can be used to detect the polypeptide (e.g., in a cellular lysate or cell supernatant) to evaluate its abundance and pattern of expression. The antibodies can also be used diagnostically to monitor protein levels in tissue as part of a clinical testing procedure, e.g., for example, to determine the efficacy of a given treatment regimen. Detection can be facilitated by coupling the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, beta-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^{3}H$.

Pharmaceutical Compositions

A candidate agent that has been screened by a method described herein and determined to modulate NRIP1 expression or activity can be considered a candidate compound. A candidate compound that has been screened, e.g., in an in vivo model of dyslipidemia, atherosclerosis of coronary heart disease, and determined to have a desirable effect on the disorder, e.g., by decreasing the expression or activity of NRIP, increasing the production of apoA1 or by raising plasma levels of apoA1 or HDL, can be considered a candidate therapeutic agent. Candidate therapeutic agents, once screened in a clinical setting, are therapeutic agents. Candidate therapeutic agents and therapeutic agents (e.g., anti-NRIP1 antibodies and antigen-binding fragments thereof) can be optionally optimized and/or derivatized, and formulated with physiologically and/or pharmaceutically acceptable excipients and/or carriers to form pharmaceutical compositions.

The compounds described herein that can modulate NRIP1 expression or activity (e.g., can modulate the interaction between NRIP1 and a PPAR) can be incorporated into pharmaceutical compositions. Such compositions typically include the compound and a pharmaceutically acceptable carrier. As used herein the language "pharmaceutically acceptable carrier" includes solvents, dispersion media, coatings, antibacterial and antifungal agents, isotonic and absorption delaying agents, and the like, compatible with pharmaceutical administration. Supplementary active compounds can also be incorporated into the compositions.

A pharmaceutical composition should be formulated to be compatible with its intended route of administration. Examples of routes of administration include parenteral and non-parenteral, e.g., intravenous, intramuscular, intraarterial, intradermal, subcutaneous, oral (e.g., inhalation), transdermal (topical), transmucosal, and rectal administration. Solutions or suspensions can include a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. A preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL. (BASF, Parsippany, N.J.) or phosphate buffered saline (PBS).

Generally, a pharmaceutical composition must be sterile and should be fluid to the extent that easy syringability exists. In general, it should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be desirable to include isotonic agents, for example, sugars, polyalcohols such as manitol, sorbitol, sodium chloride in the composition. Prolonged absorption of the injectable compositions can be brought about by including in the composition an agent that delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the methods of preparation can include vacuum drying or freeze-drying which yields a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, primogel, or corn starch; a lubricant such as magnesium stearate or sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment of the invention, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. Dosage units can also be accompanied by instructions for use.

Toxicity and therapeutic efficacy of such compounds can be determined using known pharmaceutical procedures in cell cultures (e.g., in cultures of fat cells, muscle cells, or liver cells) or experimental animals (animal models of obesity or of diabetes (e.g., type II diabetes). These procedures can be used, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit high therapeutic indices are preferred. While compounds that exhibit toxic side effects may be used, care should be taken to design a delivery system that targets such compounds to the site of affected tissue in to minimize potential damage to uninfected cells and, thereby, reduce side effects.

The data obtained from the cell culture assays and animal studies can be used in formulating a range of dosage for use in humans. The dosage of such compounds lies generally within a range of circulating concentrations that include the ED50 with little or no toxicity. The dosage may vary within this range depending upon the dosage form employed and the route of administration utilized. For a compound used as described herein (e.g., for treating diabetes in a subject), the therapeutically effective dose can be estimated initially from cell culture assays. A dose can be formulated in animal models to achieve a circulating plasma concentration range that includes the IC50 (i.e., the concentration of the candidate agent which achieves a half-maximal inhibition of symptoms) as determined in cell culture. Such information can be used to more accurately determine useful doses in humans. Levels in plasma may be measured, for example, by high performance liquid chromatography.

The present invention includes methods for treating or preventing a medical condition mediated by NRIP1 by administering a therapeutically effective amount of NRIP1 antagonist e.g., an anti-NRIP1 antibody or antigen-binding fragment thereof. As defined herein, a therapeutically effective amount of protein or polypeptide (e.g., antibody or fragment) (i.e., an effective dosage) ranges from about 0.001 to 30 mg/kg body weight, about 0.01 to 25 mg/kg body weight, about 0.1 to 20 mg/kg body weight, about 1 to 10 mg/kg, 2 to 9 mg/kg, 3 to 8 mg/kg, 4 to 7 mg/kg, or 5 to 6 mg/kg body weight. The protein or polypeptide can be administered one time per week for between about 1 to 10 weeks, generally between 2 to 8 weeks, between about 3 to 7 weeks, or for about 4, 5, or 6 weeks. One in the art will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of a protein, polypeptide, or antibody can include a single treatment or can include a series of treatments. In the case of a subject suffering from diabetes, blood glucose levels can be monitored and the dosages adjusted accordingly.

For antibodies or a fragment thereof, the dosage is, in an embodiment of the invention, about 0.1 mg/kg of body weight (generally 10 mg/kg to 20 mg/kg). If the antibody is to act in the brain, a dosage of 50 mg/kg to 100 mg/kg is, in an embodiment of the invention, appropriate. Generally, partially human antibodies and fully human antibodies have a longer half-life within the human body than other antibodies. Accordingly, lower dosages and less frequent administration are often possible with such species-matched antibodies. Modifications such as lipidation can be used to stabilize antibodies and to enhance uptake and tissue penetration (e.g., into the brain). A method for lipidation of antibodies is described by Cruikshank et al., *J. Acquired Immune Deficiency Syndromes and Human Retrovirology* 14:193 (1997).

Compounds that modulate expression or activity of a NRIP1 are described herein. Such a compound can be a small molecule. For example, such small molecules include, but are not limited to, peptides, peptidomimetics (e.g., peptoids), amino acids, amino acid analogs, polynucleotides, polynucleotide analogs, nucleotides, nucleotide analogs, organic or inorganic compounds (i.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

Exemplary doses include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram. It is furthermore understood that appropriate doses of a small molecule depend upon the potency of the small molecule with respect to the expression or activity to be modulated. When one or more of these small molecules is to be administered to an animal (e.g., a human) to modulate expression or activity of a polypeptide or nucleic acid of the invention, a physician, veterinarian, or researcher may, for example, prescribe a relatively low dose at first, subsequently increasing the dose until an appropriate response is obtained (e.g., an appropriate blood glucose level). In addition, it is understood that the specific dose level for any particular animal subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

An antibody or antigen-binding fragment thereof can be conjugated to or combined in association with a therapeutic moiety such as any of the further chemotherapeutic agents set forth herein.

A nucleic acid molecule that is useful for modulating NRIP1 expression or activity can be inserted into a vector and the resulting vector used as gene therapy vector. Gene therapy vectors can be delivered to a subject by, for example, intravenous injection, local administration (see U.S. Pat. No.

5,328,470) or by stereotactic injection (see e.g., Chen et al. (Proc. Natl. Acad. Sci. USA, 91:3054-3057, 1994). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

The pharmaceutical compositions can be included in a container, pack, or dispenser together with instructions for administration.

Methods of Treatment

Compounds described herein and those identified as described herein as NRIP1 modulators can be used to treat a subject that is at risk for or has a medical disorder mediated by NRIP1, e.g., a lipid metabolism-related disorder such as atherosclerosis or coronary heart disease. Methods of identifying such individuals are known in the art. Thus, methods and compositions for both prophylactic and therapeutic methods of treating a subject at risk of (or susceptible to) a disorder or having a disorder associated with aberrant or unwanted NRIP1 expression or activity are described herein. As used herein, the term "treatment" is defined as the application or administration of a therapeutic compound to a patient, or application or administration of a therapeutic compound to an isolated tissue or cell line from a patient, who has a disease, a symptom of disease or a predisposition toward a disease, with the purpose to cure, heal, alleviate, relieve, alter, remedy, ameliorate, improve or affect the disease, the symptoms of disease or the predisposition toward disease. A therapeutic compound includes, but is not limited to, small molecules such as small non-nucleic acid organic molecules, small inorganic molecules, peptides, synthetic peptides, antibodies, natural nucleic acid molecules (such as ribozymes, and RNAi molecules), and molecules containing nucleic acid analogs.

Also provided herein are methods for treating or preventing in a subject (e.g., a mammalian subject such as a human), a disease or condition associated with or mediated by an aberrant or unwanted NRIP1 expression or activity, by administering to the subject an NRIP1 inhibitor that inhibits NRIP1 expression or at least one NRIP1 activity (e.g., NRIP1 interaction with a PPAR such as PPARgamma). Subjects at risk for a disease that is caused or contributed to by aberrant or unwanted NRIP1 expression or activity can be identified by any or a combination of diagnostic or prognostic assays as described herein. Administration of a prophylactic compound can occur prior to the manifestation of symptoms characteristic of full-blown disease, e.g., a subject exhibiting low plasma HDL levels but that does not exhibit effects of dislipidemia associated with advanced disease, such that the disease or disorder is prevented or, alternatively, delayed in its progression. Methods known in the art can be used to determine the efficacy of the treatment. The appropriate compound used for treating the subject can be determined based on screening assays described herein.

It is possible that some cases of lipid metabolism-related disease are caused, at least in part, by an abnormal level of NRIP1 gene product, or by the presence of a NRIP1 gene product exhibiting abnormal activity (e.g., increased repressor activity compared to a wild type NRIP1). As such, the reduction in the level and/or activity of such gene products will bring about the amelioration of disorder symptoms.

As discussed, successful treatment of lipid metabolism-related disorders can be brought about by techniques that serve to inhibit the expression or activity of target gene products. For example, compounds, e.g., an agent identified using one or more of the assays described above, that proves to exhibit negative modulatory activity, can be used as described herein to prevent and/or ameliorate symptoms of lipid metabolism-related disorders. Such molecules can include, but are not limited to, peptides, phosphopeptides, small organic or inorganic molecules, or antibodies (including, for example, polyclonal, monoclonal, humanized, anti-idiotypic, chimeric or single chain antibodies, and Fab, F(ab')$_2$ and Fab expression library fragments, scFV molecules, and epitope-binding fragments thereof).

Further, RNAi molecules such as siRNA, antisense, and ribozyme molecules, that inhibit expression of an NRIP1 gene can also be used in accordance with the methods described herein to reduce the level of NRIP1 expression, thus effectively reducing the level of NRIP1 activity. Triple helix molecules can be utilized to reduce the level of NRIP1 activity.

Another method by which nucleic acid molecules can be utilized in treating or preventing a disease that can be treated by modulating NRIP1 expression is through the use of aptamer molecules specific for NRIP1 protein. Aptamers are nucleic acid molecules having a tertiary structure that permits them to specifically bind to protein ligands (e.g., Osborne, et al., *Curr. Opin. Chem. Biol.* 1: 5-9 (1997); and Patel, *Curr. Opin. Chem. Biol.* 1:32-46 (1997). Since nucleic acid molecules may be more conveniently introduced into target cells than therapeutic protein molecules may be, aptamers offer a method by which NRIP1 protein activity can be specifically decreased without the introduction of drugs or other molecules that may have pluripotent effects.

An antibody that specifically binds an NRIP1 can also be used. In an embodiment of the invention, internalizing antibodies are used. Lipofectin or liposomes can be used to deliver the antibody or a fragment of the Fab region that binds to the NRIP1 in a cell. Where fragments of the antibody are used, the smallest inhibitory fragment that binds to the target antigen can be used. For example, peptides having an amino acid sequence corresponding to the Fv region of the antibody can be used. Alternatively, single chain neutralizing antibodies that bind to intracellular NRIP1 can also be administered. Such single chain antibodies can be administered, for example, by expressing nucleotide sequences encoding single-chain antibodies within the target cell population (e.g., Marasco et al, *PNAS USA* 90:7889-7893 (1993).

The identified compounds that inhibit NRIP1 gene expression, synthesis and/or activity can be administered to a patient at therapeutically effective doses to prevent, treat, or ameliorate NRIP1 disorders. A therapeutically effective dose includes that amount of the compound sufficient to result in amelioration of signs, causes, symptoms or clinical indicia of the disorders to any degree. Toxicity and therapeutic efficacy of such compounds can be determined by standard pharmaceutical procedures as described above.

The data obtained from the cell culture assays and animal studies can be used in formulating a range of dosage for use in humans. In an embodiment of the invention, the dosage of such compounds lies generally within a range of circulating concentrations that include the $ED_{50}$. The dosage can vary within this range depending upon the dosage form employed and the route of administration utilized. For any compound used as described herein, the therapeutically effective dose might be estimated initially from cell culture assays. A dose can be formulated in animal models to achieve a circulating plasma concentration range that includes the $IC_{50}$ (i.e., the concentration of the candidate agent that achieves a half-maximal inhibition of symptoms) as determined in cell culture. Such information can be used to more accurately determine useful doses in humans. Levels in plasma can be measured, for example, by high performance liquid chromatography.

Another example of determination of effective dose for an individual is the ability to directly assay levels of "free" and "bound" compound in the serum of the test subject. Such assays may utilize antibody mimics and/or "biosensors" that have been created through molecular imprinting techniques. The compound that is able to modulate NRIP1 activity is used as a template, or "imprinting molecule," to spatially organize polymerizable monomers prior to their polymerization with catalytic reagents. The subsequent removal of the imprinted molecule leaves a polymer matrix that contains a repeated "negative image" of the compound and is able to selectively rebind the molecule under biological assay conditions. A detailed review of this technique can be seen in Ansell et al., *Current Opinion in Biotechnology* 7:89-94 (1996) and in Shea, *Trends in Polymer Science* 2:166-173 (1994). Such "imprinted" affinity matrixes are amenable to ligand-binding assays, whereby the immobilized monoclonal antibody component is replaced by an appropriately imprinted matrix. An example of the use of such matrixes in this way can be seen in Vlatakis et al., *Nature* 361:645-647 (1993). Through the use of isotope-labeling, the "free" concentration of compound that modulates the expression or activity of NRIP1 can be readily monitored and used in calculations of $IC_{50}$.

Such "imprinted" affinity matrixes can also be designed to include fluorescent groups whose photon-emitting properties measurably change upon local and selective binding of target compound. These changes can be readily assayed in real time using appropriate fiberoptic devices, in turn allowing the dose in a test subject to be quickly optimized based on its individual $IC_{50}$. An rudimentary example of such a "biosensor" is discussed in Kriz et al., *Analytical Chemistry* 67:2142-2144 (1995).

NRIP1 expression or activity can be modulated for therapeutic purposes. Accordingly, in an exemplary embodiment, the modulatory methods described herein involve contacting a cell with a compound that modulates one or more of the activities of NRIP1 protein activity (e.g., NRIP1 binding to a PPAR), associated with the cell. A compound that modulates NRIP1 activity can be a compound as described herein, such as a nucleic acid or a protein, a naturally-occurring target molecule of a NRIP1 protein (e.g., a NRIP1 substrate or receptor), a NRIP1 antibody, a NRIP1 agonist or antagonist, a peptidomimetic of a NRIP1 agonist or antagonist, or other small molecule.

Combination Therapy

The NRIP1 modulators described herein and those identified as described herein can also act in association with further therapeutic agents such as other pharmaceutical compositions or substances designed to modulate high density lipoproteins (HDL) or low density lipoproteins (LDL). For example, the method can involve combination therapy with statins (i.e., HMG CoA reductase inhibitors) and/or with a selective cholesterol uptake inhibitor (e.g. ezetimibe). The method typically involves administering, in association with the statin and/or cholesterol uptake inhibitor, an effective amount of one or more of the NRIP1 modulators described herein. In certain embodiments, the statin is selected from the group consisting of cerivastatin, atorvastatin, simvastatin, pravastatin, fluvastatin, lovastatin, rosuvastatin, and pitavastatin. The NRIP1 modulator and/or said statin and/or cholesterol uptake inhibitor can be administered as a unit dosage formulation. In certain embodiments, the administering comprises administering said NRIP1 modulator and/or said statin by a route selected from the group consisting of oral administration, nasal administration, rectal administration, intraperitoneal injection, intravascular injection, subcutaneous injection, transcutaneous administration, and intramuscular injection.

The term "in association with" indicates that the components (e.g., NRIP1 inhibitor and further chemotherapeutic agent) can be formulated into a single composition for simultaneous delivery or formulated separately into two or more compositions (e.g., a kit). Furthermore, each component can be administered to a subject at a different time than when the other component is administered; for example, each administration may be given non-simultaneously (e.g., separately or sequentially) at several intervals over a given period of time. Moreover, the separate components may be administered to a subject by the same or by a different route (e.g., wherein an anti-NRIP1 antibody formulation is administered parenterally and ezetimibe is administered orally).

This invention also provides a method of mitigating one or more symptoms associated with dislipidemia in a mammal. The method typically involves administering a statin and/or a selective cholesterol uptake inhibitor; and an effective amount of one or more NRIP1 modulator described herein, where the effective amount of the statin and/or cholesterol uptake inhibitor is lower than the effective amount of a statin or a cholesterol uptake inhibitor administered without the NRIP1 modulator(s). In certain embodiments, the effective amount of the NRIP1 modulator(s) is lower than the effective amount of the NRIP1 modulator administered without the statin and/or cholesterol uptake inhibitor. In certain embodiments, the statin is selected from the group consisting of cerivastatin, atorvastatin, simvastatin, pravastatin, fluvastatin, lovastatin, rosuvastatin, and pitavastatin. The NRIP1 modulator can be administered before, after, or simultaneously with the statin and/or the cholesterol uptake inhibitor. The NRIP1 modulator and/or said statin and/or cholesterol uptake inhibitor can be administered as a unit dosage formulation. In certain embodiments, the administering comprises administering said NRIP1 modulator and/or said statin by a route selected from the group consisting of oral administration, nasal administration, rectal administration, intraperitoneal injection, intravascular injection, subcutaneous injection, transcutaneous administration, and intramuscular injection. The mammal includes, but is not limited to a mammal diagnosed as having one or more symptoms of dislipidemia or diagnosed as at risk for coronary heart disease.

Other further chemotherapeutic agent that may be administered or combined in association with an NRIP1 inhibitor include cardiac agents useful for treating or preventing cardiac-associated medical disorders. These cardiac agents include adrenergic blockers, angiotensin system inhibitor, angiotensin II receptor antagonists, angiotensin-converting enzyme (ACE) inhibitors, calcium channel blockers, antianginal agents, coronary vasodilators, diuretics, adrenergic stimulants and others, including those set forth below:

Adrenergic blockers include those compounds which are β-receptor inhibitors and/or α-receptor inhibitors. Adrenergic blockers which are β-receptor inhibitors include a class of drugs that antagonize the cardiovascular effects of catecholamines in hypertension, angina pectoris, and cardiac arrhythmias. β-adrenergic receptor blockers include, but are not limited to, bunolol hydrochloride (1(2H)-Naphthalenone, 5-[3-(1,1-dimethylethyl)amino]-2-hydroxypropoxy]-3,4-dihydro-,hydrochloride, CAS RN 31969-05-8 which can be obtained from Parke-Davis); acebutolol (±N-[3-Acetyl-4-[2-hydroxy-3-[(1 methylethyl)amino]propoxy]phenyl]-butanamide, or (±)-3'-Acetyl-4'-[2-hydroxy-3-(isopropylamino) propoxy]butyranilide); acebutolol hydrochloride (such as N—P-acetyl-4-[2-hydroxy-3-[1-methyl-ethyle)amino]propoxy]phenyl]-, monohydrocochloride, (±-;-3'-Acetyl-4'-[2-hydroxy-3-(isopropylamino)propoxy]butyranilide monohydrochloride, for example, SECTRAL® Capsules available from Wyeth-Ayerst); alprenolol hydrochloride (2-Propanol, 1-[(1-methylethyl)amino]-3-[2-(2-propenyl)phenoxy]-,hydrochloride, CAS RN 13707-88-5 see Netherlands Patent Application No. 6,605,692); atenolol (such as benzeneacetamide 4-[2'-hydroxy-3'-[(1-methylethyl)amino]propoxy]-, for example, TENORMIN® I.V. Injection available from AstraZeneca); carteolol hydrochloride (such as 5-[3-[(1,1-dimethylethyl)amino]-2-hydroxypropoxy]-3,4-dihydro-2(1H)-quinolinone monohydrochloride, for example, Cartrol® Filmtab® Tablets available from Abbott); Celiprolol hydrochloride (3-[3-Acetyl-4-[3-(tert-butylamino)-2-hydroxypropoxyl]phenyl]-1,1-diethylurea monohydrochloride, CAS RN 57470-78-7, also see in U.S. Pat. No. 4,034,009); cetamolol hydrochloride (Acetamide, 2-[2-[3-[(1,1-dimethylethyl)amino]-2-hydroxypropoxy]-phenoxy]-N-methyl-,monohydrochloride, CAS RN 77590-95-5, see also U.S. Pat. No. 4,059,622); labetalol hydrochloride (such as 5-[1-hydroxy-2-[(1-methyl-3-phenylpropyl)amino]ethyl]salicylamide monohydrochloride, for example, NORMODYNE® Tablets available from Schering; esmolol hydrochloride ((±)-Methyl p-[2-hydroxy-3-(isopropylamino) propoxy]hydrocinnamate hydrochloride, for example, BREVIBLOC® Injection available from Baxter); levobetaxolol hydrochloride (such as (S)-1-[p-[2-(cyclopropylmethoxy)ethyl]phenoxy]-3-(isopropylamino)-2-propanol hydrochloride, for example, BETAXON™ Ophthalmic Suspension available from Alcon); levobunolol hydrochloride (such as (−)-5-[3-(tert-Butylamino)-2-hydroxypropoxy]-3,4-dihydro-1 (2H)-naphthalenone hydrochloride, for example, BETAGAN® Liquifilm® with C CAP® Compliance Cap available from Allergan); nadolol (such as 1-(tert-butylamino)-3-[(5,6,7,8-tetrahydro-cis-6,7-dihydroxy-1-naphthyl)oxy]-2-propanol, for example, Nadolol Tablets available from Mylan); practolol (Acetamide, N-[4-[2-hydroxy-3-[1-methylethyl)amino]-propoxy]phenyl]-, CAS RN 6673-35-4, see also U.S. Pat. No. 3,408,387); propranolol hydrochloride (1-(Isopropylamino)-3-(1-naphthyloxy)-2-propanol hydrochloride CAS RN 318-98-9); sotalol hydrochloride (such as d,l-N-[4-[1-hydroxy-2-[(1-methylethyl)amino]ethyl]-phenyl]methane-sulfonamide monohydrochloride, for example, BETA-PACE AF™ Tablets available from Berlex);timolol (2-Propanol, 1-[(1,1-dimethylethyl)amino]-3-[[4-4(4-morpholinyl)-1,2,5-thiadiazol-3-yl]oxy]-, hemihydrate, (S)—, CAS RN 91524-16-2); timolol maleate (S)-1-[(1,1-dimethylethyl)amino]-3-[[4-(4-morpholinyl)-1,2,5-thiadiazol-3-yl]oxy]-2-propanol (Z)-2-butenedioate (1:1) salt, CAS RN 26921-17-5); bisoprolol (2-Propanol, 1-[4-[[2-(1-methylethoxy)ethoxy]-methyl]phenoxyl]-3-[(1-methylethyl)amino]-, (±), CAS RN 66722-44-9); bisoprolol fumarate (such as (±)-1-[4-[[2-(1-Methylethoxy) ethoxy]methyl]phenoxy]-3-[(1-methylethyl)amino]-2-propanol (E)-2-butenedioate (2:1) (salt), for example, ZEBETA™ Tablets available from Lederle Consumer); nebivalol (2H-1-Benzopyran-2-methanol, ace-kminobis(methylene)]bis[6-fluoro-3,4-dihydro-, CAS RN 99200-09-6 see also U.S. Pat. No. 4,654,362); cicloprolol hydrochloride, such 2-Propanol, 1-[4-[2-(cyclopropylmethoxy)ethoxy]phenoxy]-3-[1-methylethyl) amino]-,hydrochloride, A.A.S. RN 63686-79-3); and dexpropranolol hydrochloride (2-Propanol, 1-[1-methylethyl)-amino]-3-(1-naphthalenyloxy)-hydrochloride (CAS RN 13071-11-9); diacetolol hydrochloride (Acetamide, N-[3-acetyl-4-[2-hydroxy-3-[(1-methyl-ethyl)amino]propoxy] [phenyl]-,monohydrochloride CAS RN 69796-04-9);dilevalol hydrochloride (Benzamide, 2-hydroxy-5-[1-hydroxy-2-[1-methyl-3-phenylpropyl)amino]ethyl]-, monohydrochloride, CAS RN 75659-08-4); exaprolol hydrochloride (2-Propanol, 1-(2-cyclohexylphenoxy)-3-[(1-methylethyl)amino]-,hydrochloride CAS RN 59333-90-3); flestolol sulfate (Benzoic acid, 2-fluoro-,3-[[2-[aminocarbonyl)amino]-1-dimethylethyl]amino]-2-hydroxypropyl ester, (±)-sulfate (1:1) (salt), CAS RN 88844-73-9; metalol hydrochloride (Methanesulfonamide, N-[4-[1-hydroxy-2-(methylamino)propyl]phenyl]-,monohydrochloride CAS RN 7701-65-7);metoprolol 2-Propanol, 1-[4-(2-methoxyethyl)phenoxy]-3-[1-methylethyl)amino]-; CAS RN 37350-58-6); metoprolol tartrate (such as 2-Propanol, 1-[4-(2-methoxyethyl)phenoxy]-3-[(1-methylethyl)amino]-, for example, LOPRESSOR® available from Novartis); pamatolol sulfate (Carbamic acid, [2-[4-[2-hydroxy-3-[(1-methylethyl)amino]propoxyl]phenyl]-ethyl]-,methyl ester, (±) sulfate (salt) (2:1), CAS RN 59954-01-7); penbutolol sulfate (2-Propanol, 1-(2-cyclopentylphenoxy)-3-[1,1-dimethylethyl)amino]1, (S)—, sulfate (2:1) (salt), CAS RN 38363-32-5); practolol (Acetamide, N-[4-[2-hydroxy-3-[(1-methylethyl)amino]-propoxy]phenyl]-, CAS RN 6673-35-4;) tiprenolol hydrochloride (Propanol, 1-[(1-methylethyl) amino]-3-[2-(methylthio)-phenoxy]-, hydrochloride, (±), CAS RN 39832-43-4); tolamolol (Benzamide, 4-[2-[[2-hydroxy-3-(2-methylphenoxy)-propyl]amino]ethoxyl]-, CAS RN 38103-61-6).

Adrenergic receptors which are α-receptor inhibitors act to block vasoconstriction induced by endogenous catecholamines. The resulting fall in peripheral resistance leads to a fall in mean blood pressure. The magnitude of this effect is dependent upon the degree of sympathetic tone at the time the antagonist is administered.

Other inhibitors include, but are not limited to, fenspiride hydrochloride (which may be prepared as disclosed in U.S. Pat. No. 3,399,192 herein incorporated by reference); proroxan (CAS RN 33743-96-3); alfuzosin hydrochloride (CAS RN: 81403-68-1); and labetalol hydrochloride as described above or combinations thereof.

Adrenergic blockers with α and β receptor inhibitor activity which may be used with the present invention include, but are not limited to, bretylium tosylate (CAS RN: 61-75-6); dihydroergtamine mesylate (such as ergotaman-3', 6',18-trione,9,-10-dihydro-12'-hydroxy-2'-methyl-5'-(phenylmethyl)-, (5'(alpha))-, monomethanesulfonate, for example, DHE 45® Injection available from Novartis); carvedilol (such as (±)-1-(Carbazol-4-yloxy)-3-[[2-(o-methoxyphenoxy)ethyl]amino]-2-propanol, for example, COREG® Tablets available from SmithKline Beecham); labetalol (such as 5-[1-hydroxy-2-[(1-methyl-3-phenylpropyl)amino]ethyl] salicylamide monohydrochloride, for example, NORMO-DYNE® Tablets available from Schering); bretylium tosylate (Benzenemethanaminium, 2-bromo-N-ethyl-N,N-dimethyl-, salt with 4-methylbenzenesulfonic acid (1:1) CAS RN 61-75-6); phentolamine mesylate (Phenol, 3-[[(4,5-dihydro-1H-imidazol-2-yl)methyl](4-methylphenyl)amino]-, monomethanesulfonate (salt) CAS RN 65-28-1); solypertine tartrate (5H-1,3-Dioxolo[4,5-f]indole, 7-[2-[4-(2-methoxyphenyl)-1-piperazinyl]ethyl]-, (2R,3R)-2,3-dihydroxybutanedioate (1:1) CAS RN 5591-43-5); zolertine hydrochloride (Piperazine, 1-phenyl-4-[2-(1H-tetrazol-5-yl)ethyl]-, monohydrochloride (8Cl, 9Cl) CAS RN 7241-94-3)

An angiotensin system inhibitor is an agent that interferes with the function, synthesis or catabolism of angiotensin II. These agents which may be used in the present invention include but are not limited to angiotensin-converting enzyme (ACE) inhibitors, angiotensin II antagonists, angiotensin II receptor antagonists, agents that activate the catabolism of angiotensin II and agents that prevent the synthesis of angiotensin I from which angiotensin II is ultimately derived. The renin-angiotensin system is involved in the regulation of hemodynamics and water and electrolyte balance. Factors that lower blood volume, renal profusion, or the concentration of Na+ in plasma tend to activate the system, while factors that increase these parameters tend to suppress its function. Angiotensin I and angiotensin II are synthesized by the enzymatic renin-angiotensin pathway. The synthetic process is initiated when the enzyme renin acts on angiotensinogen, a pseudoglobulin in blood plasma, to produce the cecapeptide angiotensin I. Angiotensin I is converted by angiotensin-converting enzyme (ACE) to angiotensin II. The latter is an active pressor substance which has been implicated as a causative agent in several forms of hypertension in various mammalian species.

Angiotensin II receptor antagonists are compounds which interfere with the activity of angiotensin II by binding to angiotensin II receptors and interfering with its activity. Angiotensin II receptor antagonists which may be used in the present invention are well known and include peptide compounds and non-peptide compounds. Non-limiting examples of angiotensin II receptor antagonists include: candesartan cilexetil (1H-Benzimidazole-7-carboxylic acid, 2-ethoxy-1-[[2'-(1H-tetrazol-5-yl)[1,1'-biphenyl]-4-yl]methyl]-, 1-[[(cyclohexyloxy)carbonyl]oxy]ethyl ester) CAS RN145040-37-5); telmisartan([1,1'-Biphenyl]-2-carboxylic acid, 4'-[(1,4'-dimethyl-2'-propyl[2,6'-bi-1H-benzimidazol]-1'-yl)methyl]-CAS RN144701-48-4); candesartan (1H-Benzimidazole-7-carboxylic acid, 2-ethoxy-1-[[2'-(1H-tetrazol-5-yl)[1,1'-biphenyl]-4-yl]methyl]-CAS RN139481-59-7); losartan potassium (1H-Imidazole-5-methanol, 2-butyl-4-chloro-1-[[2'-(1H-tetrazol-5-yl)[1,1'-biphenyl]-4-yl]methyl]-, monopotassium Irbesartan 1,3-Diazaspiro[4,4]non-1-en-4-one, 2-butyl-3-[[2'-(1H-tetrazol-5-yl)[1,1'-biphenyl]-4-yl]methyl]-CAS RN138402-11-6).

Angiotensin-converting enzyme (ACE), is an enzyme which catalyzes the conversion of angiotensin I to angiotensin II. ACE inhibitors which may be used in the present invention include amino acids and derivatives thereof, peptides, including di and tri peptides and antibodies to ACE which intervene renin-angiotensin system by inhibiting the activity of ACE thereby reducing or eliminating the formation of pressor substance angiotensin II. ACE inhibitors have been used medically to treat hypertension, congestive heart failure, myocardial infarction and renal disease. Suitable ACE inhibitors include, but are not limited to, benazepril hydrochloride (such as 3-[[1-(ethoxycarbonyl)-3-phenyl-(1S)-propyl amino]-2,3,4,5-tetrahydro-2-oxo-1H-1-(3S)-benzazepine-1-acetic acid monohydrochloride, for example, LOTREL® Capsules available from Novartis); captopril (such as 1-[(2S)-3-mercapto-2-methylpropionyl]-L-proline, for example, CAPTOPRIL Tablets available from Mylan); fosinopril (such as L-proline, 4-cyclohexyl-1-[[[2-methyl-1-(1-oxopropoxy) propoxy] (4-phenylbutyl) phosphinyl]acetyl]-, sodium salt, trans-.,for example, MONOPRIL® Tablets available from Bristol-Myers Squibb); moexipril hydrochloride (such as [3S-[2-[R*(R*)],3R*]]-2,2-[[1-(Ethoxycarbonyl)-3-phenyl-propyl]amino]-1-oxopropyl 1-1,2,3,4-tetrahydro-6,7-dimethoxy-3-isoquinolinecarboxylic acid, monohydrochloride, for example, UNIRETIC® Tablets available from Schwarz); perindopril erbumine (such as 2S,3aS,7aS)-1-[(S)—N—[(S)-1-Carboxybutyl]alanyl]hexahydro-2-indolinecarboxylic acid, 1-ethyl ester, compound with tert-butylamine (1:1), for example, ACEON® Tablets available from Solvay); quinapril (such as [3S—[2-[R*(R*)],3R*1]-2-[2-O-(ethoxycarbonyl)-3-phenylpropyl]amino]-1-oxopropyl]-1,2,3,4-tetrahydro-3-isoquinolinecarboxylic acid, monohydrochloride, for example, ACCURETIC® Tablets available from Parke-Davis); ramipril (such as 2-aza-bicyclo[3.3.0]-octane-3-carboxylic acid derivative, for example, ALTACE® Capsules available from Monarch); enalapril maleate (such as (S)-1-[N-[1-(ethoxycarbonyl)-3-phenylpropyl]-L-alanyl]-L-proline, (Z)-2-butenedioate salt (1:1)., for example, VASOTEC® Tablets available from Merck); lisinopril (such as (S)-1-[N 2-(1-carboxy-3-phenylpropyl)-L-lysyl]-L-proline dihydrate, for example, PRINZIDE® Tablets available from Merck); delapril (which may be prepared as disclosed in U.S. Pat. No. 4,385,051); and spirapril (which may be prepared as disclosed in U.S. Pat. No. 4,470,972); benazeprilat (1H-1-Benzazepine-1-acetic acid, 3-[[(1S)-1-carboxy-3-phenylpropyl]amino]-2,3,4,5-tetrahydro-2-oxo-, (3S)-CAS RN 86541-78-8); delapril hydrochloride (Glycine, N-[(1S)-1-(ethoxycarbonyl)-3-phenylpropyl]-L-alanyl-N-(2,3-dihydro-1H-inden-2-yl)-, monohydrochloride CAS RN 83435-67-0); fosinopril sodium (L-Proline, 4-cyclohexyl-1-[[(R)-[(1S)-2-methyl-1-(1-oxopropoxy)propoxy](4-phenylbutyl)phosphinyl]acetyl]-, sodium salt, (4S)-CAS RN 88889-14-9); libenzapril (1H-1-Benzazepine-1-acetic acid, 3-[[(1S)-5-amino-1-carboxypentyl]amino]-2,3,4,5-tetrahydro-2-oxo-, (3S)-CAS RN109214-55-3); pentopril (1H-Indole-1-pentanoic acid, 2-carboxy-2,3-dihydro-.alpha., .gamma.-dimethyl-.delta.-oxo-, .alpha.-ethyl ester, (.alpha.R, .gamma.R,2S)-CAS RN 82924-03-6); perindopril 1H-Indole-2-carboxylic acid, 1-[(2S)-2-[[(1S)-1-(ethoxycarbonyl)butyl]amino]-1-oxopropyl]octahydro-, (2S,3aS, 7aS)—CAS RN 82834-16-0); quinapril hydrochloride (3-Isoquinolinecarboxylic acid, 2-[(2S)-2-[[(1S)-1-(ethoxycarbonyl)-3-phenylpropyl]amino]-1-oxopropyl]-1,2,3,4-tetrahydro-, monohydrochloride, (3S)-CAS RN 82586-55-); quinaprilat (3-Isoquinolinecarboxylic acid, 2-[(2S)-2-[[(1S)-1-carboxy-3-phenylpropyl]amino]-1-oxopropyl]-1,2,3,4-tetrahydro-, (3S)-CAS RN 82768-85-2); spirapril hydrochloride (1,4-Dithia-7-azaspiro[4,4]nonane-8-carboxylic acid, 7-[(2S)-2-[[(1S)-1-(ethoxycarbonyl)-3-phenylpropyl] amino]-1-oxopropyl]-, monohydrochloride, (8S)-CAS RN 94841-17-5); spiraprilat 1(,4-Dithia-7-azaspiro[4,4]nonane-8-carboxylic acid, 7-[(2S)-2-[[(1S)-1-carboxy-3-phenylpropyl]amino]-1-oxopropyl], (8S)-CAS RN 83602-05-5); teprotide (Bradykinin potentiator BPP9a CAS RN 35115-60-7); lisinopril (L-Proline, N2-[(1S)-1-carboxy-3-phenylpropyl]-L-lysyl-CAS RN 76547-98-3); zofenopril (L-Proline, 1-[(2S)-3-(benzoylthio)-2-methyl-1-oxopropyl]-4-(phenylthio)-, calcium salt (2:1), (4S)-CAS RN 81938-43-4).

"Calcium channel blockers" are a chemically diverse class of compounds having important therapeutic value in the control of a variety of diseases including several cardiovascular disorders such as hypertension, angina, and cardiac arrhythmias (Fleckenstein, Cir. Res. V. 52 (suppl. 1), p. 13-16 (1983); Fleckenstein, *Experimental Facts and Therapeutic Prospects*, John Wiley, New York (1983); McCall, D., *Curr. Pract Cardiol.*, v. 10, p. 1-11 (1985)). Calcium channel blockers are a heterogeneous group of drugs that prevent or slow the entry of calcium into cells by regulating cellular calcium channels (Remington, *The Science and Practice of Pharmacy*, Nineteenth Edition, Mack Publishing Company, Eaton, Pa., p. 963 (1995)). Calcium channel blockers useful in the present invention include but are not limited to, the besylate salt of amlodipine (such as 3-ethyl-5-methyl-2-(2-aminoethoxymethyl)-4-(2-chlorophenyl)-1,4-dihydro-6-methyl-3,5-pyridinedicarboxylate benzenesulphonate, for example, NORVASC® available from Pfizer); clentiazem maleate (1,5-Benzothiazepin-4(5H)-one, 3-(acetyloxy)-8-chloro-5-[2-

(dimethylamino)ethyl]-2,3-dihydro-2-(4-methoxyphenyl)-(2S-cis)-, (Z)-2-butenedioate (1:1), see also U.S. Pat. No. 4,567,195); isradipine (3,5-Pyridinedicarboxylic acid, 4-(4-benzofurazanyl)-1,4-dihydro-2,6-dimethyl-,methyl 1-methylethyl ester, (±)-4(4-benzofurazanyl)-1,4-dihydro-2,6-dimethyl-3,5-pyridinedicarboxylate, see also U.S. Pat. No. 4,466,972); nimodipine (such as isopropyl (2 methoxyethyl) 1,4-dihydro-2,6-dimethyl-4-(3-nitrophenyl)-3,5-pyridinedicarboxylate, for example, NIMOTOP® available from Bayer); felodipine (such as ethyl methyl 4-(2,3-dichlorophenyl)-1,4-dihydro-2,6-dimethyl-3,5-pyridinedicarboxylate, for example, PLENDIL® Extended-Release Tablets available from AstraZeneca LP); nilvadipine (3,5-Pyridinedicarboxylic acid, 2-cyano-1,4-dihydro-6-methyl-4-(3-nitrophenyl)-,3-methyl 5-(1-methylethyl) ester, also see U.S. Pat. No. 3,799,934); nifedipine (such as 3,5-pyridinedicarboxylic acid,1,4-dihydro-2,6-dimethyl-4-(2-nitrophenyl)-, dimethyl ester, for example, PROCARDIA XL® Extended Release Tablets available from Pfizer); diltiazem hydrochloride (such as 1,5-Benzothiazepin-4(5H)-one, 3-(acetyloxy)-5-[2-(dimethylamino)ethyl]-2,-3-dihydro-2(4-methoxyphenyl)-, monohydrochloride, (+)-cis., for example, TIAZAC® Capsules available from Forest); verapamil hydrochloride (such as benzeneacetonitrile, (alpha)-[[3-[[2-(3,4-dimethoxyphenyl)ethyl]methylamino]propyl]-3,4-dimethoxy-(alpha)-(1-methylethyl)hydrochloride, for example, ISOPTIN® SR Tablets available from Knoll Labs); teludipine hydrochloride (3,5-Pyridinedicarboxylic acid, 2-[(dimethylamino)methyl]-4-[2-[(1E)-3-(1,1-dimethylethoxy)-3-oxo-1-propenyl]phenyl]-1,4-dihydro-6-methyl-, diethyl ester, monohydrochloride) CAS RN 108700-03-4); belfosdil (Phosphonic acid, [2-(2-phenoxyethyl)-1,3-propanediyl]bis-, tetrabutyl ester CAS RN103486-79-9); fostedil (Phosphonic acid, [[4-(2-benzothiazolyl)phenyl]methyl]-, diethyl ester CAS RN 75889-62-2).

Cardiovascular agents of the present invention which also act as "anti-anginal agents" are useful in the present invention. Angina includes those symptoms that occur when myocardial oxygen availability is insufficient to meet myocardial oxygen demand. Non-limiting examples of these agents include: ranolazine (hydrochloride1-piperazineacetamide, N-(2,6-dimethylphenyl)-4-[2-hydroxy-3-(2-methoxyphenoxy)propyl]-, dihydrochloride CAS RN 95635-56-6); betaxolol hydrochloride (2-Propanol, 1-[4-[2 (cyclopropylmethoxy)ethyl]phenoxy]-3-[(1-methylethyl)amino]-, hydrochloride CAS RN 63659-19-8); butoprozine hydrochloride (Methanone, [4-[3(dibutylamino)propoxy]phenyl](2-ethyl-3-indolizinyl)-, monohydrochloride CAS RN 62134-34-3); cinepazet maleate1-Piperazineacetic acid, 4-[1-oxo-3-(3,4,5-trimethoxyphenyl)-2-propenyl]-, ethyl ester, (2Z)-2-butenedioate (1:1) CAS RN 50679-07-7); tosifen (Benzenesulfonamide, 4-methyl-N-[[[(1S)-1-methyl-2-phenylethyl]amino]carbonyl]-CAS RN 32295-18-4); verapamilhydrochloride (Benzeneacetonitrile, .alpha.-[3-[[2-(3,4-dimethoxyphenyl) ethyl]methylamino]propyl]-3,4-dimethoxy-.alpha.-(1-methylethyl)-, monohydrochloride CAS RN 152-11-4); molsidomine (1,2,3-Oxadiazolium, 5-[(ethoxycarbonyl)amino]-3-(4-morpholinyl)-, inner salt CAS RN 25717-80-0); ranolazine hydrochloride (1-piperazineacetamide, N-(2,6-dimethylphenyl)-4-[2-hydroxy-3-(2-methoxyphenoxy)propyl]-, dihydrochloride CAS RN 95635-56-6); tosifen (Benzenesulfonamide, 4-methyl-N-[[[(1S)-1-methyl-2-phenylethyl]amino]carbonyl]-CAS RN 32295-18-4).

"Coronary vasodilators" may act to reduce angina systems by increasing the oxygen supply to the heart. Coronary vasodilators useful in the present invention include, but are not limited to, diltiazem hydrochloride (such as 1,5-Benzothiazepin-4(5H)-one, 3-(acetyloxy)-5[2-(dimethylamino) ethyl]-2,-3-dihydro-2(4-methoxyphenyl)-, monohydrochloride, (+)-cis, for example, TIAZAC® Capsules available from Forest); isosorbide dinitrate (such as 1,4:3,6-dianhydro-D-glucitol 2,5-dinitrate, for example, ISORDIL® TITRADOSE® Tablets available from Wyeth-Ayerst); sosorbide mononitrate (such as 1,4:3,6-dianhydro-D-glucitol,5-nitrate, an organic nitrate, for example, lsmo® Tablets available from Wyeth-Ayerst); nitroglycerin (such as 2,3 propanetriol trinitrate, for example, NITROSTAT® Tablets available from Parke-Davis); verapamil hydrochloride (such as benzeneacetonitrile, (±)-(alpha)[3[[2-(3,4 dimethoxyphenyl)ethyl]methylamino]propyl]-3,4-dimethoxy-(alpha)-(1-methylethyl) hydrochloride, for example, COVERA HS® Extended-Release Tablets available from Searle); chromonar (which may be prepared as disclosed in U.S. Pat. No. 3,282,938); clonitate (Annalen 1870 155); droprenilamine (which may be prepared as disclosed in German Patent No. 2,521,113); lidoflazine (which may be prepared as disclosed in U.S. Pat. No. 3,267,104); prenylamine (which may be prepared as disclosed in U.S. Pat. No. 3,152,173); propatyl nitrate (which may be prepared as disclosed in French Patent No. 1,103,113); mioflazine hydrochloride (1-piperazineacetamide, 3-(aminocarbonyl)-4-[4,4-bis(4-fluorophenyl)butyl]-N-(2,6-dichlorophenyl)-, dihydrochloride CAS RN 83898-67-3); mixidine (Benzeneethanamine, 3,4-dimethoxy-N-(1-methyl-2-pyrrolidinylidene)-Pyrrolidine, 2-[(3,4-dimethoxyphenethyl)imino]-1-methyl-1-Methyl-2-[(3,4-dimethoxyphenethyl)imino]pyrrolidine CAS RN 27737-38-8); molsidomine (1,2,3-Oxadiazolium, 5-[(ethoxycarbonyl)amino]-3-(4-morpholinyl)-, inner salt CAS RN 25717-80-0); isosorbide mononitrate (D-Glucitol, 1,4:3,6-dianhydro-, 5-nitrate CAS RN16051-77-7); erythrityl tetranitrate (1,2,3,4-Butanetetrol, tetranitrate, (2R,3S)-rel-CAS RN 7297-25-8); clonitrate(1,2-Propanediol, 3-chloro-, dinitrate (7Cl, 8Cl, 9Cl) CAS RN 2612-33-1); dipyridamole Ethanol, 2,2',", 2'"-[(4,8-di-1 piperidinylpyrimido[5,4-d]pyrimidine-2,6-diyl) dinitrilo]tetrakis-CAS RN 58-32-2); nicorandil (CAS RN 65141-46-0 3-); pyridinecarboxamide (N-[2-(nitrooxy) ethyl]-Nisoldipine-3,5-Pyridinedicarboxylic acid, 1,4-dihydro-2,6-dimethyl-4-(2-nitrophenyl)-, methyl 2-methylpropyl ester CAS RN 63675-72-9); nifedipine-3,5-Pyridinedicarboxylic acid, 1,4-dihydro-2,6-dimethyl-4-(2-nitrophenyl)-, dimethyl ester CAS RN 21829-25-4); perhexyline maleate (Piperidine, 2-(2,2-dicyclohexylethyl)-, (2Z)-2-butenedioate (1:1) CAS RN 6724-53-4); oxprenolol hydrochloride2-Propanol, 1-[(1-methylethyl)amino]-3-[2-(2-propenyloxy)phenoxy]-, hydrochloride CAS RN 6452-73-9); pentrinitrol (1,3-Propanediol, 2,2-bis[(nitrooxy)methyl]-, mononitrate (ester) CAS RN1607-17-6); verapamil (Benzeneacetonitrile, .alpha.-[3-[[2-(3,4-dimethoxyphenyl)ethyl]methylamino] propyl]-3,4-dimethoxy-.alpha.-(1-methylethyl)-CAS RN 52-53-9).

The term "diuretic" includes compounds that increase the excretion of solutes (mainly NaCl) and water. In general, the primary goal of diuretic therapy is to reduce extracellular fluid volume in order to lower blood pressure or rid the body of excess interstitial fluid (edema). Non-limiting examples of diuretics which may be used within the scope of this invention include althiazide (which may be prepared as disclosed in British Patent No. 902,658); benzthiazide (which may be prepared as disclosed in U.S. Pat. No. 3,108,097); buthiazide (which may be prepared as disclosed in British Patent Nos. 861,367); chlorothiazide (which may be prepared as disclosed in U.S. Pat. No. 2,809,194); spironolactone (CAS Number 52-01-7); and triamterene (CAS Number 396-01-0).

"Adrenergic stimulants" useful as cardiovascular agents in the present invention include, but are not limited to, guanfacine hydrochloride (such as N-amidino-2-(2,6-dichlorophenyl) acetamide hydrochloride, for example, TENEX® Tablets available from Robins); methyldopa-hydrochlorothiazide (such as levo-3-(3,4-dihydroxyphenyl)-2-methylalanine) combined with Hydrochlorothiazide (such as 6-chloro-3,4-dihydro-2H-1,2,4-benzothiadiazine-7-sulfonamide 1,1-dioxide, for example, the combination as, for example, ALDORIL® Tablets available from Merck); methyldopa-chlorothiazide (such as 6-chloro-2H-1,2,4-benzothiadiazine-7-sulfonamide 1,1-dioxide and methyldopa as described above, for example, ALDOCLORr® Tablets available from Merck); clonidine hydrochloride (such as 2-(2,6-dichlorophenylamino)-2-imidazoline hydrochloride and chlorthalidone (such as 2-chloro-5-(1-hydroxy-3-oxo-1-isoindolinyl) benzenesulfonamide), for example, COMBIPRES® Tablets available from Boehringer Ingelheim); clonidine hydrochloride (such as 2-(2,6-dichlorophenylamino)-2-imidazoline hydrochloride, for example, CATAPRES® Tablets available from Boehringer Ingelheim); clonidine (1H-Imidazol-2-amine, N-(2,6-dichlorophenyl)-4,5-dihydro-CAS RN 4205-90-7).

Further chemotherapeutic agents include fish oil, eicosapenanoic acid, docosahexanoic acid, linoleic acid, niacin, fibrates such as fenofibrate, gemfibrozil and bile acid sequestrants such as cholestyramine, colestipol and colesevelam.

Other chemotherapeutic agents include althiazide (2H-1,2,4-Benzothiadiazine-7-sulfonamide, 6-chloro-3,4-dihydro-3-[(2-propenylthio)methyl]-, 1,1-dioxide CAS RN 5588-16-9); benzthiazide (2H-1,2,4-Benzothiadiazine-7-sulfonamide, 6-chloro-3-[[(phenylmethyl)thio]methyl]-, 1,1-dioxide CAS RN 91-33-8); captopril (L-Proline, 1-[(2S)-3-mercapto-2-methyl-1-oxopropyl]-CAS RN 62571-86-2); carvedilol (2-Propanol, 1-(9H-carbazol-4-yloxy)-3-[[2-(2-methoxyphenoxy)ethyl]amino]-CAS RN 72956-09-3), chlorothiazide (sodium 2-Propanol, 1-(9H-carbazol-4-yloxy)-3-[[2-(2-methoxyphenoxy)ethyl]amino]-CAS RN 72956-09-3); clonidine hydrochloride (1H-Imidazol-2-amine, N-(2,6-dichlorophenyl)-4,5-dihydro-, monohydrochloride CAS RN 4205-91-8); cyclothiazide (2H-1,2,4-Benzothiadiazine-7-sulfonamide, 3-bicyclo[2.2.1]hept-5-en-2-yl-6-chloro-3,4-dihydro-, 1,1-dioxide CAS RN 2259-96-3); delapril hydrochloride (2H-1,2,4-Benzothiadiazine-7-sulfonamide, 3-bicyclo[2.2.1]hept-5-en-2-yl-6-chloro-3,4-dihydro-, 1,1-dioxide CAS RN 2259-96-3); difevalol hydrochloride (2H-1,2,4-Benzothiadiazine-7-sulfonamide, 3-bicyclo[2.2.1]hept-5-en-2-yl-6-chloro-3,4-dihydro-, 1,1-dioxide CAS RN 2259-96-3); delapril hydrochloride (Glycine, N—R1S)-1-(ethoxycarbonyl)-3-phenylpropyl]-L-alanyl-N-(2,3-dihydro-1H-inden-2-yl)-, monohydrochloride CAS RN 83435-67-0); doxazosin mesylate (piperazine, 1-(4-amino-6,7-dimethoxy-2-quinazolinyl)-4-[(2,3-dihydro-1,4-benzodioxin-2-yl)carbonyl]-, monomethanesulfonate CAS RN 77883-43-3); fosinopril sodium (L-Proline, 4-cyclohexyl-1-[[(R)-[(1S)-2-methyl-1-(1-oxopropoxy)propox); moexipril hydrochloride (3-Isoquinolinecarboxylic acid, 2-[(2S)-2-[[(1S)-1-(ethoxycarbonyl)-3-phenylpropyl]amino]-1-oxopropyl]-1,2,3,4-tetrahydro-6,7-dimethoxy-, monohydrochloride, (3S)-CAS RN 82586-52-5); monatepil maleate (1-piperazinebutanamide, N-(6,11-dihydrodibenzo(b,e)thiepin-11-yl)-4-(4-fluorophenyl)-, (±)-, (Z)-2-butenedioate (1:1) (±)—N-(6,11-Dihydrodibenzo(b,e)thiepin-11-yl)-4-(p-fluorophenyl)-1-piperazinebutyramide maleate (1:1) CAS RN132046-06-1), Metoprolol succinate (Butanedioic acid, compd. with 1-[4-(2-methoxyethyl)phenoxy]-3-[(1-methylethyl)amino]-2-propanol (1:2) CAS RN 98418-47-4); guanfacine hydrochloride (Benzeneacetamide, N-(aminoiminomethyl)-2,6-dichloro-, monohydrochloride CAS RN 29110-48-3; methyldopa (L-Tyrosine, 3-hydroxy-.alpha.-methyl-CAS RN 555-30-6); quinaprilat (3-Isoquinolinecarboxylic acid, 2-[(2S)-2-[[(1S)-1-carboxy-3-phenylpropyl]amino]-1-oxopropyl]-1,2,3,4-tetrahydro-, (3S)-CAS RN 82768-85-2); quinapril hydrochloride (3-Isoquinolinecarboxylic acid, 2-[(2S)-2-[[(1S)-1-(ethoxycarbonyl)-3-phenylpropyl]amino]-1-oxopropyl]-1,2,3,4-tetrahydro-, monohydrochloride, (3S)-CAS RN 82586-55-8); Primidolol (2,4(1H,3H)-Pyrimidinedione, 1424µ-hydroxy-3-(2-methylphenoxy)propyl]amino]ethyl]-5-methyl-CAS RN 67227-55-8); prazosin hydrochloride (piperazine, 1-(4-amino-6,7-dimethoxy-2-quinazolinyl)-4-(2-furanylcarbonyl)-, monohydrochloride CAS RN19237-84-4); pelanserin hydrochloride 2,4(1H,3H)-Quinazolinedione, 3-[3-(4-phenyl-1-piperazinyl)propyl]-, monohydrochloride CAS RN 42877-18-9); phenoxybenzamine hydrochloride (Benzenemethanamine, N-(2-chloroethyl)-N-(1-methyl-2-phenoxyethyl)-, hydrochloride CAS RN 63-92-3); candesartan cilexetil (1H-Benzimidazole-7-carboxylic acid, 2-ethoxy-1-[[2'-(1H-tetrazol-5-yl)[1,1'-biphenyl]-4-yl]methyl]-, 1-[[(cyclohexyloxy)carbonyl]oxy]ethyl ester CAS RN145040-37-5); telmisartan (1,1'-Biphenyl]-2-carboxylic acid, 4'-[(1,4'-dimethyl-2'-propyl[2,6'-bi-1H-benzimidazol]-1'-yl)methyl]-CAS RN144701-48-4); candesartan1H-Benzimidazole-7-carboxylic acid, 2-ethoxy-1-[[2'-(1H-tetrazol-5-yl)[1,1'-biphenyl]-4-yl]methyl]-CAS RN139481-59-7); amlodipine besylate-3,5-Pyridinedicarboxylic acid, 2-[(2-aminoethoxy)methyl]-4-(2-chlorophenyl)-1,4-dihydro-6-methyl-, 3-ethyl 5-methyl ester, monobenzenesulfonate CAS RN111470-99-6 Amlodipine maleate 3,5-Pyridinedicarboxylic acid, 2-[(2-aminoethoxy)methyl]-4-(2-chlorophenyl)-1,4-dihydro-6-methyl-, 3-ethyl 5-methyl ester, (2Z)-2-butenedioate (1:1) CAS RN 88150-47-4); terazosin hydrochloride (Piperazine, 1-(4-amino-6,7-dimethoxy-2-quinazolinyl)-4-[(tetrahydro-2-furanyl)carbonyl]-, monohydrochloride CAS RN 63074-08-8); bevantolol hydrochloride (2-Propanol, 1-[[2-(3,4-dimethoxyphenyl)ethyl]amino]-3-(3-methylphenoxy)-, hydrochloride CAS RN 42864-78-8); ramipril (Cyclopenta[b]pyrrole-2-carboxylic acid, 1-[(2S)-2-[[(1S)-1-(ethoxycarbonyl)-3-phenylpropyl]amino]-1-oxopropyl]octahydro-, (2S,3aS,6aS)—CAS RN 87333-19-5).

EXAMPLES

This section is intended to further exemplify and clarify the present invention and is not a limitation thereof. Any novel method or composition set forth herein is within the scope of the present invention.

Example 1

RNAi Functional Knockdown of NRIP1 Increases apoA1 mRNA and apoA1 Secreted Protein in Human Hepatocytoma HepG2 and Huh7 Cells In this example, pools of 4 gene-specific siRNA molecules targeting 33 different transcription modulators were evaluated for their ability to increase apoA1 mRNA and apoA1 secreted protein in human hepatocellular carcinoma (HepG2) cells.

Pools of siRNAs that were targeted to NRIP1 (#27) and 32 other transcription modulators were transfected into cultured HepG2 cell along with experimental controls apoA1 siRNA (siApoA1), siRNA non-targeting control (siNT) and transfection media without siRNA (HepG2). For each transcriptional modulator, four independent siGenome ON-TARGET plus annealed duplex short interfering RNAs (siRNA) were pooled at equal molar concentrations. Each siRNA was designed and synthesized by Dharmacon to interact in a sequence specific manner with the target mRNA and suppress gene expression. For NRIP1, the following siRNA duplexes were used based on the NRIP1 sequence found under GenBank Accession no. NM_173440.

5 sense GAAGCGUGCUAACGAUAAAUU (SEQ ID NO: 7)
antisense 5'P-UUUAUCGUUAGCACGCUUCUU (SEQ ID NO: 12)
6 sense AGAAGGAUGUUGGCAGUUAUU (SEQ ID NO: 8)
antisense 5'P-UAACUGCCAACAUCCUUCUUU (SEQ ID NO: 13)
7 sense GGACUGGAAUGCAGCAAAGUU (SEQ ID NO: 14)
antisense 5'P-CUUUGCUGCAUUCCAGUCCUU (SEQ ID NO: 15)
8 sense AUACGAAUCUUCCUGAUGUUU (SEQ ID NO: 9)
antisense 5'P-ACAUCAGGAAGAUUCGUAUUU (SEQ ID NO: 16)

Cultured human hepatoma cell line HepG2 cells were seeded in 6-well plates at a density of 4E5 (i.e., 4×10$^5$) cells/well in antibiotic free 10% FBS/MEME and cultured for 16 hours. siRNA (20 µM) was prepared by diluting to 2 µM with buffer. To that, equal amounts Opti-MEM medium was added, mixed and kept at room temperature (RT) for 5 minutes. Transfection lipid was prepared using DharmaFECT 4 transfection reagent X25 times diluted with Opti-MEM medium (4 µL/100 medium), mixed and kept at RT for 5 minutes. siRNA and transfection lipid were complexed by mixing equal volumes and incubated for 20 minutes at RT. Cultured HepG2 cells in 6-sell plates were changed into fresh antibiotic free 10% FBS/MEME (1.6 mL/well) and 400 complexed siRNA was added to each well to a final concentration of 100 nM and incubated for 48 hrs.

Forty-eight hours post transfection, medium was removed from transfected HepG2 culture and assessed for secreted apoA1 levels using a human apoA1 sandwich ELISA (MabTech) as described by the manufacturer. Adherent cells were washed twice with PBS and total RNA isolated using RNeasy lipid tissue mini kit (Qiagen) according to the manufacturer. RT-qPCR was performed as described (Zhu et al., *Analytical Biochemistry* 345:102-109 (2005)) using the following apoA1 specific primer/probes: Forward 5'-GACCTCCACCTTCAGCAAGCT (SEQ ID NO: 17), Reverse 5'-CCTTTTCCAGGTTATCCCAGAA (SEQ ID NO: 18), Probe 5'-[6-FAM] AGCTCGGCCCTGTGACCCAGGA (SEQ ID NO: 19) [TAMRA-6-FAM].

Treatment of cells with the RNAi pool that targeted NRIP1 (#27) resulted in an increase in apoA1 mRNA level and apoA1 protein production as compared to observed control levels (FIG. 1). These data demonstrate that inhibition of NRIP1 (e.g., inhibition of expression using siRNA) increases the expression of apoA1 mRNA and secreted protein. Thus, mechanisms that inhibit NRIP1 are effective for increasing apoA1 plasma levels and HDL levels and are useful for treating disorders in which it is desirable to increase such apoA1/HDL levels (e.g., dyslipidemia, atherosclerosis and coronary heart disease).

Figure 2:
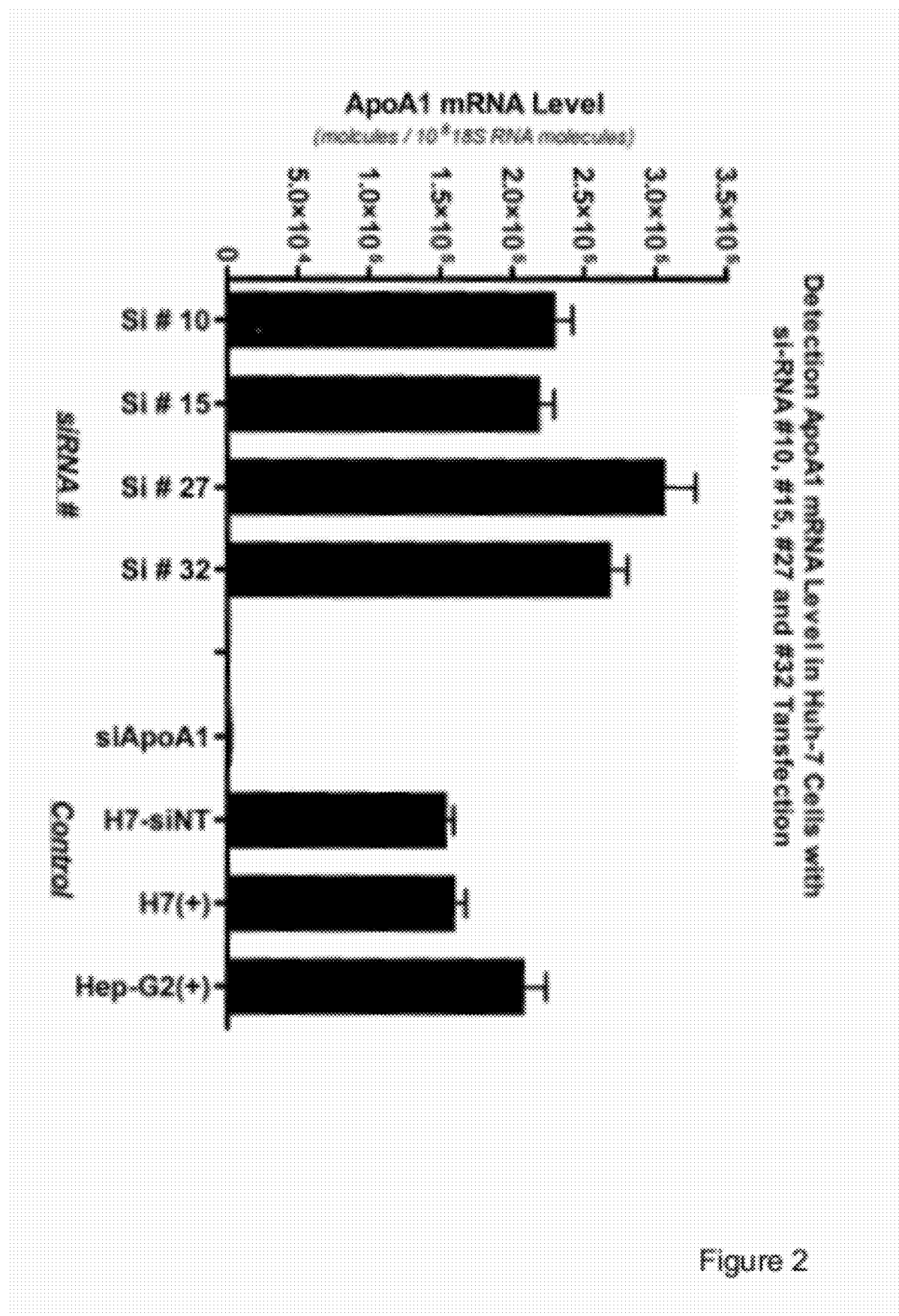
FIG. 2 is a bar graph illustrating the effect of RNAi functional knock down of transcription modulators on apoA1 production in Huh7 cells.

To validate the observed changes in HepG2 cells, Huh7 cells were treated with four positive siRNA pools identified in FIG. 1. Included was the NRIP1 siRNA pool (#27). In this experiment, treatment of Huh7 with all four siRNAs also produced increases in apoA1 gene expression at levels consistent with the results in HepG2 cells (FIG. 2).

Example 2

Increase of apoA1 Expression Through Loss of NRIP1 Functions Independently of the RXR Mechanism The data in Example 1 demonstrated that HepG2 cells transfected with siRNA #27 led to an increase in both apoA1 mRNA and subsequent apoA1 secreted protein. This example examines the siRNA dose response in HepG2 cells in the presence of 10 µM 9 cis-retinoic acid (9CRA).

HepG2 cells were transfected with varying concentrations of pooled NRIP1 siRNA as described in Example 1, except that 24 hours post transfection 10 µM 9 cis-retinoic acid was added to the growth medium. Cells were harvested 24 hours later and apoA1 and NRIP1 mRNA levels measured as previously described. RT-qPCR was performed as described (Zhu et al., *Analytical Biochemistry* 345:102-109 (2005)) using the following NRIP1 specific primer/probes:

Forward 5'-TGCTACAGACCTATGTGTTAGGAA (SEQ ID NO: 20);
Reverse 5'-CAGTGCTGATCAACTTCTACGC (SEQ ID NO: 21);
Probe 5'-CTCCTCCT (SEQ ID NO: 22).

Figure 3:
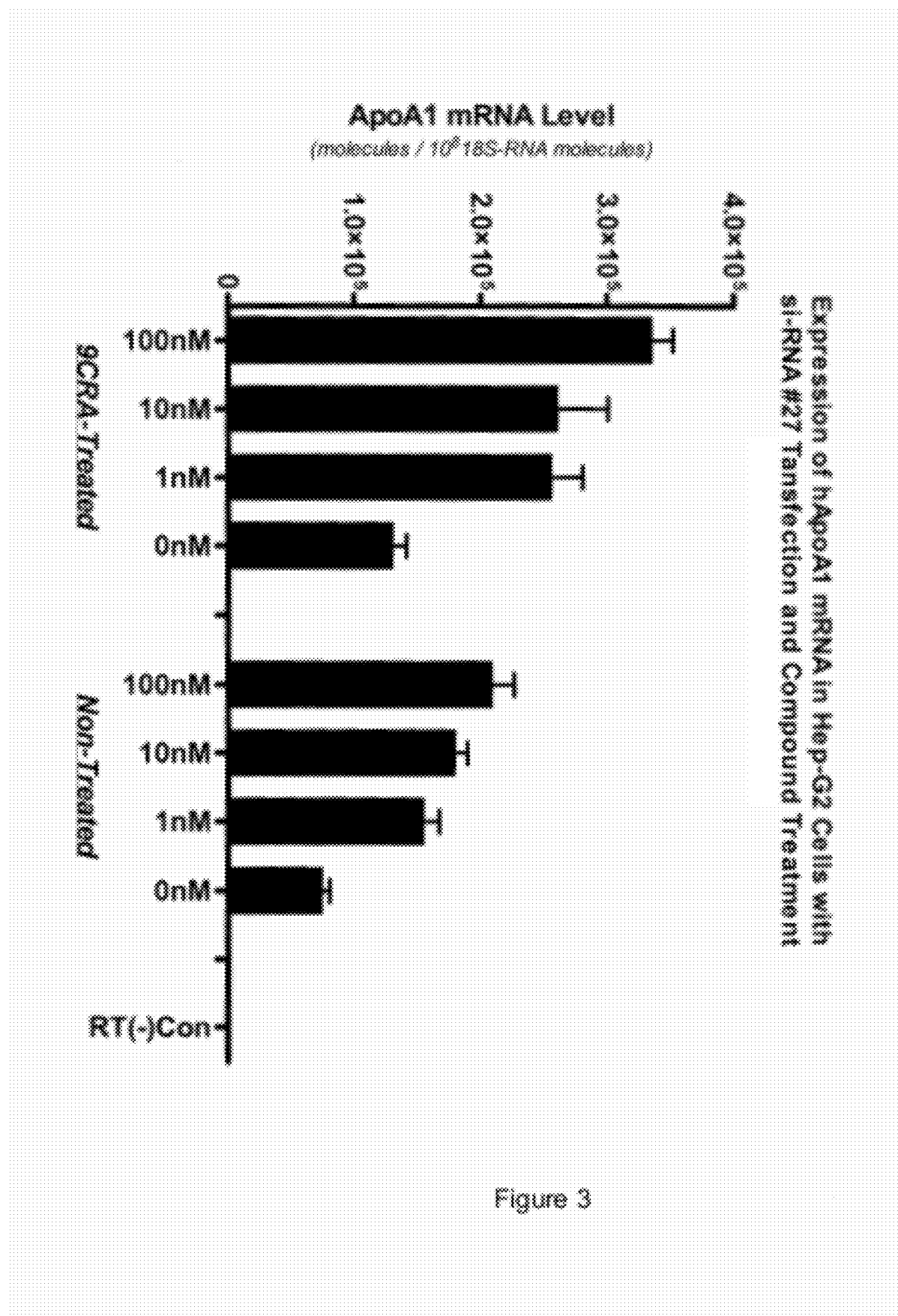
FIG. 3 is a bar graph illustrating a dose dependent increase of apoA1 mRNA following transfection with NRIP1 siRNA in HepG2 cells, in the absence and presence of 9-cis retinoic acid (9CRA).
Figure 4:
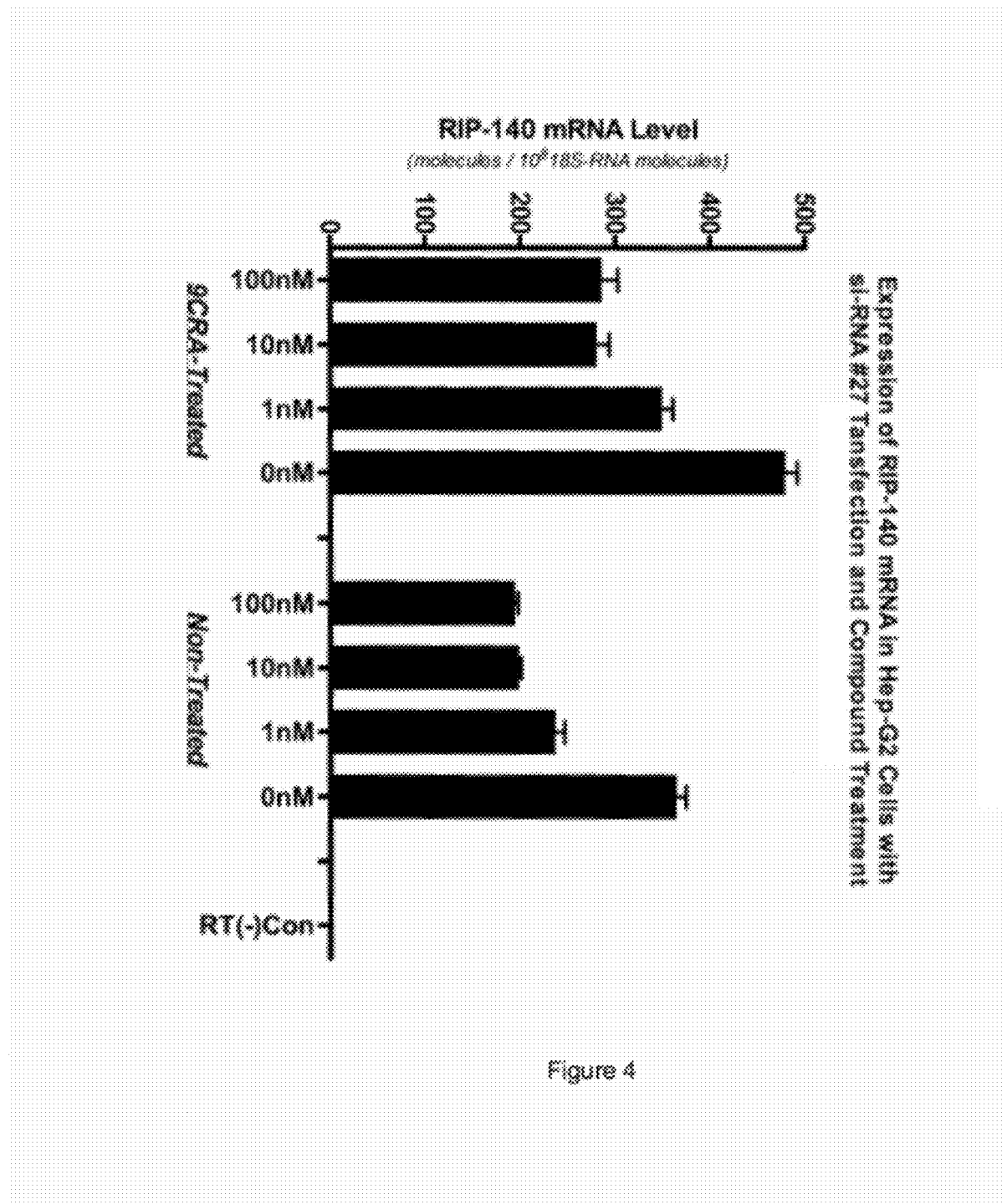
FIG. 4 is a bar graph illustrating a dose dependent decrease of NRIP1 target mRNA levels following transfection with NRIP1 siRNA in HepG2 cells, in the absence and presence of 9-cis retinoic acid (9CRA).

FIG. 3 showed that the increase in apoA1 mRNA levels following treatment with the pooled NRIP1 siRNA occurred in a dose dependent manner, as indicated in the panel marked "non-treated". Further analysis showed a consistent inhibition of NRIP1 gene expression following NRIP1 siRNA in a dose-dependent manner which also persisted following in the treatment with 9CRA (FIG. 4).

It has been established that 9CRA stimulates endogenous apoA1 gene expression in HepG2 cells (Haghpassand et al., *Atherosclerosis* 117:199-207 (1995)). All-trans and 9-cis isomers of retinoic acid are potent modulators for a broad spectrum of essential biological activities. The action of retinoids is mediated by different homo- or heterodimeric versions of retinoic acid/retinoid X receptors, which belong to the nuclear receptor superfamily of ligand activated transcription factors. Each of these receptors has three distinct subtypes namely RARα, β, γ and RXRα, β, γ, which form heterodimers with each other. Furthermore, these receptor subtypes also have isoforms, which can generate theoretically 48 different RXR/RAR heterodimeric forms. It is highly suggestive that the undesirable side effects of retinoids are in part due to the formation of homo- and heterodimers of these receptor subtypes or isoforms, which modulate the expression of different target genes in response to the same or different naturally occurring retinoids.

Several members of the nuclear receptor superfamily including RXR bind to a specific retinoic acid response element of the apoAI promoter. Modulation of transcriptional activation of the apoAI gene by different homo- and heterodimeric forms of RXR or RAR can be affected by several factors including the relative position of the response element and the affinity of the activated nuclear receptor for the response element. For example, both RARα and RARβ form heterodimers with RXRα and bind to the apoA1 promoter with high affinity while RARα alone does not bind to site A of the apoA1 promoter, whereas binding of RARβ to site A is ligand-dependent. The DNA-binding correlates with the transcriptional data, which indicates that RARβ but not RARα activates transcription from site A in response equally well to 9-cis and all-trans retinoic acids. 9-cis RA is a more potent ligand than all-trans RA to activate transcription via RXR/RAR heterodimers.

Here we demonstrated that inhibition of NRIP1 gene expression by siRNA results in apoA1 gene expression in an independent manner from the retinoid-induced RXR/RAR mechanism (FIG. 3).

Example 3

Treatment with Individual NRIP1 siRNAs Results in Decreased NRIP1 Target mRNA and Increased apoA1 mRNA The data described in Example 1 showed that transfection with a pool of 4 to siRNA molecules targeted to NRIP1 resulted in an increase in apoA1 mRNA level and apoA1 protein production as compared to the level observed in control cells (FIG. 1). We next investigated the NRIP1 inhibitory effect of the individual NRIP1 siRNAs in HepG2 cells.

Figure 5:
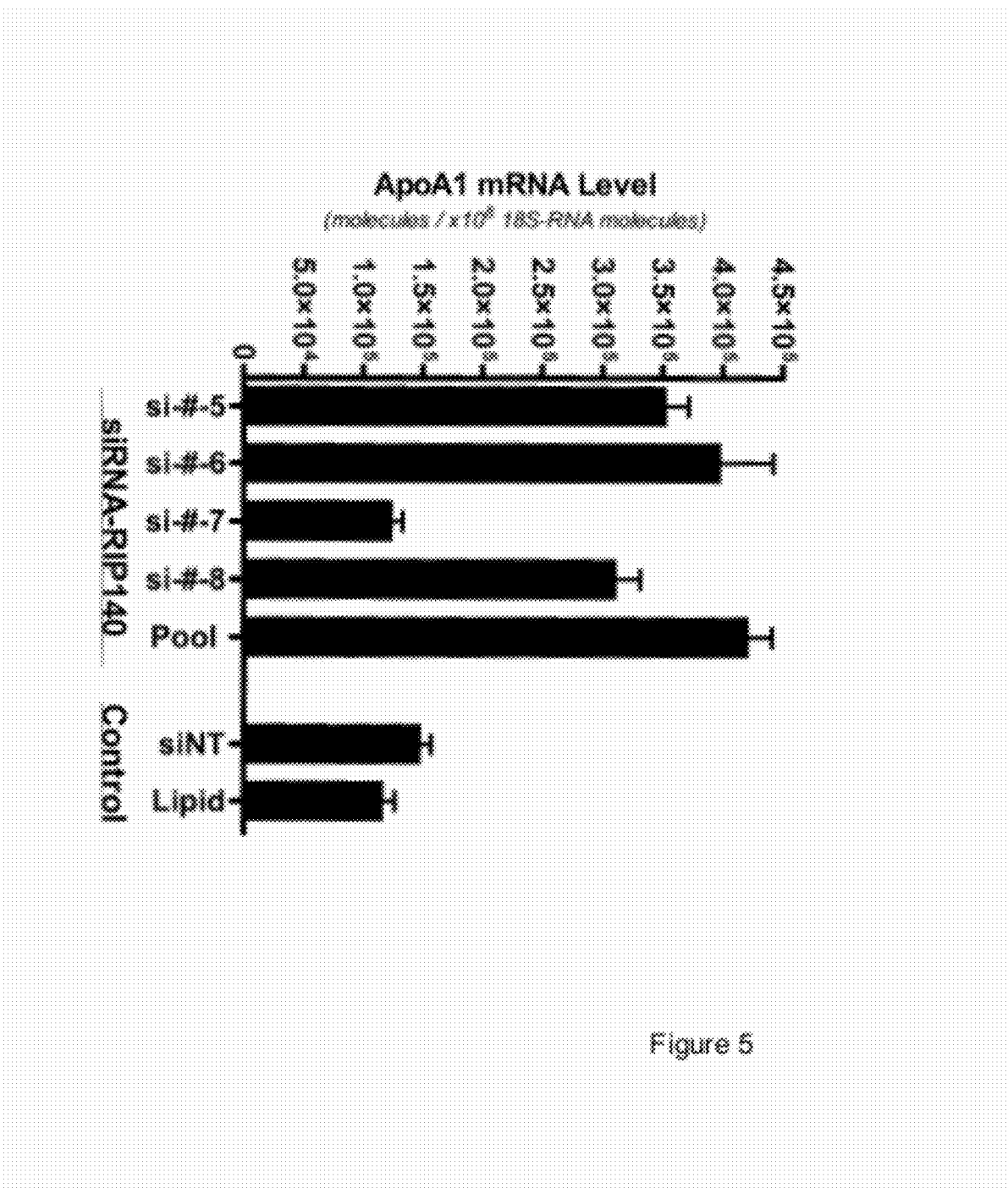
FIG. 5 is a bar graph illustrating an increase of apoA1 mRNA following treatment with individual NRIP1 siRNAs in HepG2 cells.
Figure 6:
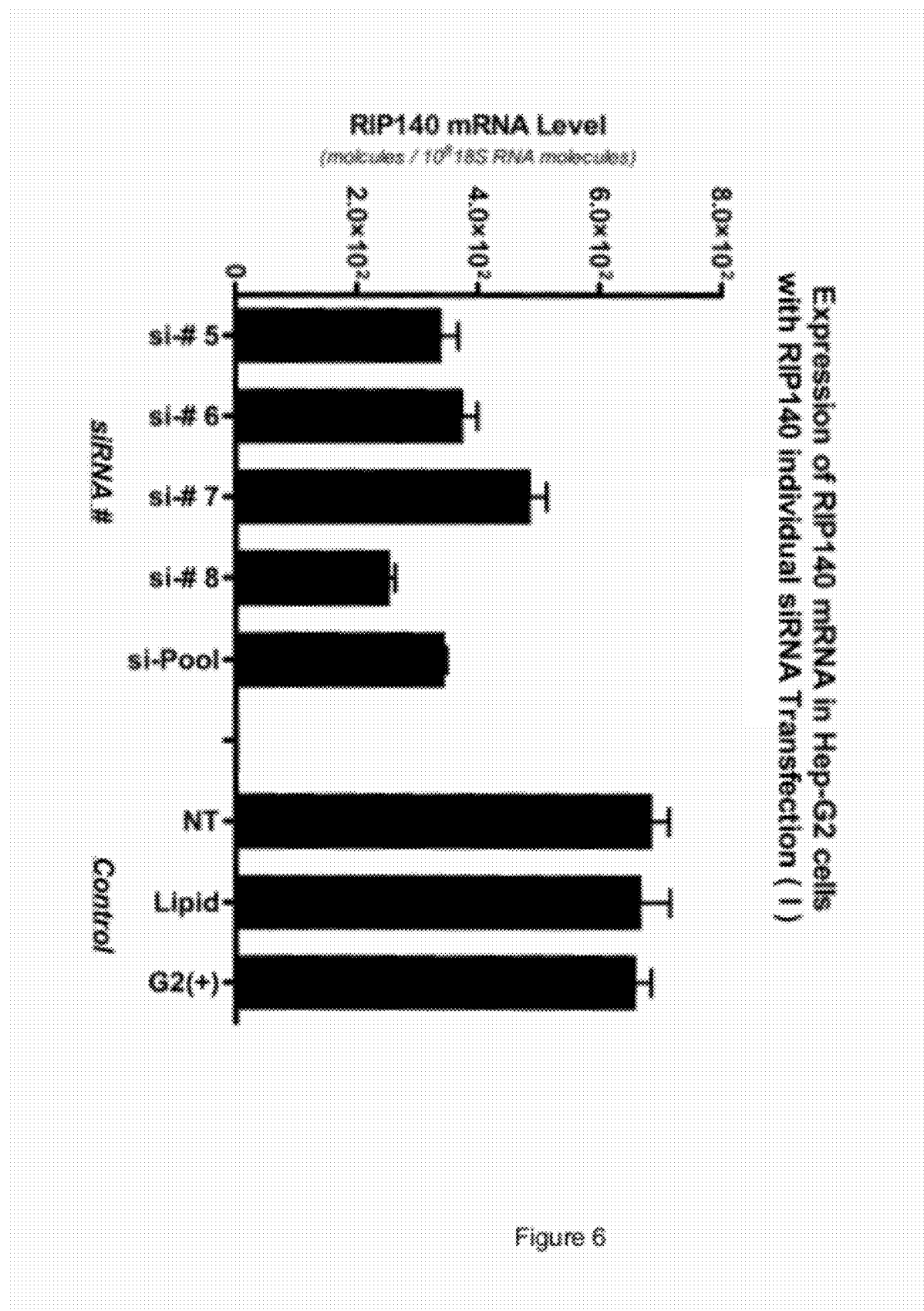
FIG. 6 is a bar graph illustrating a decrease of NRIP1 target mRNA following treatment with individual NRIP1 siRNAs in HepG2 cells.

HepG2 cells were transfected with four individual NRIP1 siRNA duplexes at a concentration of 100 nM or a pool of all four siRNAs at a final concentration 100 nM following the protocol previously described. Following isolation of total RNA, RT-qPCR was performed for apoA1 and NRIP1 gene expression. FIG. 5 compared apoA1 mRNA gene expression for siRNA samples to the siNT and lipid controls. In FIG. 6, expression levels of NRIP1 gene expression were similarly evaluated. The data revealed that the individual siRNA duplexes had varied potency on their ability to suppress the NRIP1 gene, with oligo #7 being the least effective inhibitor of NRIP1 expression and inducer of apoA1 gene expression.

Figure 7:
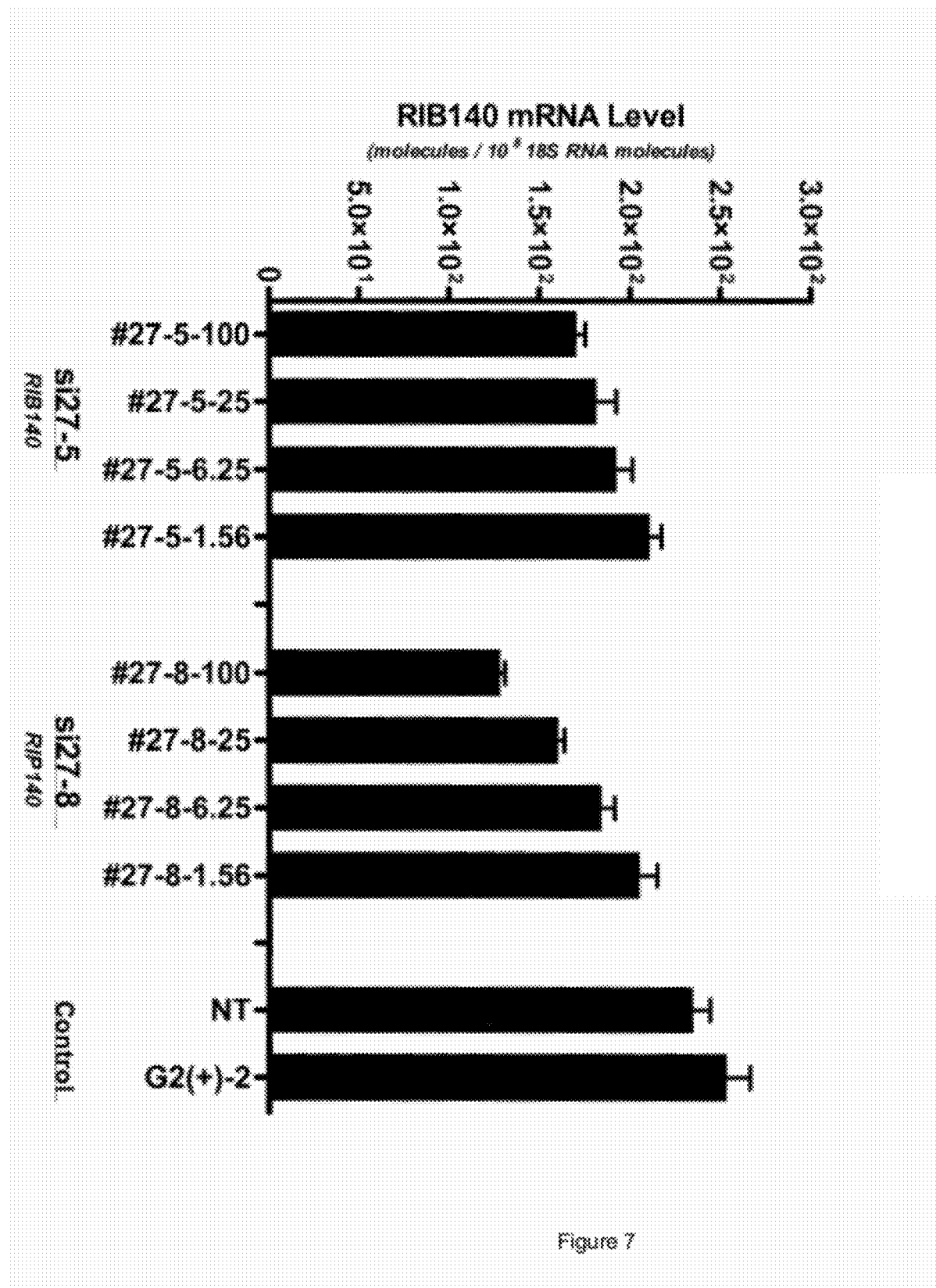
FIG. 7 is a bar graph illustrating a decrease of NRIP1 target mRNA levels following dose dependent treatment with two individual NRIP1 siRNA in HepG2 cells.

The differential effectiveness of individual sequence specific RNAi molecules to inhibit gene expression is well documented (Soutschek et al., Nature 432: 173-178 (2004)). In FIG. 7, we have taken the two most effective siRNA duplexes for dose response evaluation on NRIP1 target gene expression. The NRIP1 siRNA #5 and #8 were compare using 4-fold dilutions from 100 nM to 1.56 nM. Consistent with the observation in FIG. 7, NRIP1 gene expression was inhibited better by siRNA #8 over siRNA #5 at all doses tested.

Example 4

RNAi Decrease of NRIP1 Target mRNA Levels Following Treatment with Individual NRIP1 Dicer Substrate dsiRNA in HepG2 Cells The term RNA interference (RNAi) broadly encompasses several technological approaches to a process that interferes with protein expression at the mRNA level using small complementary RNA molecules. Double-stranded RNA (dsRNA), short-interfering RNA (siRNA) or microRNA (miRNA) have the capability to suppress gene expression through various mechanisms once the small RNA molecule ~22 nucleotides in length is incorporated in the multi-protein RNA-induced Silencing Complex (RISC). A mechanistic difference between the various small RNA molecules is the result of the site of entry into the multi-step processing apparatus that converts transcribed RNA into small paired duplex RNA molecules. In this example, we evaluated an RNAi molecules called Dicer substrate RNAi (dsiRNA) designed to target NRIP1. The dsiRNA differs from siRNA because it enters the processing apparatus one step earlier as a substrate for the Dicer duplex which in turn converts the dsiRNA into an siRNA. The experiment compares the suppressing activity of three dsiRNA developed by Integrated DNA Technologies (IDT). For NRIP1 the following dsiRNA duplex was used based on the NRIP1 sequence found under GenBank accession no. NM_173440.

dsiRNAi#1 sense 5'-AGACUAUACCUAAGC-CAAUGAAUGG (SEQ ID NO: 20), antisense 5'-CCAUUCAUUGGCUUAGGAUAGUCUGG (SEQ ID NO: 21)

dsiRNAi#2 sense 5'-AGGAGUCACA-GAAAUAAUGAAAUGG (SEQ ID NO: 22), antisense 5'-CCAUUUCAUUAUUUCUGUGACUC-CUGU (SEQ ID NO: 23)

dsiRNAi#3 sense 5'-AGCUAACAAAUACUGCAUC-UAACCA (SEQ ID NO: 24)

antisense 5'-UGGUUAGAUGCAGUAUUUG-UUAGCUUU (SEQ ID NO: 25).

Figure 8:
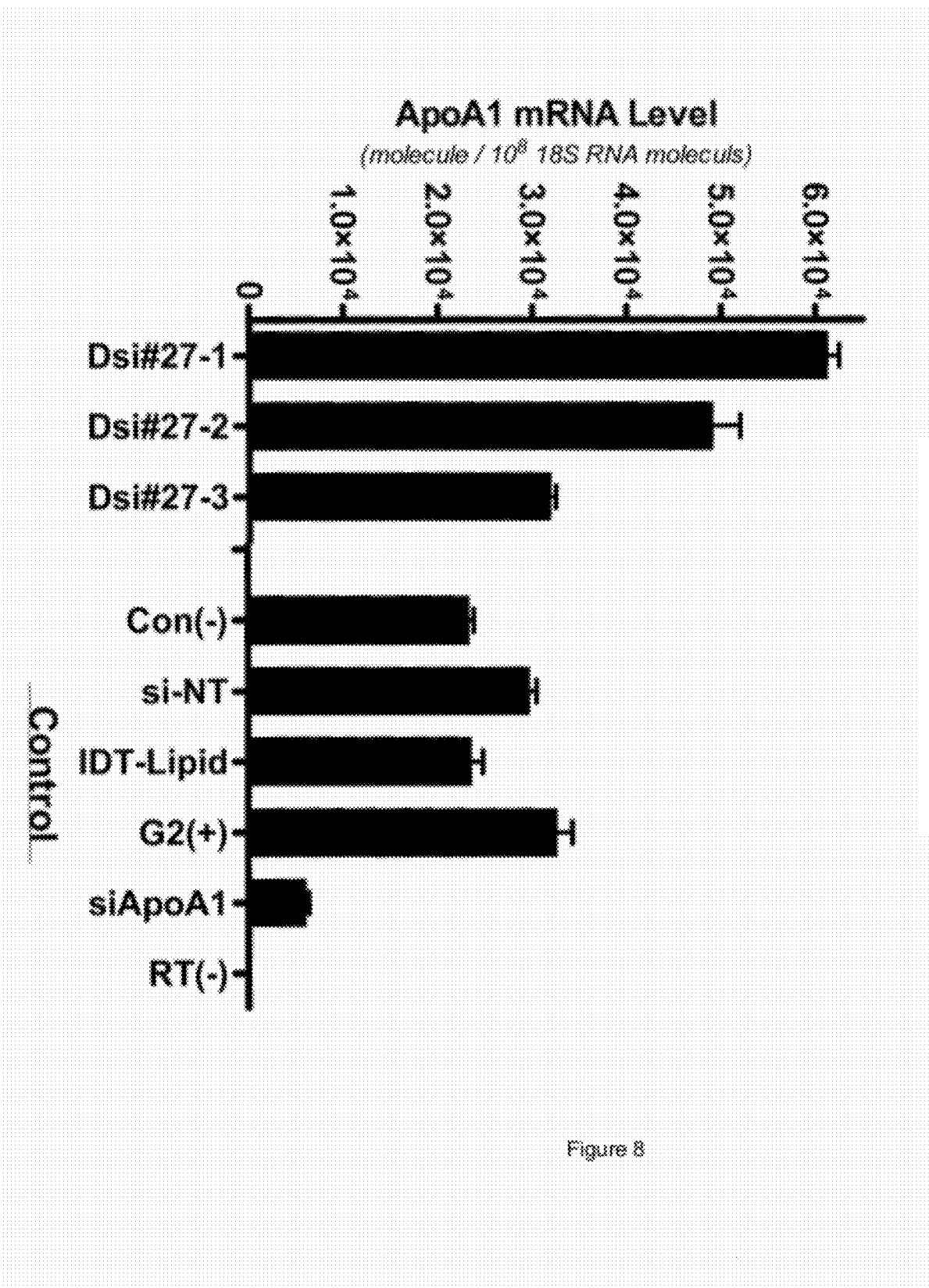
FIG. 8 is a bar graph illustrating an increase in apoA1 mRNA levels following treatment with three individual NRIP1 Dicer substrate RNAi in HepG2 cells.

In this experiment, the three dsiRNA duplexes were compared to several control treatments previously described which included apoA1 siRNA (siApoA1), untreated HepG2 cells (G2+), siRNA non-targeting control (si-NT), no reverse transcriptase (RT−), transfection lipid only (IDT-Lipid) and (Con−). As seen previously in the siRNA experiments, the individual dsiRNA duplex targeting NRIP1 demonstrated varied effectiveness at increasing apoA1 mRNA levels (FIG. 8). Treatment with both dsi#27-1 and dsi#27-2 induced elevated apoA1 mRNA expression (FIG. 8).

Example 5

Figure 9:
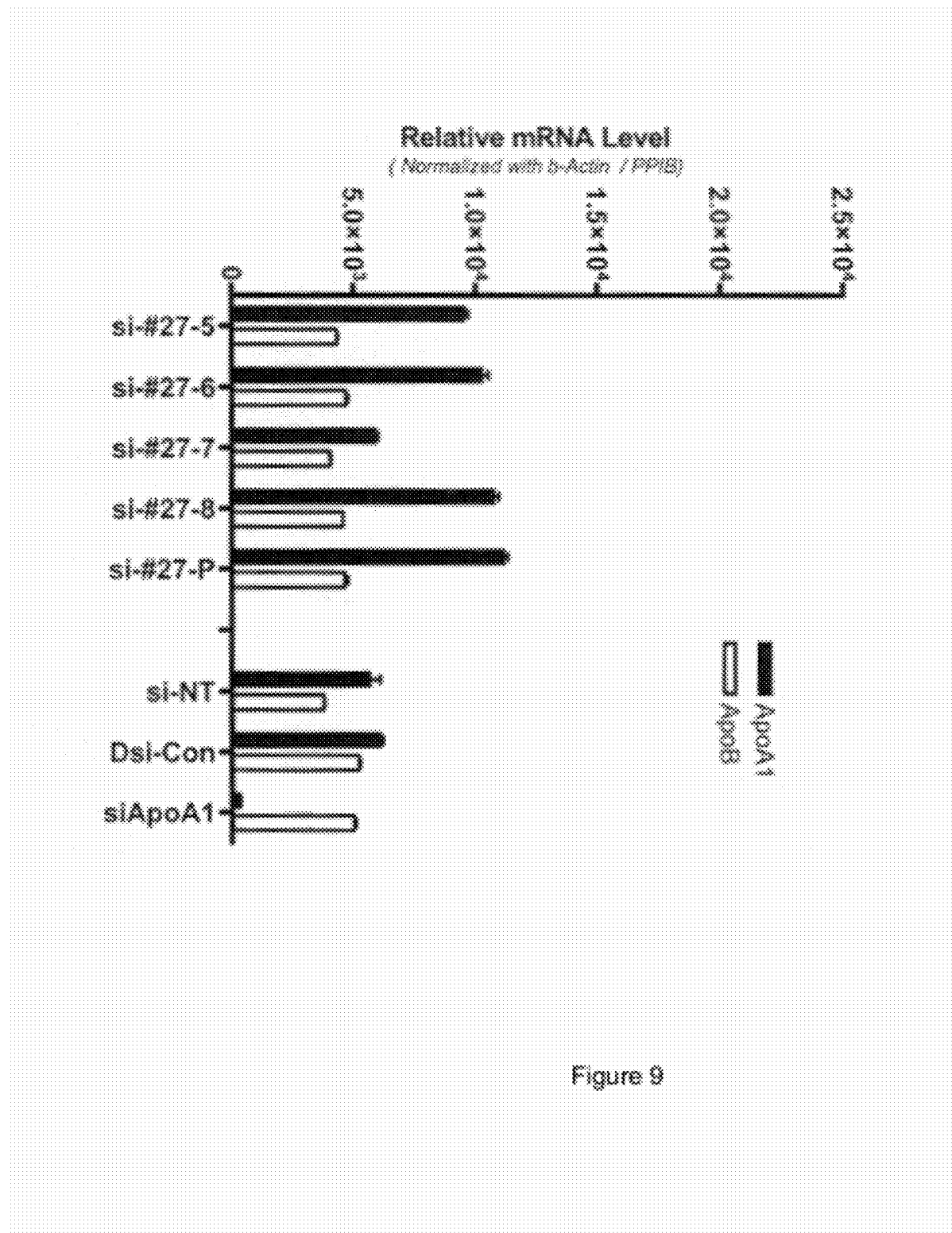
FIG. 9 is a bar graph illustrating the selective increase of apoA1 mRNA levels following treatment with individual NRIP1 siRNA in HepG2 cells and no changes in apoB mRNA levels.

Selective Increase in apoA1 Gene Expression without Increasing apoB Expression Levels Following NRIP1 RNAi Treatment in HepG2 Cells Transcription factors and modulators often regulate a number of genes as a means of coordinating cellular responses to environmental stimuli. When targeting specific transcriptional mechanisms, an important consideration is that in addition to achieving the desired regulation of the target gene(s), other gene(s), which may present adverse events, are not also affected. In this experiment we evaluated the effects of the four individual NRIP1 siRNA on apoB gene expression. Given the association of apoB in the unhealthy lipoproteins low-density lipoprotein (LDL), very low-density lipoproteins (VLDL) and chylomicrons we determined that suppression in NRIP1 expression did not cause in an increase in apoB gene expression (FIG. 9).

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

Patents, patent applications, publications, product descriptions, and protocols are cited throughout this application, the disclosures of which are incorporated herein by reference in their entireties for all purposes.

We claim:

1. A method for identifying an agent that increases expression of apolipoprotein A-1 (apoA1) comprising:
   contacting a cell comprising a nucleic acid encoding the nuclear receptor-interacting protein 1 (NRIP1) protein with a candidate agent that is a DNA or RNA molecule or a combination of DNA and RNA, which is complementary to the nucleic acid sense strand, under conditions in which the nucleic acid encoding the (NRIP1) is expressed; and, if expression of NRIP1 is reduced in the presence of the candidate agent,
   evaluating expression levels of apoA1 in the cell; wherein an increase in apoA1 polypeptide expression indicates that the candidate agent increases expression of apoA1.

2. The method of claim 1 wherein the candidate agent is an RNA molecule.

3. The method of claim 1 wherein the candidate agent is a DNA molecule.

4. The method of claim 1, further comprising evaluating apoA1 production in an animal which has been administered the identified candidate agent wherein the identification of the candidate agent is confirmed if apoA1 production occurs at a higher level in the animal than in the absence of the agent.

5. The method of claim 1 wherein the NRIP1 is human NRIP1.

6. The method of claim 5 wherein the human NRIP1 comprises the amino acid sequence:

7. A method for identifying an agent that increases expression of apolipoprotein A-1 (apoA1) comprising contacting a sample comprising nuclear receptor-interacting protein 1 (NRIP1) and peroxisome proliferator-activated receptor (PPAR) with a candidate agent and determining if said NRIP1 and PPAR bind in the presence of the candidate agent and, if said binding is decreased, then contacting a cell expressing apoA1 with the candidate agent and determining apoA1 expression wherein said agent is identified as an agent that increases expression of apoA1 if expression of apoA1 is determined to increase in the presence of the agent.

8. The method of claim 7 for identifying an agent that increases expression of apolipoprotein A-1 (apoA1) comprising
   (i) incubating a mixture comprising nuclear receptor-interacting protein 1 (NRIP1) polypeptide that is labeled with a FET donor label or FET acceptor label and peroxisome proliferator-activated receptor (PPAR) polypeptide that is labeled with the other label; under conditions which allow association between the polypeptides, in the presence of a candidate agent; wherein the donor and acceptor are chosen such that when the NRIP1 binds to PPAR, the donor and the acceptor are brought into interacting proximity, producing a detectable luminescence lifetime change in the photoluminescence lifetime of the donor; and

```
                                                              (SEQ ID NO: 4)
MLHGEELGSD VHQDSIVLLY LEGLLMHQAA GGSGLAVDKK SAGHNEEDQN FNISGSAFPL   60

CQSNGPVLNL HLYQGSGMLH LKKARLLQSS EDWNAAKRKR LSDSIMNLNV KKEALLAGMV  120

DSVPKGKQDS LLLASLLQSF SSRLQLVALS QQIRQSLKEQ GYALSHDSLK VEKDLRCYGV  180

ASSHLKLLLK KSKVKDQKPD LNLPDVLKNL IRDRFAESPH HVGQSGLKVM SEPLSCAARL  240

QAVASMVEKR ASPALSPKPS VACSQLALLL SSEAHLQOYS REHALKLQNA NQAASERLAA  300

MARLQENGQK DVGSYQLPKG MSSHLNGQAR LSSSKLMASK SSALVFQNPM GIIPSSPKNA  360

GYKNSLERNN IKQAANNSLL LHLLKSQLIP KPMNGHSHSE RGSIFEESSL PLLIDEYSDN  420

NPSFLDDSSG DESSYSNCVP IDLSCKHRLE KSESDQPVSL DNFLQSLLNL WDPKVPDVDI  480

KEDQDLSKNS KLNSHQKVLL LQLLLGHKNE ENVEKNLSPQ GVHNDVSKFN LQNYARLSVI  540

ESPSLNRLLP VSLPPLLLSS KAGSPINLSQ HSLVIKWNSP PYVCSLQSEK LLNLASNHSM  600

DLLKSKDPPG EKPAQNEGAQ NSALFSASKL LQNLAQCGMQ SSMSVEEQRP SKQLLLGNLD  660

KPIGMIDRLN SPLLSNKLNA VEENKAFSSQ PLGPEPGLSG SEIENLLERR LVLQLLLGNP  720

NKGKSEKKEK LPLRDESLQE HSERALSEQI LMVKIKSEPC DDLQIPNLNV HLSHDAKSAP  780

FLGMAPAVQR SAPALPVSED FKSEPVSPQD FSFSKNGLLS RLLRQNQDSY LADDSDRSHR  840

NNEMALLESK NLCMVPKKRK LYLEPLENPF KKMKNNIVDA ANNHSAPEVL YGSLLNQEEL  900

KFSRNDLEFK YPAGHGSASE SEHRSWARES KSFNVLKQLL LSENCVRDLS PHRSNSVADS  960

KKKGHKNNVL NSKPEFSISS LNGLMYSSLQ PSSCMDNRLF SYPGVVKLPV SPLFPEHLGC 1020

AGSRPESGLL NGCSMPSEKG PIKWVILDAE KNEYEKDSPR LLKLNPILYY MLQKGGNSVL 1080

SRELQDKDIW REASSAESVS QVLAKEELLP LAELKASFFN LRSPYNSHMG NNASRPHSAN 1140

GEVYGLLGSV LLIKKESE                                               1158
```

(ii) exposing the sample to an exciting amount of radiation, detecting the resulting emission; and calculating the apparent luminescence lifetime of the donor to quantify binding of the NRIP1 polypeptide to the PPAR; and if fluorescence by the donor occurs at a lower level than that observed in the absence of said candidate agent, then evaluating expression levels of the apoA1 in a cell in the presence of the candidate agent; wherein an increase in apoA1 polypeptide expression indicates that the candidate agent increases expression of apoA1.

9. The method of claim 7 wherein the PPAR is PPAR alpha.

10. The method of claim 7 wherein the PPAR is PPAR delta.

11. The method of claim 7 wherein the PPAR is PPAR gamma.

* * * * *